(12) United States Patent
Schneider et al.

(10) Patent No.: US 8,658,400 B2
(45) Date of Patent: Feb. 25, 2014

(54) BIOCATALYSTS FOR MANUFACTURING DULOXETINE ALCOHOL

(75) Inventors: Nina Schneider, Offenburg (DE); Hans Wolfgang Höffken, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 1 day.

(21) Appl. No.: 13/140,255

(22) PCT Filed: Dec. 16, 2009

(86) PCT No.: PCT/EP2009/067341
§ 371 (c)(1),
(2), (4) Date: Jun. 16, 2011

(87) PCT Pub. No.: WO2010/079068
PCT Pub. Date: Jul. 15, 2010

(65) Prior Publication Data
US 2011/0250655 A1    Oct. 13, 2011

(30) Foreign Application Priority Data
Dec. 17, 2008    (EP) .................................... 08172003

(51) Int. Cl.
| C12P 17/00 | (2006.01) |
| C12P 7/02 | (2006.01) |
| C12N 9/04 | (2006.01) |
| C12N 1/20 | (2006.01) |
| C12P 21/06 | (2006.01) |
| C12N 15/00 | (2006.01) |
| C07D 333/12 | (2006.01) |
| C07H 21/04 | (2006.01) |
| C07K 1/00 | (2006.01) |

(52) U.S. Cl.
USPC ........ 435/117; 435/155; 435/190; 435/252.3; 435/69.1; 435/320.1; 549/75; 536/23.1; 536/23.2; 530/350

(58) Field of Classification Search
USPC .......... 435/117, 155, 190, 252.3, 69.1, 320.1; 549/75; 536/23.1, 23.2; 530/350
See application file for complete search history.

(56) References Cited

U.S. PATENT DOCUMENTS

| 7,498,448 B2 | 3/2009 | Stürmer et al. |
| 7,785,847 B2 | 8/2010 | Sturmer et al. |
| 2008/0206824 A1* | 8/2008 | Sturmer et al. ............... 435/117 |

FOREIGN PATENT DOCUMENTS

| WO | WO-2005/033094 A2 | 4/2005 |
| WO | WO-2005/108590 A2 | 11/2005 |
| WO | WO-2006/094945 A2 | 9/2006 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Abokitse, K., et al., "Cloning, Sequence Analysis, and Heterologous Expression of the Gene Encoding a (S)-specific Alcohol Dehydrogenase from *Rhodococcus erythropolis* DSM 43297", Appl. Microbiol Biotechnol., 2003, vol. 62, pp. 380-386.
Hoffken et al., "Crystal Structure and Enzyme Kinetics of the (S)-Specific 1-Phenylethanol Dehydrogenase of the Denitrifying Bacterium Strain EbN1", Biochemistry, 2006, vol. 45, pp. 82-93.

* cited by examiner

*Primary Examiner* — Ganapathirama Raghu
(74) *Attorney, Agent, or Firm* — Novak Druce Connolly Bove + Quigg LLP

(57) ABSTRACT

The present invention relates to novel phenylethanol dehydrogenase mutants, to a method for the manufacture thereof; to coded nucleic acid sequences therefor, to expression cassettes, to vectors and recombinant microorganisms that contain said sequences; to a method for the biocatalytic synthesis of substituted, optically active alcohols and to the use of said mutants; and particularly to a method for manufacturing duloxetine alcohol or duloxetine, comprising a synthesis step catalyzed biocatalytic by said mutants.

25 Claims, 16 Drawing Sheets

(A)

```
  1 atgacgcaaa gactgaagga caagcttgca gtaattaccg gcggtgccaa cggcatcggg
 61 cgggcaattg cggagcgatt tgcggtcgaa ggtgccgaca tcgcaatcgc ggatctggtg
121 ccggccccgg aagccgaggc agcaatcagg aacctcggtc ggcgcgttct gaccgtgaag
181 tgcgatgtct cgcaacctgg cgacgtagaa gcattcggaa agcaggtcat ctccacgttt
241 ggtcgctgcg acatcctcgt caacaacgcg ggaatttacc cgctgattcc ttttgacgag
301 ctgacctttg aacagtggaa gaaaacattc gagatcaacg tcgattcagg ttttcttatg
361 gcgaaggctt ttgtccccgg gatgaagagg aacgggtggg gacgcatcat caacctgact
421 tcgacgacat attggctaaa gatcgaggcg tatacccatt acatcagcac gaaagcggca
481 aacataggct ttaccgcgc ccttgcctcg gacctgggga aggacggaat cactgttaac
541 gccatcgcgc cgagccttgt ccgcacggca acaaccgaag cttctgcatt gtccgcgatg
601 ttcgacgtgc tgccaaacat gcttcaggcg attccgcgtc ttcaggtgcc cctggatctg
661 acgggcgcag ctgcgttcct ggcttccgat gacgccagtt ttattacagg ccagacgctc
721 gcggttgatg gcggtatggt gagacactga
```

(B)

```
  1 MTQRLKDKLA VITGGANGIG RAIAERFAVE GADIAIADLV PAPEAEAAIR
 51 NLGRRVLTVK CDVSQPGDVE AFGKQVISTF GRCDILVNNA GIYPLIPFDE
101 LTFEQWKKTF EINVDSGFLM AKAFVPGMKR NGWGRIINLT STTYWLKIEA
151 YTHYISTKAA NIGFTRALAS DLGKDGITVN AIAPSLVRTA TTEASALSAM
201 FDVLPNMLQA IPRLQVPLDL TGAAAFLASD DASFITGQTL AVDGGMVRH
```

Fig. 1 pDHE-ebn1H-Y151X
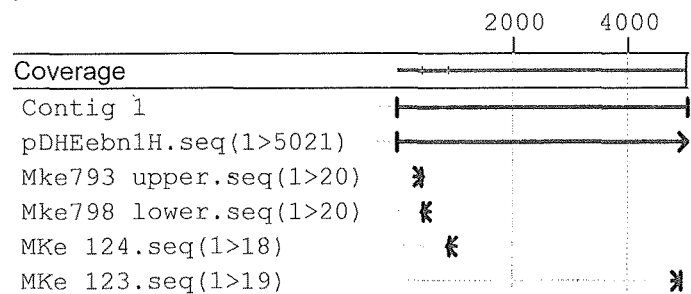
pDHE-ebn1H-T192X
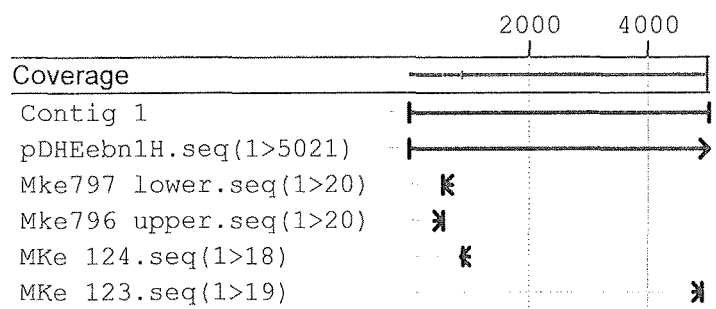
pDHE-ebn1H-Y151A-T192X
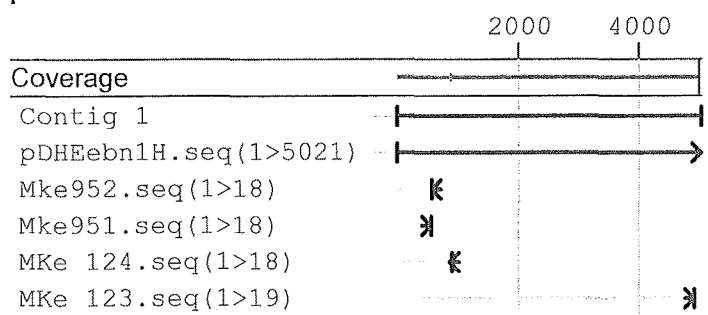
Fig.3

SEQUENCE LISTING

```
<160> NUMBER OF SEQ ID NOS: 140

<210> SEQ ID NO 1
<211> LENGTH: 750
<212> TYPE: DNA
<213> ORGANISM: Azoarcus sp.
<220> FEATURE:
<221> NAME/KEY: CDS
<222> LOCATION: (1)..(750)
```

<400> SEQUENCE: 1

```
atg acg caa aga ctg aag gac aag ctt gca gta att acc ggc ggt gcc      48
Met Thr Gln Arg Leu Lys Asp Lys Leu Ala Val Ile Thr Gly Gly Ala
1               5                   10                  15 aac ggc atc ggg cgg gca att gcg gag cga ttt gcg gtc gaa ggt gcc      96
Asn Gly Ile Gly Arg Ala Ile Ala Glu Arg Phe Ala Val Glu Gly Ala
            20                  25                  30 gac atc gca atc gcg gat ctg gtg ccg gcc ccg gaa gcc gag gca gca     144
Asp Ile Ala Ile Ala Asp Leu Val Pro Ala Pro Glu Ala Glu Ala Ala
        35                  40                  45 atc agg aac ctc ggt cgg cgc gtt ctg acc gtg aag tgc gat gtc tcg     192
Ile Arg Asn Leu Gly Arg Arg Val Leu Thr Val Lys Cys Asp Val Ser
    50                  55                  60 caa cct ggc gac gta gaa gca ttc gga aag cag gtc atc tcc acg ttt     240
Gln Pro Gly Asp Val Glu Ala Phe Gly Lys Gln Val Ile Ser Thr Phe
65                  70                  75                  80 ggt cgc tgc gac atc ctc gtc aac aac gcg gga att tac ccg ctg att     288
Gly Arg Cys Asp Ile Leu Val Asn Asn Ala Gly Ile Tyr Pro Leu Ile
                85                  90                  95 cct ttt gac gag ctg acc ttt gaa cag tgg aag aaa aca ttc gag atc     336
Pro Phe Asp Glu Leu Thr Phe Glu Gln Trp Lys Lys Thr Phe Glu Ile
            100                 105                 110 aac gtc gat tca ggt ttt ctt atg gcg aag gct ttt gtc ccc ggg atg     384
Asn Val Asp Ser Gly Phe Leu Met Ala Lys Ala Phe Val Pro Gly Met
        115                 120                 125 aag agg aac ggg tgg gga cgc atc atc aac ctg act tcg acg aca tat     432
Lys Arg Asn Gly Trp Gly Arg Ile Ile Asn Leu Thr Ser Thr Thr Tyr
    130                 135                 140 tgg cta aag atc gag gcg tat acc cat tac atc agc acg aaa gcg gca     480
Trp Leu Lys Ile Glu Ala Tyr Thr His Tyr Ile Ser Thr Lys Ala Ala
145                 150                 155                 160 aac ata ggc ttt acc cgc gcc ctt gcc tcg gac ctg ggg aag gac gga     528
Asn Ile Gly Phe Thr Arg Ala Leu Ala Ser Asp Leu Gly Lys Asp Gly
                165                 170                 175 atc act gtt aac gcc atc gcg ccg agc ctt gtc cgc acg gca aca acc     576
Ile Thr Val Asn Ala Ile Ala Pro Ser Leu Val Arg Thr Ala Thr Thr
            180                 185                 190 gaa gct tct gca ttg tcc gcg atg ttc gac gtg ctg cca aac atg ctt     624
Glu Ala Ser Ala Leu Ser Ala Met Phe Asp Val Leu Pro Asn Met Leu
        195                 200                 205 cag gcg att ccg cgt ctt cag gtg ccc ctg gat ctg acg ggc gca gct     672
Gln Ala Ile Pro Arg Leu Gln Val Pro Leu Asp Leu Thr Gly Ala Ala
    210                 215                 220 gcg ttc ctg gct tcc gat gac gcc agt ttt att aca ggc cag acg ctc     720
Ala Phe Leu Ala Ser Asp Asp Ala Ser Phe Ile Thr Gly Gln Thr Leu
225                 230                 235                 240 gcg gtt gat ggc ggt atg gtg aga cac tga                             750
Ala Val Asp Gly Gly Met Val Arg His
                245
```

<210> SEQ ID NO 2
<211> LENGTH: 249
<212> TYPE: PRT
<213> ORGANISM: Azoarcus sp.

<400> SEQUENCE: 2

```
Met Thr Gln Arg Leu Lys Asp Lys Leu Ala Val Ile Thr Gly Gly Ala
1               5                   10                  15

Asn Gly Ile Gly Arg Ala Ile Ala Glu Arg Phe Ala Val Glu Gly Ala
            20                  25                  30
```

```
Asp Ile Ala Ile Ala Asp Leu Val Pro Ala Pro Glu Ala Glu Ala Ala
            35                  40                  45

Ile Arg Asn Leu Gly Arg Arg Val Leu Thr Val Lys Cys Asp Val Ser
 50                  55                  60

Gln Pro Gly Asp Val Glu Ala Phe Gly Lys Gln Val Ile Ser Thr Phe
 65                  70                  75                  80

Gly Arg Cys Asp Ile Leu Val Asn Asn Ala Gly Ile Tyr Pro Leu Ile
                 85                  90                  95

Pro Phe Asp Glu Leu Thr Phe Glu Gln Trp Lys Lys Thr Phe Glu Ile
            100                 105                 110

Asn Val Asp Ser Gly Phe Leu Met Ala Lys Ala Phe Val Pro Gly Met
            115                 120                 125

Lys Arg Asn Gly Trp Gly Arg Ile Ile Asn Leu Thr Ser Thr Thr Tyr
        130                 135                 140

Trp Leu Lys Ile Glu Ala Tyr Thr His Tyr Ile Ser Thr Lys Ala Ala
145                 150                 155                 160

Asn Ile Gly Phe Thr Arg Ala Leu Ala Ser Asp Leu Gly Lys Asp Gly
                165                 170                 175

Ile Thr Val Asn Ala Ile Ala Pro Ser Leu Val Arg Thr Ala Thr Thr
            180                 185                 190

Glu Ala Ser Ala Leu Ser Ala Met Phe Asp Val Leu Pro Asn Met Leu
            195                 200                 205

Gln Ala Ile Pro Arg Leu Gln Val Pro Leu Asp Leu Thr Gly Ala Ala
            210                 215                 220

Ala Phe Leu Ala Ser Asp Asp Ala Ser Phe Ile Thr Gly Gln Thr Leu
225                 230                 235                 240

Ala Val Asp Gly Gly Met Val Arg His
                245

<210> SEQ ID NO 3
<211> LENGTH: 750
<212> TYPE: DNA
<213> ORGANISM: Azoarcus sp.
<220> FEATURE:
<221> NAME/KEY: CDS
<222> LOCATION: (1)..(750)

<400> SEQUENCE: 3 atg acg caa aga ctg aag gac aag ctg gca gta att acc ggc ggt gcc      48
Met Thr Gln Arg Leu Lys Asp Lys Leu Ala Val Ile Thr Gly Gly Ala
 1               5                  10                  15 aac ggc atc ggg cgg gca att gcg gag cga ttt gcg gtc gaa ggt gcc      96
Asn Gly Ile Gly Arg Ala Ile Ala Glu Arg Phe Ala Val Glu Gly Ala
                20                  25                  30 gac atc gca atc gcg gat ctg gtg ccg gcc ccg gaa gcc gag gca gca     144
Asp Ile Ala Ile Ala Asp Leu Val Pro Ala Pro Glu Ala Glu Ala Ala
            35                  40                  45 atc agg aac ctc ggt cgg cgc gtt ctg acc gtg aag tgc gat gtc tcg     192
Ile Arg Asn Leu Gly Arg Arg Val Leu Thr Val Lys Cys Asp Val Ser
 50                  55                  60 caa cct ggc gac gta gaa gca ttc gga aag cag gtc atc tcc acg ttt     240
Gln Pro Gly Asp Val Glu Ala Phe Gly Lys Gln Val Ile Ser Thr Phe
 65                  70                  75                  80 ggt cgc tgc gac atc ctc gtc aac aac gcg gga att tac ccg ctg att     288
Gly Arg Cys Asp Ile Leu Val Asn Asn Ala Gly Ile Tyr Pro Leu Ile
                 85                  90                  95 cct ttt gac gag ctg acc ttt gaa cag tgg aag aaa aca ttc gag atc     336
Pro Phe Asp Glu Leu Thr Phe Glu Gln Trp Lys Lys Thr Phe Glu Ile
```

```
                            100                 105                 110
aac gtc gat tca ggt ttt ctt atg gcg aag gct ttt gtc ccc ggg atg        384
Asn Val Asp Ser Gly Phe Leu Met Ala Lys Ala Phe Val Pro Gly Met
            115                 120                 125 aag agg aac ggg tgg gga cgc atc atc aac ctg act tcg acg aca tat        432
Lys Arg Asn Gly Trp Gly Arg Ile Ile Asn Leu Thr Ser Thr Thr Tyr
        130                 135                 140 tgg cta aag atc gag gcg gca acc cat tac atc agc acg aaa gcg gca        480
Trp Leu Lys Ile Glu Ala Ala Thr His Tyr Ile Ser Thr Lys Ala Ala
145                 150                 155                 160 aac ata ggc ttt acc cgc gcc ctt gcc tcg gac ctg ggg aag gac gga        528
Asn Ile Gly Phe Thr Arg Ala Leu Ala Ser Asp Leu Gly Lys Asp Gly
                165                 170                 175 atc act gtt aac gcc atc gcg ccg agc ctt gtc cgc acg gca aca acc        576
Ile Thr Val Asn Ala Ile Ala Pro Ser Leu Val Arg Thr Ala Thr Thr
            180                 185                 190 gaa gcg tct gca ttg tcc gcg atg ttc gac gtg ctg cca aac atg ctt        624
Glu Ala Ser Ala Leu Ser Ala Met Phe Asp Val Leu Pro Asn Met Leu
        195                 200                 205 cag gcg att ccg cgt ctt cag gtg ccc ctg gat ctg acg ggc gca gct        672
Gln Ala Ile Pro Arg Leu Gln Val Pro Leu Asp Leu Thr Gly Ala Ala
    210                 215                 220 gcg ttc ctg gct tcc gat gac gcc agt ttt att aca ggc cag acg ctc        720
Ala Phe Leu Ala Ser Asp Asp Ala Ser Phe Ile Thr Gly Gln Thr Leu
225                 230                 235                 240 gcg gtt gat ggc ggt atg gtg aga cac taa                                750
Ala Val Asp Gly Gly Met Val Arg His
                245

<210> SEQ ID NO 4
<211> LENGTH: 249
<212> TYPE: PRT
<213> ORGANISM: Azoarcus sp.

<400> SEQUENCE: 4

Met Thr Gln Arg Leu Lys Asp Lys Leu Ala Val Ile Thr Gly Gly Ala
1               5                   10                  15

Asn Gly Ile Gly Arg Ala Ile Ala Glu Arg Phe Ala Val Glu Gly Ala
            20                  25                  30

Asp Ile Ala Ile Ala Asp Leu Val Pro Ala Pro Glu Ala Glu Ala Ala
        35                  40                  45

Ile Arg Asn Leu Gly Arg Arg Val Leu Thr Val Lys Cys Asp Val Ser
    50                  55                  60

Gln Pro Gly Asp Val Glu Ala Phe Gly Lys Gln Val Ile Ser Thr Phe
65                  70                  75                  80

Gly Arg Cys Asp Ile Leu Val Asn Asn Ala Gly Ile Tyr Pro Leu Ile
                85                  90                  95

Pro Phe Asp Glu Leu Thr Phe Glu Gln Trp Lys Lys Thr Phe Glu Ile
            100                 105                 110

Asn Val Asp Ser Gly Phe Leu Met Ala Lys Ala Phe Val Pro Gly Met
        115                 120                 125

Lys Arg Asn Gly Trp Gly Arg Ile Ile Asn Leu Thr Ser Thr Thr Tyr
    130                 135                 140

Trp Leu Lys Ile Glu Ala Ala Thr His Tyr Ile Ser Thr Lys Ala Ala
145                 150                 155                 160

Asn Ile Gly Phe Thr Arg Ala Leu Ala Ser Asp Leu Gly Lys Asp Gly
                165                 170                 175

Ile Thr Val Asn Ala Ile Ala Pro Ser Leu Val Arg Thr Ala Thr Thr
```

-continued

```
                180                 185                 190
Glu Ala Ser Ala Leu Ser Ala Met Phe Asp Val Leu Pro Asn Met Leu
        195                 200                 205

Gln Ala Ile Pro Arg Leu Gln Val Pro Leu Asp Leu Thr Gly Ala Ala
    210                 215                 220

Ala Phe Leu Ala Ser Asp Asp Ala Ser Phe Ile Thr Gly Gln Thr Leu
225                 230                 235                 240

Ala Val Asp Gly Gly Met Val Arg His
                245
```

<210> SEQ ID NO 5
<211> LENGTH: 19
<212> TYPE: DNA
<213> ORGANISM: Artificial sequence
<220> FEATURE:
<223> OTHER INFORMATION: PCR primer

<400> SEQUENCE: 5
gttcatcttt ccctggttg                                                    19

<210> SEQ ID NO 6
<211> LENGTH: 18
<212> TYPE: DNA
<213> ORGANISM: Artificial sequence
<220> FEATURE:
<223> OTHER INFORMATION: PCR primer

<400> SEQUENCE: 6
gctacggcgt ttcacttc                                                     18

<210> SEQ ID NO 7
<211> LENGTH: 20
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (10)..(12)
<223> OTHER INFORMATION: n is a, c, g, or t

<400> SEQUENCE: 7
gtaatgggtn nncgcctcga                                                   20

<210> SEQ ID NO 8
<211> LENGTH: 20
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (9)..(11)
<223> OTHER INFORMATION: n is a, c, g, or t

<400> SEQUENCE: 8
tcgaggcgnn nacccattac                                                   20

<210> SEQ ID NO 9
<211> LENGTH: 19
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (9)..(11)

<223> OTHER INFORMATION: n is a, c, g, or t

<400> SEQUENCE: 9
cggcaacann ngaagcgtc                                                19

<210> SEQ ID NO 10
<211> LENGTH: 20
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (9)..(11)
<223> OTHER INFORMATION: n is a, c, g, or t

<400> SEQUENCE: 10
gacgcttcnn ntgttgccgt                                               20

<210> SEQ ID NO 11
<211> LENGTH: 18
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (8)..(10)
<223> OTHER INFORMATION: n is a, c, g, or t

<400> SEQUENCE: 11
ggcaacannn gaagcgtc                                                 18

<210> SEQ ID NO 12
<211> LENGTH: 18
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (9)..(11)
<223> OTHER INFORMATION: n is a, c, g, or t

<400> SEQUENCE: 12
gacgcttcnn ntgttgcc                                                 18

<210> SEQ ID NO 13
<211> LENGTH: 20
<212> TYPE: DNA
<213> ORGANISM: Artificial sequence
<220> FEATURE:
<223> OTHER INFORMATION: PCR primer

<400> SEQUENCE: 13
catcatcaac gcgacttcga                                               20

<210> SEQ ID NO 14
<211> LENGTH: 20
<212> TYPE: DNA
<213> ORGANISM: Artificial sequence
<220> FEATURE:
<223> OTHER INFORMATION: PCR primer

<400> SEQUENCE: 14
tcgaagtcgc gttgatgatg                                               20

<210> SEQ ID NO 15

```
<211> LENGTH: 24
<212> TYPE: DNA
<213> ORGANISM: Artificial sequence
<220> FEATURE:
<223> OTHER INFORMATION: PCR primer

<400> SEQUENCE: 15
cgacatattg gatgaagatc gagg                                           24

<210> SEQ ID NO 16
<211> LENGTH: 24
<212> TYPE: DNA
<213> ORGANISM: Artificial sequence
<220> FEATURE:
<223> OTHER INFORMATION: PCR primer

<400> SEQUENCE: 16
cctcgatctt catccaatat gtcg                                           24

<210> SEQ ID NO 17
<211> LENGTH: 23
<212> TYPE: DNA
<213> ORGANISM: Artificial sequence
<220> FEATURE:
<223> OTHER INFORMATION: PCR primer

<400> SEQUENCE: 17
catattggct aaaggtggag gcg                                            23

<210> SEQ ID NO 18
<211> LENGTH: 23
<212> TYPE: DNA
<213> ORGANISM: Artificial sequence
<220> FEATURE:
<223> OTHER INFORMATION: PCR primer

<400> SEQUENCE: 18
cgcctccacc tttagccaat atg                                            23

<210> SEQ ID NO 19
<211> LENGTH: 20
<212> TYPE: DNA
<213> ORGANISM: Artificial sequence
<220> FEATURE:
<223> OTHER INFORMATION: PCR primer

<400> SEQUENCE: 19
tcgaggcggc gacccattac                                                20

<210> SEQ ID NO 20
<211> LENGTH: 20
<212> TYPE: DNA
<213> ORGANISM: Artificial sequence
<220> FEATURE:
<223> OTHER INFORMATION: PCR primer

<400> SEQUENCE: 20
gtaatgggtc gccgcctcga                                                20

<210> SEQ ID NO 21
<211> LENGTH: 19
<212> TYPE: DNA
<213> ORGANISM: Artificial sequence
<220> FEATURE:
<223> OTHER INFORMATION: PCR primer

<400> SEQUENCE: 21
```
cgtgaaggcg gatgtctcg                                                    19

<210> SEQ ID NO 22
<211> LENGTH: 19
<212> TYPE: DNA
<213> ORGANISM: Artificial sequence
<220> FEATURE:
<223> OTHER INFORMATION: PCR primer

<400> SEQUENCE: 22
cgagacatcc gccttcacg                                                    19

<210> SEQ ID NO 23
<211> LENGTH: 19
<212> TYPE: DNA
<213> ORGANISM: Artificial sequence
<220> FEATURE:
<223> OTHER INFORMATION: PCR primer

<400> SEQUENCE: 23
cgtgaagagc gatgtctcg                                                    19

<210> SEQ ID NO 24
<211> LENGTH: 19
<212> TYPE: DNA
<213> ORGANISM: Artificial sequence
<220> FEATURE:
<223> OTHER INFORMATION: PCR primer

<400> SEQUENCE: 24
cgagacatcg ctcttcacg                                                    19

<210> SEQ ID NO 25
<211> LENGTH: 24
<212> TYPE: DNA
<213> ORGANISM: Artificial sequence
<220> FEATURE:
<223> OTHER INFORMATION: PCR primer

<400> SEQUENCE: 25
ccacgtttgg tcgcgcggac atcc                                              24

<210> SEQ ID NO 26
<211> LENGTH: 24
<212> TYPE: DNA
<213> ORGANISM: Artificial sequence
<220> FEATURE:
<223> OTHER INFORMATION: PCR primer

<400> SEQUENCE: 26
ggatgtccgc gcgaccaaac gtgg                                              24

<210> SEQ ID NO 27
<211> LENGTH: 19
<212> TYPE: DNA
<213> ORGANISM: Artificial sequence
<220> FEATURE:
<223> OTHER INFORMATION: PCR primer

<400> SEQUENCE: 27
gtttggtcgc agcgacatc                                                    19

<210> SEQ ID NO 28
<211> LENGTH: 19
<212> TYPE: DNA
<213> ORGANISM: Artificial sequence
<220> FEATURE:

<223> OTHER INFORMATION: PCR primer

<400> SEQUENCE: 28
gatgtcgctg cgaccaaac                                         19

<210> SEQ ID NO 29
<211> LENGTH: 21
<212> TYPE: DNA
<213> ORGANISM: Artificial sequence
<220> FEATURE:
<223> OTHER INFORMATION: PCR primer

<400> SEQUENCE: 29
catcaacctg gcgtcgacga c                                      21

<210> SEQ ID NO 30
<211> LENGTH: 23
<212> TYPE: DNA
<213> ORGANISM: Artificial sequence
<220> FEATURE:
<223> OTHER INFORMATION: PCR primer

<400> SEQUENCE: 30
gtcgtcgacg ccaggttgat gat                                    23

<210> SEQ ID NO 31
<211> LENGTH: 23
<212> TYPE: DNA
<213> ORGANISM: Artificial sequence
<220> FEATURE:
<223> OTHER INFORMATION: PCR primer

<400> SEQUENCE: 31
caacctgagc tcgacgacat att                                    23

<210> SEQ ID NO 32
<211> LENGTH: 23
<212> TYPE: DNA
<213> ORGANISM: Artificial sequence
<220> FEATURE:
<223> OTHER INFORMATION: PCR primer

<400> SEQUENCE: 32
aatatgtcgt cgagctcagg ttg                                    23

<210> SEQ ID NO 33
<211> LENGTH: 24
<212> TYPE: DNA
<213> ORGANISM: Artificial sequence
<220> FEATURE:
<223> OTHER INFORMATION: PCR primer

<400> SEQUENCE: 33
catcatcaac ctgggctcga cgac                                   24

<210> SEQ ID NO 34
<211> LENGTH: 24
<212> TYPE: DNA
<213> ORGANISM: Artificial sequence
<220> FEATURE:
<223> OTHER INFORMATION: PCR primer

<400> SEQUENCE: 34
gtcgtcgagc ccaggttgat gatg                                   24

<210> SEQ ID NO 35

```
<211> LENGTH: 24
<212> TYPE: DNA
<213> ORGANISM: Artificial sequence
<220> FEATURE:
<223> OTHER INFORMATION: PCR primer

<400> SEQUENCE: 35
caacctgact tcgctgacat attg                                              24

<210> SEQ ID NO 36
<211> LENGTH: 24
<212> TYPE: DNA
<213> ORGANISM: Artificial sequence
<220> FEATURE:
<223> OTHER INFORMATION: PCR primer

<400> SEQUENCE: 36
caatatgtca gcgaagtcag gttg                                              24

<210> SEQ ID NO 37
<211> LENGTH: 24
<212> TYPE: DNA
<213> ORGANISM: Artificial sequence
<220> FEATURE:
<223> OTHER INFORMATION: PCR primer

<400> SEQUENCE: 37
caacctgact tcgagcacat attg                                              24

<210> SEQ ID NO 38
<211> LENGTH: 24
<212> TYPE: DNA
<213> ORGANISM: Artificial sequence
<220> FEATURE:
<223> OTHER INFORMATION: PCR primer

<400> SEQUENCE: 38
caatatgtgc tcgaagtcag gttg                                              24

<210> SEQ ID NO 39
<211> LENGTH: 24
<212> TYPE: DNA
<213> ORGANISM: Artificial sequence
<220> FEATURE:
<223> OTHER INFORMATION: PCR primer

<400> SEQUENCE: 39
caacctgact tcggcgacat attg                                              24

<210> SEQ ID NO 40
<211> LENGTH: 24
<212> TYPE: DNA
<213> ORGANISM: Artificial sequence
<220> FEATURE:
<223> OTHER INFORMATION: PCR primer

<400> SEQUENCE: 40
caatatgtcg ccgaagtcag gttg                                              24

<210> SEQ ID NO 41
<211> LENGTH: 24
<212> TYPE: DNA
<213> ORGANISM: Artificial sequence
<220> FEATURE:
<223> OTHER INFORMATION: PCR primer

<400> SEQUENCE: 41
```

```
caacctgact tcgggcacat attg                                                  24
```

<210> SEQ ID NO 42
<211> LENGTH: 24
<212> TYPE: DNA
<213> ORGANISM: Artificial sequence
<220> FEATURE:
<223> OTHER INFORMATION: PCR primer

<400> SEQUENCE: 42

```
caatatgtgc ccgaagtcag gttg                                                  24
```

<210> SEQ ID NO 43
<211> LENGTH: 20
<212> TYPE: DNA
<213> ORGANISM: Artificial sequence
<220> FEATURE:
<223> OTHER INFORMATION: PCR primer

<400> SEQUENCE: 43

```
cgccgagccg cgtccgcacg                                                       20
```

<210> SEQ ID NO 44
<211> LENGTH: 20
<212> TYPE: DNA
<213> ORGANISM: Artificial sequence
<220> FEATURE:
<223> OTHER INFORMATION: PCR primer

<400> SEQUENCE: 44

```
cgtgcggacg cggctcggcg                                                       20
```

<210> SEQ ID NO 45
<211> LENGTH: 20
<212> TYPE: DNA
<213> ORGANISM: Artificial sequence
<220> FEATURE:
<223> OTHER INFORMATION: PCR primer

<400> SEQUENCE: 45

```
cgccgagcgc agtccgcacg                                                       20
```

<210> SEQ ID NO 46
<211> LENGTH: 20
<212> TYPE: DNA
<213> ORGANISM: Artificial sequence
<220> FEATURE:
<223> OTHER INFORMATION: PCR primer

<400> SEQUENCE: 46

```
cgtgcggact gcgctcggcg                                                       20
```

<210> SEQ ID NO 47
<211> LENGTH: 21
<212> TYPE: DNA
<213> ORGANISM: Artificial sequence
<220> FEATURE:
<223> OTHER INFORMATION: PCR primer

<400> SEQUENCE: 47

```
gcgtccgcga tgttcgacgt g                                                     21
```

<210> SEQ ID NO 48
<211> LENGTH: 21
<212> TYPE: DNA
<213> ORGANISM: Artificial sequence
<220> FEATURE:

<223> OTHER INFORMATION: PCR primer

<400> SEQUENCE: 48
cgaacatcgc ggacgctgca g        21

<210> SEQ ID NO 49
<211> LENGTH: 21
<212> TYPE: DNA
<213> ORGANISM: Artificial sequence
<220> FEATURE:
<223> OTHER INFORMATION: PCR primer

<400> SEQUENCE: 49
atttccgcga tgttcgacgt g        21

<210> SEQ ID NO 50
<211> LENGTH: 21
<212> TYPE: DNA
<213> ORGANISM: Artificial sequence
<220> FEATURE:
<223> OTHER INFORMATION: PCR primer

<400> SEQUENCE: 50
cgaacatcgc ggaaattgca g        21

<210> SEQ ID NO 51
<211> LENGTH: 23
<212> TYPE: DNA
<213> ORGANISM: Artificial sequence
<220> FEATURE:
<223> OTHER INFORMATION: PCR primer

<400> SEQUENCE: 51
gttcgacgtg gcgccaaaca tgc       23

<210> SEQ ID NO 52
<211> LENGTH: 23
<212> TYPE: DNA
<213> ORGANISM: Artificial sequence
<220> FEATURE:
<223> OTHER INFORMATION: PCR primer

<400> SEQUENCE: 52
gcatgtttgg cgccacgtcg aac       23

<210> SEQ ID NO 53
<211> LENGTH: 23
<212> TYPE: DNA
<213> ORGANISM: Artificial sequence
<220> FEATURE:
<223> OTHER INFORMATION: PCR primer

<400> SEQUENCE: 53
gttcgacgtg gtgccaaaca tgc       23

<210> SEQ ID NO 54
<211> LENGTH: 23
<212> TYPE: DNA
<213> ORGANISM: Artificial sequence
<220> FEATURE:
<223> OTHER INFORMATION: PCR primer

<400> SEQUENCE: 54
gcatgtttgg caccacgtcg aac       23

<210> SEQ ID NO 55

```
<211> LENGTH: 23
<212> TYPE: DNA
<213> ORGANISM: Artificial sequence
<220> FEATURE:
<223> OTHER INFORMATION: PCR primer

<400> SEQUENCE: 55
atggcggtgc ggtgagacac taa                                              23

<210> SEQ ID NO 56
<211> LENGTH: 23
<212> TYPE: DNA
<213> ORGANISM: Artificial sequence
<220> FEATURE:
<223> OTHER INFORMATION: PCR primer

<400> SEQUENCE: 56
ttagtgtctc accgcaccgc cat                                              23

<210> SEQ ID NO 57
<211> LENGTH: 23
<212> TYPE: DNA
<213> ORGANISM: Artificial sequence
<220> FEATURE:
<223> OTHER INFORMATION: PCR primer

<400> SEQUENCE: 57
atggcggtat tgtgagacac taa                                              23

<210> SEQ ID NO 58
<211> LENGTH: 23
<212> TYPE: DNA
<213> ORGANISM: Artificial sequence
<220> FEATURE:
<223> OTHER INFORMATION: PCR primer

<400> SEQUENCE: 58
ttagtgtctc acaataccgc cat                                              23

<210> SEQ ID NO 59
<211> LENGTH: 23
<212> TYPE: DNA
<213> ORGANISM: Artificial sequence
<220> FEATURE:
<223> OTHER INFORMATION: PCR primer

<400> SEQUENCE: 59
atggcggtgt ggtgagacac taa                                              23

<210> SEQ ID NO 60
<211> LENGTH: 23
<212> TYPE: DNA
<213> ORGANISM: Artificial sequence
<220> FEATURE:
<223> OTHER INFORMATION: PCR primer

<400> SEQUENCE: 60
ttagtgtctc accacaccgc cat                                              23

<210> SEQ ID NO 61
<211> LENGTH: 24
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (10)..(12)
```

<223> OTHER INFORMATION: n is a, c, g, or t

<400> SEQUENCE: 61
gcgtctgcan nntccgcgat gttc                                    24

<210> SEQ ID NO 62
<211> LENGTH: 24
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (14)..(16)
<223> OTHER INFORMATION: n is a, c, g, or t

<400> SEQUENCE: 62
cgaacatcgc ggannntgca gacg                                    24

<210> SEQ ID NO 63
<211> LENGTH: 21
<212> TYPE: DNA
<213> ORGANISM: Artificial sequence
<220> FEATURE:
<223> OTHER INFORMATION: PCR primer

<400> SEQUENCE: 63
cgtcgaagca cgcggacaat g                                       21

<210> SEQ ID NO 64
<211> LENGTH: 21
<212> TYPE: DNA
<213> ORGANISM: Artificial sequence
<220> FEATURE:
<223> OTHER INFORMATION: PCR primer

<400> SEQUENCE: 64
cgtcgaaata cgcggacaat g                                       21

<210> SEQ ID NO 65
<211> LENGTH: 21
<212> TYPE: DNA
<213> ORGANISM: Artificial sequence
<220> FEATURE:
<223> OTHER INFORMATION: PCR primer

<400> SEQUENCE: 65
gtccgcgtgg ttcgacgtgc t                                       21

<210> SEQ ID NO 66
<211> LENGTH: 21
<212> TYPE: DNA
<213> ORGANISM: Artificial sequence
<220> FEATURE:
<223> OTHER INFORMATION: PCR primer

<400> SEQUENCE: 66
cgtcgaacca cgcggacaat g                                       21

<210> SEQ ID NO 67
<211> LENGTH: 21
<212> TYPE: DNA
<213> ORGANISM: Artificial sequence
<220> FEATURE:
<223> OTHER INFORMATION: PCR primer

<400> SEQUENCE: 67

-continued gtccgcggtg ttcgacgtgc t                    21

<210> SEQ ID NO 68
<211> LENGTH: 21
<212> TYPE: DNA
<213> ORGANISM: Artificial sequence
<220> FEATURE:
<223> OTHER INFORMATION: PCR primer

<400> SEQUENCE: 68
cgtcgaacac cgcggacaat g                    21

<210> SEQ ID NO 69
<211> LENGTH: 21
<212> TYPE: DNA
<213> ORGANISM: Artificial sequence
<220> FEATURE:
<223> OTHER INFORMATION: PCR primer

<400> SEQUENCE: 69
gtccgcgacc ttcgacgtgc t                    21

<210> SEQ ID NO 70
<211> LENGTH: 21
<212> TYPE: DNA
<213> ORGANISM: Artificial sequence
<220> FEATURE:
<223> OTHER INFORMATION: PCR primer

<400> SEQUENCE: 70
cgtcgaaggt cgcggacaat g                    21

<210> SEQ ID NO 71
<211> LENGTH: 21
<212> TYPE: DNA
<213> ORGANISM: Artificial sequence
<220> FEATURE:
<223> OTHER INFORMATION: PCR primer

<400> SEQUENCE: 71
gtccgcgagc ttcgacgtgc t                    21

<210> SEQ ID NO 72
<211> LENGTH: 21
<212> TYPE: DNA
<213> ORGANISM: Artificial sequence
<220> FEATURE:
<223> OTHER INFORMATION: PCR primer

<400> SEQUENCE: 72
cgtcgaagct cgcggacaat g                    21

<210> SEQ ID NO 73
<211> LENGTH: 21
<212> TYPE: DNA
<213> ORGANISM: Artificial sequence
<220> FEATURE:
<223> OTHER INFORMATION: PCR primer

<400> SEQUENCE: 73
gtccgcgcgc ttcgacgtgc t                    21

<210> SEQ ID NO 74
<211> LENGTH: 21
<212> TYPE: DNA
<213> ORGANISM: Artificial sequence
<220> FEATURE:

```
<223> OTHER INFORMATION: PCR primer

<400> SEQUENCE: 74
cgtcgaagcg cgcggacaat g                                    21

<210> SEQ ID NO 75
<211> LENGTH: 21
<212> TYPE: DNA
<213> ORGANISM: Artificial sequence
<220> FEATURE:
<223> OTHER INFORMATION: PCR primer

<400> SEQUENCE: 75
gtccgcgcag ttcgacgtgc t                                    21

<210> SEQ ID NO 76
<211> LENGTH: 21
<212> TYPE: DNA
<213> ORGANISM: Artificial sequence
<220> FEATURE:
<223> OTHER INFORMATION: PCR primer

<400> SEQUENCE: 76
cgtcgaactg cgcggacaat g                                    21

<210> SEQ ID NO 77
<211> LENGTH: 21
<212> TYPE: DNA
<213> ORGANISM: Artificial sequence
<220> FEATURE:
<223> OTHER INFORMATION: PCR primer

<400> SEQUENCE: 77
gtccgcgccg ttcgacgtgc t                                    21

<210> SEQ ID NO 78
<211> LENGTH: 21
<212> TYPE: DNA
<213> ORGANISM: Artificial sequence
<220> FEATURE:
<223> OTHER INFORMATION: PCR primer

<400> SEQUENCE: 78
cgtcgaacgg cgcggacaat g                                    21

<210> SEQ ID NO 79
<211> LENGTH: 21
<212> TYPE: DNA
<213> ORGANISM: Artificial sequence
<220> FEATURE:
<223> OTHER INFORMATION: PCR primer

<400> SEQUENCE: 79
gtccgcgctg ttcgacgtgc t                                    21

<210> SEQ ID NO 80
<211> LENGTH: 21
<212> TYPE: DNA
<213> ORGANISM: Artificial sequence
<220> FEATURE:
<223> OTHER INFORMATION: PCR primer

<400> SEQUENCE: 80
cgtcgaacag cgcggacaat g                                    21

<210> SEQ ID NO 81
```

```
<211> LENGTH: 21
<212> TYPE: DNA
<213> ORGANISM: Artificial sequence
<220> FEATURE:
<223> OTHER INFORMATION: PCR primer

<400> SEQUENCE: 81
gtccgcgaaa ttcgacgtgc t                                              21

<210> SEQ ID NO 82
<211> LENGTH: 21
<212> TYPE: DNA
<213> ORGANISM: Artificial sequence
<220> FEATURE:
<223> OTHER INFORMATION: PCR primer

<400> SEQUENCE: 82
cgtcgaattt cgcggacaat g                                              21

<210> SEQ ID NO 83
<211> LENGTH: 21
<212> TYPE: DNA
<213> ORGANISM: Artificial sequence
<220> FEATURE:
<223> OTHER INFORMATION: PCR primer

<400> SEQUENCE: 83
gtccgcgatc ttcgacgtgc t                                              21

<210> SEQ ID NO 84
<211> LENGTH: 21
<212> TYPE: DNA
<213> ORGANISM: Artificial sequence
<220> FEATURE:
<223> OTHER INFORMATION: PCR primer

<400> SEQUENCE: 84
cgtcgaagat cgcggacaat g                                              21

<210> SEQ ID NO 85
<211> LENGTH: 21
<212> TYPE: DNA
<213> ORGANISM: Artificial sequence
<220> FEATURE:
<223> OTHER INFORMATION: PCR primer

<400> SEQUENCE: 85
gtccgcgcat ttcgacgtgc t                                              21

<210> SEQ ID NO 86
<211> LENGTH: 21
<212> TYPE: DNA
<213> ORGANISM: Artificial sequence
<220> FEATURE:
<223> OTHER INFORMATION: PCR primer

<400> SEQUENCE: 86
cgtcgaaatg cgcggacaat g                                              21

<210> SEQ ID NO 87
<211> LENGTH: 21
<212> TYPE: DNA
<213> ORGANISM: Artificial sequence
<220> FEATURE:
<223> OTHER INFORMATION: PCR primer

<400> SEQUENCE: 87
```
gtccgcgggc ttcgacgtgc t                                              21

<210> SEQ ID NO 88
<211> LENGTH: 21
<212> TYPE: DNA
<213> ORGANISM: Artificial sequence
<220> FEATURE:
<223> OTHER INFORMATION: PCR primer

<400> SEQUENCE: 88
cgtcgaagcc cgcggacaat g                                              21

<210> SEQ ID NO 89
<211> LENGTH: 21
<212> TYPE: DNA
<213> ORGANISM: Artificial sequence
<220> FEATURE:
<223> OTHER INFORMATION: PCR primer

<400> SEQUENCE: 89
gtccgcgttc ttcgacgtgc t                                              21

<210> SEQ ID NO 90
<211> LENGTH: 21
<212> TYPE: DNA
<213> ORGANISM: Artificial sequence
<220> FEATURE:
<223> OTHER INFORMATION: PCR primer

<400> SEQUENCE: 90
cgtcgaagaa cgcggacaat g                                              21

<210> SEQ ID NO 91
<211> LENGTH: 21
<212> TYPE: DNA
<213> ORGANISM: Artificial sequence
<220> FEATURE:
<223> OTHER INFORMATION: PCR primer

<400> SEQUENCE: 91
gtccgcggaa ttcgacgtgc t                                              21

<210> SEQ ID NO 92
<211> LENGTH: 21
<212> TYPE: DNA
<213> ORGANISM: Artificial sequence
<220> FEATURE:
<223> OTHER INFORMATION: PCR primer

<400> SEQUENCE: 92
cgtcgaattc cgcggacaat g                                              21

<210> SEQ ID NO 93
<211> LENGTH: 21
<212> TYPE: DNA
<213> ORGANISM: Artificial sequence
<220> FEATURE:
<223> OTHER INFORMATION: PCR primer

<400> SEQUENCE: 93
gtccgcggat ttcgacgtgc t                                              21

<210> SEQ ID NO 94
<211> LENGTH: 21
<212> TYPE: DNA
<213> ORGANISM: Artificial sequence
<220> FEATURE:

-continued

```
<223> OTHER INFORMATION: PCR primer

<400> SEQUENCE: 94
cgtcgaaatc cgcggacaat g                                              21

<210> SEQ ID NO 95
<211> LENGTH: 21
<212> TYPE: DNA
<213> ORGANISM: Artificial sequence
<220> FEATURE:
<223> OTHER INFORMATION: PCR primer

<400> SEQUENCE: 95
gtccgcgtgc ttcgacgtgc t                                              21

<210> SEQ ID NO 96
<211> LENGTH: 21
<212> TYPE: DNA
<213> ORGANISM: Artificial sequence
<220> FEATURE:
<223> OTHER INFORMATION: PCR primer

<400> SEQUENCE: 96
gtccgcgtat ttcgacgtgc t                                              21

<210> SEQ ID NO 97
<211> LENGTH: 21
<212> TYPE: DNA
<213> ORGANISM: Artificial sequence
<220> FEATURE:
<223> OTHER INFORMATION: PCR primer

<400> SEQUENCE: 97
gtccgcgaac ttcgacgtgc t                                              21

<210> SEQ ID NO 98
<211> LENGTH: 21
<212> TYPE: DNA
<213> ORGANISM: Artificial sequence
<220> FEATURE:
<223> OTHER INFORMATION: PCR primer

<400> SEQUENCE: 98
cgtcgaagtt cgcggacaat g                                              21

<210> SEQ ID NO 99
<211> LENGTH: 21
<212> TYPE: DNA
<213> ORGANISM: Artificial sequence
<220> FEATURE:
<223> OTHER INFORMATION: PCR primer

<400> SEQUENCE: 99
gtccgcggcg ttcgacgtgc t                                              21

<210> SEQ ID NO 100
<211> LENGTH: 21
<212> TYPE: DNA
<213> ORGANISM: Artificial sequence
<220> FEATURE:
<223> OTHER INFORMATION: PCR primer

<400> SEQUENCE: 100
cgtcgaacgc cgcggacaat g                                              21

<210> SEQ ID NO 101
```

```
<211> LENGTH: 23
<212> TYPE: DNA
<213> ORGANISM: Artificial sequence
<220> FEATURE:
<223> OTHER INFORMATION: PCR primer

<400> SEQUENCE: 101
gtccgcgatg tatgacgtgc tgc                                              23

<210> SEQ ID NO 102
<211> LENGTH: 23
<212> TYPE: DNA
<213> ORGANISM: Artificial sequence
<220> FEATURE:
<223> OTHER INFORMATION: PCR primer

<400> SEQUENCE: 102
gcagcacgtc atacatcgcg gac                                              23

<210> SEQ ID NO 103
<211> LENGTH: 23
<212> TYPE: DNA
<213> ORGANISM: Artificial sequence
<220> FEATURE:
<223> OTHER INFORMATION: PCR primer

<400> SEQUENCE: 103
gtccgcgatg tgggacgtgc tgc                                              23

<210> SEQ ID NO 104
<211> LENGTH: 23
<212> TYPE: DNA
<213> ORGANISM: Artificial sequence
<220> FEATURE:
<223> OTHER INFORMATION: PCR primer

<400> SEQUENCE: 104
gcagcacgtc ccacatcgcg gac                                              23

<210> SEQ ID NO 105
<211> LENGTH: 23
<212> TYPE: DNA
<213> ORGANISM: Artificial sequence
<220> FEATURE:
<223> OTHER INFORMATION: PCR primer

<400> SEQUENCE: 105
gtccgcgatg actgacgtgc tgc                                              23

<210> SEQ ID NO 106
<211> LENGTH: 23
<212> TYPE: DNA
<213> ORGANISM: Artificial sequence
<220> FEATURE:
<223> OTHER INFORMATION: PCR primer

<400> SEQUENCE: 106
gcagcacgtc agtcatcgcg gac                                              23

<210> SEQ ID NO 107
<211> LENGTH: 23
<212> TYPE: DNA
<213> ORGANISM: Artificial sequence
<220> FEATURE:
<223> OTHER INFORMATION: PCR primer

<400> SEQUENCE: 107
```
gtccgcgatg tcggacgtgc tgc                                              23

<210> SEQ ID NO 108
<211> LENGTH: 23
<212> TYPE: DNA
<213> ORGANISM: Artificial sequence
<220> FEATURE:
<223> OTHER INFORMATION: PCR primer

<400> SEQUENCE: 108
gcagcacgtc cgacatcgcg gac                                              23

<210> SEQ ID NO 109
<211> LENGTH: 23
<212> TYPE: DNA
<213> ORGANISM: Artificial sequence
<220> FEATURE:
<223> OTHER INFORMATION: PCR primer

<400> SEQUENCE: 109
gtccgcgatg cgtgacgtgc tgc                                              23

<210> SEQ ID NO 110
<211> LENGTH: 23
<212> TYPE: DNA
<213> ORGANISM: Artificial sequence
<220> FEATURE:
<223> OTHER INFORMATION: PCR primer

<400> SEQUENCE: 110
gcagcacgtc acgcatcgcg gac                                              23

<210> SEQ ID NO 111
<211> LENGTH: 23
<212> TYPE: DNA
<213> ORGANISM: Artificial sequence
<220> FEATURE:
<223> OTHER INFORMATION: PCR primer

<400> SEQUENCE: 111
gtccgcgatg caggacgtgc tgc                                              23

<210> SEQ ID NO 112
<211> LENGTH: 23
<212> TYPE: DNA
<213> ORGANISM: Artificial sequence
<220> FEATURE:
<223> OTHER INFORMATION: PCR primer

<400> SEQUENCE: 112
gcagcacgtc ctgcatcgcg gac                                              23

<210> SEQ ID NO 113
<211> LENGTH: 23
<212> TYPE: DNA
<213> ORGANISM: Artificial sequence
<220> FEATURE:
<223> OTHER INFORMATION: PCR primer

<400> SEQUENCE: 113
gtccgcgatg ccggacgtgc tgc                                              23

<210> SEQ ID NO 114
<211> LENGTH: 23
<212> TYPE: DNA
<213> ORGANISM: Artificial sequence
<220> FEATURE:

<223> OTHER INFORMATION: PCR primer

<400> SEQUENCE: 114
gcagcacgtc cggcatcgcg gac                                      23

<210> SEQ ID NO 115
<211> LENGTH: 23
<212> TYPE: DNA
<213> ORGANISM: Artificial sequence
<220> FEATURE:
<223> OTHER INFORMATION: PCR primer

<400> SEQUENCE: 115
gtccgcgatg aacgacgtgc tgc                                      23

<210> SEQ ID NO 116
<211> LENGTH: 23
<212> TYPE: DNA
<213> ORGANISM: Artificial sequence
<220> FEATURE:
<223> OTHER INFORMATION: PCR primer

<400> SEQUENCE: 116
gcagcacgtc gttcatcgcg gac                                      23

<210> SEQ ID NO 117
<211> LENGTH: 23
<212> TYPE: DNA
<213> ORGANISM: Artificial sequence
<220> FEATURE:
<223> OTHER INFORMATION: PCR primer

<400> SEQUENCE: 117
gtccgcgatg atggacgtgc tgc                                      23

<210> SEQ ID NO 118
<211> LENGTH: 23
<212> TYPE: DNA
<213> ORGANISM: Artificial sequence
<220> FEATURE:
<223> OTHER INFORMATION: PCR primer

<400> SEQUENCE: 118
gcagcacgtc catcatcgcg gac                                      23

<210> SEQ ID NO 119
<211> LENGTH: 23
<212> TYPE: DNA
<213> ORGANISM: Artificial sequence
<220> FEATURE:
<223> OTHER INFORMATION: PCR primer

<400> SEQUENCE: 119
gtccgcgatg ctagacgtgc tgc                                      23

<210> SEQ ID NO 120
<211> LENGTH: 23
<212> TYPE: DNA
<213> ORGANISM: Artificial sequence
<220> FEATURE:
<223> OTHER INFORMATION: PCR primer

<400> SEQUENCE: 120
gcagcacgtc tagcatcgcg gac                                      23

<210> SEQ ID NO 121

<211> LENGTH: 23
<212> TYPE: DNA
<213> ORGANISM: Artificial sequence
<220> FEATURE:
<223> OTHER INFORMATION: PCR primer

<400> SEQUENCE: 121
gtccgcgatg aaggacgtgc tgc    23

<210> SEQ ID NO 122
<211> LENGTH: 23
<212> TYPE: DNA
<213> ORGANISM: Artificial sequence
<220> FEATURE:
<223> OTHER INFORMATION: PCR primer

<400> SEQUENCE: 122
gcagcacgtc cttcatcgcg gac    23

<210> SEQ ID NO 123
<211> LENGTH: 23
<212> TYPE: DNA
<213> ORGANISM: Artificial sequence
<220> FEATURE:
<223> OTHER INFORMATION: PCR primer

<400> SEQUENCE: 123
gtccgcgatg atcgacgtgc tgc    23

<210> SEQ ID NO 124
<211> LENGTH: 23
<212> TYPE: DNA
<213> ORGANISM: Artificial sequence
<220> FEATURE:
<223> OTHER INFORMATION: PCR primer

<400> SEQUENCE: 124
gcagcacgtc gatcatcgcg gac    23

<210> SEQ ID NO 125
<211> LENGTH: 23
<212> TYPE: DNA
<213> ORGANISM: Artificial sequence
<220> FEATURE:
<223> OTHER INFORMATION: PCR primer

<400> SEQUENCE: 125
gtccgcgatg catgacgtgc tgc    23

<210> SEQ ID NO 126
<211> LENGTH: 23
<212> TYPE: DNA
<213> ORGANISM: Artificial sequence
<220> FEATURE:
<223> OTHER INFORMATION: PCR primer

<400> SEQUENCE: 126
gcagcacgtc atgcatcgcg gac    23

<210> SEQ ID NO 127
<211> LENGTH: 23
<212> TYPE: DNA
<213> ORGANISM: Artificial sequence
<220> FEATURE:
<223> OTHER INFORMATION: PCR primer

<400> SEQUENCE: 127
gtccgcgatg gcggacgtgc tgc                                    23

<210> SEQ ID NO 128
<211> LENGTH: 23
<212> TYPE: DNA
<213> ORGANISM: Artificial sequence
<220> FEATURE:
<223> OTHER INFORMATION: PCR primer

<400> SEQUENCE: 128
gcagcacgtc cgccatcgcg gac                                    23

<210> SEQ ID NO 129
<211> LENGTH: 23
<212> TYPE: DNA
<213> ORGANISM: Artificial sequence
<220> FEATURE:
<223> OTHER INFORMATION: PCR primer

<400> SEQUENCE: 129
gtccgcgatg gaagacgtgc tgc                                    23

<210> SEQ ID NO 130
<211> LENGTH: 23
<212> TYPE: DNA
<213> ORGANISM: Artificial sequence
<220> FEATURE:
<223> OTHER INFORMATION: PCR primer

<400> SEQUENCE: 130
gcagcacgtc ttccatcgcg gac                                    23

<210> SEQ ID NO 131
<211> LENGTH: 23
<212> TYPE: DNA
<213> ORGANISM: Artificial sequence
<220> FEATURE:
<223> OTHER INFORMATION: PCR primer

<400> SEQUENCE: 131
gtccgcgatg gacgacgtgc tgc                                    23

<210> SEQ ID NO 132
<211> LENGTH: 23
<212> TYPE: DNA
<213> ORGANISM: Artificial sequence
<220> FEATURE:
<223> OTHER INFORMATION: PCR primer

<400> SEQUENCE: 132
gcagcacgtc gtccatcgcg gac                                    23

<210> SEQ ID NO 133
<211> LENGTH: 23
<212> TYPE: DNA
<213> ORGANISM: Artificial sequence
<220> FEATURE:
<223> OTHER INFORMATION: PCR primer

<400> SEQUENCE: 133
gtccgcgatg tgcgacgtgc tgc                                    23

<210> SEQ ID NO 134
<211> LENGTH: 23
<212> TYPE: DNA
<213> ORGANISM: Artificial sequence
<220> FEATURE:

<223> OTHER INFORMATION: PCR primer

<400> SEQUENCE: 134
gcagcacgtc gcacatcgcg gac                                             23

<210> SEQ ID NO 135
<211> LENGTH: 23
<212> TYPE: DNA
<213> ORGANISM: Artificial sequence
<220> FEATURE:
<223> OTHER INFORMATION: PCR primer

<400> SEQUENCE: 135
gtccgcgatg ggcgacgtgc tgc                                             23

<210> SEQ ID NO 136
<211> LENGTH: 23
<212> TYPE: DNA
<213> ORGANISM: Artificial sequence
<220> FEATURE:
<223> OTHER INFORMATION: PCR primer

<400> SEQUENCE: 136
gcagcacgtc gcccatcgcg gac                                             23

<210> SEQ ID NO 137
<211> LENGTH: 23
<212> TYPE: DNA
<213> ORGANISM: Artificial sequence
<220> FEATURE:
<223> OTHER INFORMATION: PCR primer

<400> SEQUENCE: 137
gtccgcgatg gtggacgtgc tgc                                             23

<210> SEQ ID NO 138
<211> LENGTH: 23
<212> TYPE: DNA
<213> ORGANISM: Artificial sequence
<220> FEATURE:
<223> OTHER INFORMATION: PCR primer

<400> SEQUENCE: 138
gcagcacgtc caccatcgcg gac                                             23

<210> SEQ ID NO 139
<211> LENGTH: 11
<212> TYPE: PRT
<213> ORGANISM: Artificial Sequence
<220> FEATURE:
<223> OTHER INFORMATION: modified loop 2
<220> FEATURE:
<221> NAME/KEY: misc_feature
<222> LOCATION: (5)..(5)
<223> OTHER INFORMATION: Xaa can be any amino acid
<220> FEATURE:
<221> NAME/KEY: misc_feature
<222> LOCATION: (7)..(7)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa can be any amino acid

<400> SEQUENCE: 139

Thr Thr Tyr Trp Xaa Lys Xaa Glu Ala Xaa Thr
1               5                   10

```
<210> SEQ ID NO 140
<211> LENGTH: 22
<212> TYPE: PRT
<213> ORGANISM: Artificial Sequence
<220> FEATURE:
<223> OTHER INFORMATION: modified helix alpha FG1
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (11)..(12)
<223> OTHER INFORMATION: Xaa can be any amino acid
<220> FEATURE:
<221> NAME/KEY: misc_feature
<222> LOCATION: (15)..(15)
<223> OTHER INFORMATION: Xaa can be any amino acid

<400> SEQUENCE: 140

Ala Thr Xaa Glu Ala Ser Ala Xaa Ser Ala Xaa Xaa Asp Val Xaa Pro
1               5                   10                  15

Asn Met Leu Gln Ala Ile
            20
```

BIOCATALYSTS FOR MANUFACTURING DULOXETINE ALCOHOL

RELATED APPLICATIONS

This application is a national stage application (under 35 U.S.C. §371) of PCT/EP2009/067341, filed Dec. 16, 2009, which claims benefit of European application 08172003.9, filed Dec. 17, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13111_00178_US. The size of the text file is 38 KB, and the text file was created on Jun. 15, 2011.

The present invention relates to new types of phenylethanol dehydrogenase mutants, processes for their production; nucleic acid sequences coding for them, expression cassettes, vectors and recombinant microorganisms which comprise these sequences; processes for the biocatalytic synthesis of substituted, optically active alcohols using these mutants; and in particular a process for the preparation of duloxetine alcohol or duloxetine, comprising a biocatalytic synthesis step catalyzed by these mutants.

BACKGROUND TO THE INVENTION

Duloxetine alcohol (3) is an important precursor in the preparation of duloxetine (4) (cf. scheme 1), which is sold under the trade name Cymbalta® inter alia as an antidepressant.

Scheme 1: preparation of duloxetine via duloxetine alcohol

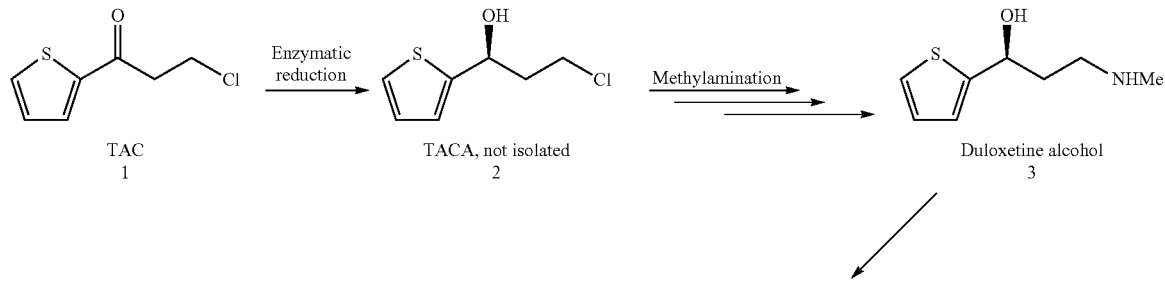

TAC
1

TACA, not isolated
2

Duloxetine alcohol
3

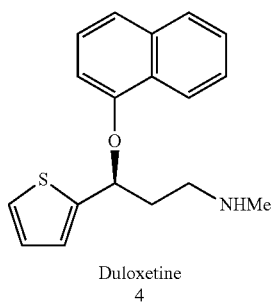

Duloxetine
4

The intermediate (TACA) (2) that arises can be prepared with the help of a dehydrogenase (cf. WO2005/033094). For example, the phenylethanol dehydrogenase EbN1 from *Azoarcus* sp. (newer name *Aromatoleum aromaticum*) (cf. Höffken et al., Biochemistry, vol. 45, No. 1, 2006) reduces the chloroketone 3-chloro-1-(thienyl-2-yl)-propan-1-one (1) to the corresponding chloroalcohol (1S)-3-chloro-1-(thienyl-2-yl)-propan-1-ol (2), analogously to a Meerwein-Ponndorf reduction. For this, the dehydrogenase requires the cofactor nicotinamide-adenine dinucleotide (NADH), which produces the necessary reduction equivalents. This expensive cofactor can be regenerated with the help of a secondary "sacrificial alcohol" (e.g. 2-propanol or 2-butanol), during which the corresponding ketone (e.g. acetone or 2-butanone) is formed. Relatively long-chain alcohols are preferred by the enzyme here, but are also considerably more expensive. For this reason, 2-butanol is used as sacrificial alcohol (cf. scheme 2) (cf. also WO2006/072465).

Scheme 2: regeneration of the cofactor NADH with the help of a "sacrificial alcohol"

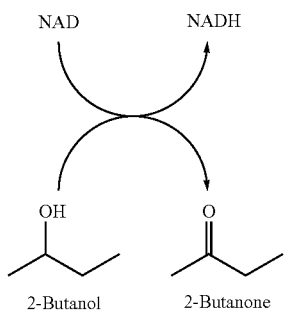

The wild-type enzyme EbN1 and expression systems that can be used for its expression are described in WO2005/108590 and WO2006/094945.

BRIEF DESCRIPTION OF THE INVENTION

It was an object of the invention to increase the activity of biocatalysts which can be used for the preparation of duloxetine.

In particular, the aim was to provide biocatalysts which improve the enzymatic reduction of TAC (1) to TACA (2). The improvement to be attained here can consist in:
  higher reaction rate
  higher product yield
  lower susceptibility to product inhibition
  improvement in the cofactor regeneration
  combinations thereof.

Surprisingly, this object was achieved through the provision of special mutants of the above-described phenyl alcohol dehydrogenase EbN1 from *Azoarcus* sp.

In particular, the above object was surprisingly achieved in two different ways. According to the first solution route, the sequence of the gene coding for the biocatalyst was mutated by chance by error-prone polymerase chain reaction (error-prone PCR) and thus generates a large number of variants from which improved mutants could be selected. These in turn were mutated again for further improvement (directed evolution).

Another solution route consisted in carrying out saturation mutageneses in a targeted manner at selected sequence positions. Firstly, starting from the crystal structure of the dehydrogenase (Höffken et al., Biochemistry, vol. 45, No. 1, 2006), target positions for suitable mutations were determined by "rational design". Saturation mutageneses were then carried out at these positions.

DESCRIPTION OF THE FIGURES

FIG. 1 shows the coding nucleic acid sequence (A) and the amino acid sequence (B) of the phenylethanol dehydrogenase EbN1.

FIG. 3 shows diagrammatically the cloning strategy for various mutants.

DETAILED DESCRIPTION OF THE INVENTION

1. Definition of General Terms

Figure 2:
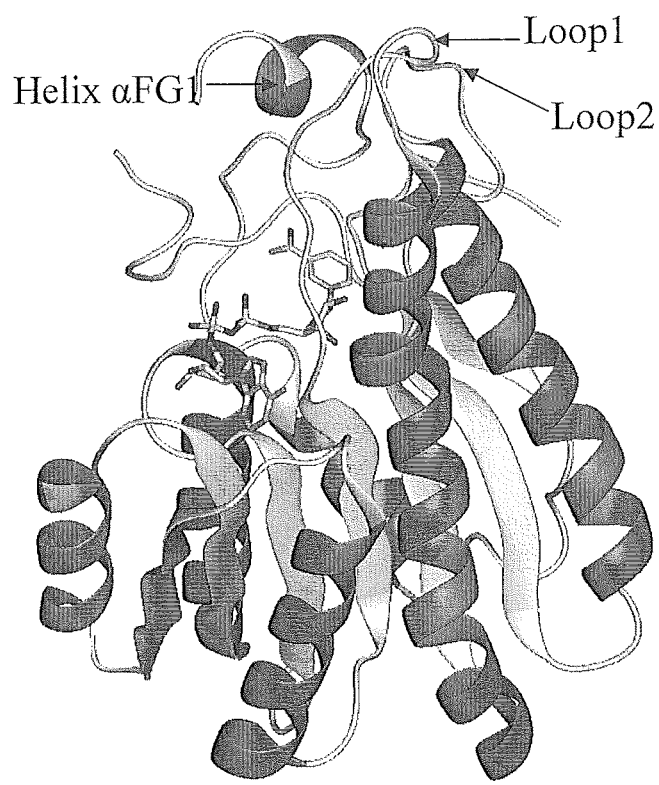
FIG. 2 shows the band model of one monomer of EbN1.

"Phenylethanol dehydrogenases" (EC No. 1.1.1) are generally enzymes which catalyze the NADH dependent, stereospecific reduction of acetophenone to S-1-phenylethanol. A "phenylethanol dehydrogenase" or an "enzyme with phenylethanol dehydrogenase activity" within the context of the invention catalyzes in particular the enzymatic synthesis of optically active alcohols of the general formula II, starting from the ketone of the formula I, and in particular the stereospecific equilibrium reaction between 3-chloro-1-(thienyl-2-yl)-propan-1-one and (1S)-3-chloro-1-(thienyl-2-yl)-propan-1-ol.

On account of the reversibility of enzymatic reactions, the present invention relates to the enzymatic reactions described herein in both reaction directions (i.e. with formation or consumption of reduction equivalents).

"Functional mutants" of a "phenylethanol dehydrogenase" comprise the "functional equivalents" of such enzymes defined below.

The term "biocatalytic process" refers to any process carried out in the presence of catalytic activity of a "phenylethanol dehydrogenase" according to the invention or of an enzyme with "phenylethanol dehydrogenase activity", i.e. processes in the presence of crude, or purified, dissolved, dispersed or immobilized enzyme, or in the presence of whole microbial cells which have or express such enzyme activity. Biocatalytic processes thus comprise enzymatic processes and microbial processes.

The term "stereospecific" means that one of several possible stereoisomers of a compound prepared according to the invention with at least one asymmetrical center is produced by the effect of an enzyme according to the invention in a high "enantiomer excess" or high "enantiomer purity", such as, for example, at least 90% ee, in particular at least 95% ee, or at least 98% ee, or at least 99% ee. The ee % value is calculated according to the following formula:

$$ee \% = [X_A - X_B]/[X_A + X_B] * 100,$$

in which $X_A$ and $X_B$ are the molar fraction of the enantiomers A or B, respectively.

Furthermore, the following abbreviations are used herein
TAC=3-chloro-1-thiophen-2-yl-propan-1-one
TACA=3-chloro-1-thiophen-2-yl-propan-1-ol
TA=1-thiophen-2-yl-propenone
TAA=1-thiophen-2-yl-prop-2-en-1-ol A "lower alcohol" is in particular a monool and comprises according to the invention a lower alkyl radical. This is in particular $C_1$-$C_8$-alkyl radicals, in particular $C_1$-$C_6$-alkyl radicals, which are branched or in particular linear and have 1 to 8, in particular 1, 2, 3, 4, 5 or 6 carbon atoms. Examples are $C_1$-$C_4$-alkyl radicals, such as methyl, ethyl, n-propyl, isopropyl, n-butyl, 2-butyl, isobutyl or tert-butyl; and additionally radicals with more than 4 carbon atoms, such as pentyl, 1-methylbutyl, 2-methylbutyl, 3-methylbutyl, 2,2-dimethylpropyl, 1-ethylpropyl, 1,1-dimethylpropyl, 1,2-dimethylpropyl, 1-methyl-pentyl, 2-methyl pentyl, 3-methylpentyl, 4-methylpentyl, n-hexyl, 1,1-dimethylbutyl, 1,2-dimethylbutyl, 1,3-dimethylbutyl, 2,2-dimethylbutyl, 2,3-dimethylbutyl and 3,3-dimethylbutyl.

"Cyclic rings" (Cyc) comprise a mono- or polynuclear, saturated or unsaturated, carboxylic or heterocyclic, aromatic or nonaromatic, optionally mono- or polysubstituted ring.

Examples of carbocyclic and heterocyclic groups Cyc are in particular mono- or dinuclear, preferably mononuclear, groups having up to 4, such as, for example, 0, 1 or 2, identical or different ring heteroatoms, selected from O, N and S.

These carbocyclic or heterocyclic rings comprise in particular 3 to 12, preferably 4, 5 or 6 ring carbon atoms. Examples which may be mentioned are cyclopropyl, cyclobutyl, cyclopentyl, cyclohexyl, cycloheptyl, the mono- or polyunsaturated analogs thereof, such as cyclobutenyl, cyclopentenyl, cyclopentadienyl, cyclohexenyl, cycloheptenyl, cyclohexadienyl, cycloheptadienyl, and phenyl; and 5- to 7-membered saturated or mono- or polyunsaturated heterocyclic radicals having 1 to 4 heteroatoms which are selected form O, N and S. In particular, mention is to be made of heterocyclic radicals derived from pyrrolidone, tetrahydrofuran, piperidine, morpholine, pyrrole, furan, thiophene, pyrazole, imidazole, oxazole, thiazole, pyridine, pyran, pyrimidine, pyridazine and pyrazine.

Mention is also to be made of dinuclear radicals in which one of the aforementioned carbocycles or heterocycles has been condensed with a further heterocycle or carbocycle, such as, for example, radicals derived from coumaron, indole, quinoline and naphthalene.

A further preferred group of Cyc radicals are aryl radicals. "Aryl" is a mono- or polynuclear, preferably mono- or dinuclear, optionally substituted aromatic radical, in particular phenyl or a naphthyl bonded via any desired ring position, such as 1- or 2-naphthyl.

The radicals Cyc may here be bonded via any desired ring position, preferably via a ring carbon atom.

Examples of suitable Cyc radicals are phenyl, naphthyl, 2-thienyl, 3-thienyl; 2-furanyl, 3-furanyl; 2-pyridyl, 3-pyridyl or 4-pyridyl; 2-thiazolyl, 4-thiazolyl or 5-thiazolyl; 4-methyl-2-thienyl, 3-ethyl-2-thienyl, 2-methyl-3-thienyl, 4-propyl-3-thienyl, 5-n-butyl-2-thienyl, 4-methyl-3-thienyl, 3-methyl-2-thienyl; 3-chloro-2-thienyl, 4-bromo-3-thienyl, 2-iodo-3-thienyl, 5-iodo-3-thienyl, 4-fluoro-2-thienyl, 2-bromo-3-thienyl, and 4-chloro-2-thienyl.

The radicals Cyc may also be substituted one or more times, such as, for example, monosubstituted or disubstituted. Preferably, the substituents sit on a ring carbon atom. Examples of suitable substituents are halogen, lower alkyl, lower alkenyl, lower alkoxy, —OH, —SH, —NO$_2$ or NR$^2$R$^3$, where R$^2$ and R$^3$, independently of one another, are H, methyl or ethyl.

"Halogen" is fluorine, chlorine, bromine or iodine, in particular fluorine or chlorine.

"Lower alkyl" is preferably straight-chain or branched alkyl radicals having 2 to 8, in particular 2 to 6, carbon atoms, such as ethyl, isopropyl or n-propyl, n-butyl, isobutyl, sec-butyl or tert-butyl, n-pentyl or 2-methylbutyl, n-hexyl, 2-methylpentyl, 3-methylpentyl, 2-ethylbutyl.

"Lower alkoxy" is preferably the corresponding oxygen-terminated analogs of the above lower alkyl radicals.

"Lower alkenyl" is the mono- or polyunsaturated, preferably monounsaturated, analogs of the aforementioned alkyl radicals having 2 to 8, in particular 2 to 6, carbon atoms, where the double bond may be in any desired position on the carbon chain.

2. Preferred Embodiments of the Invention

The invention firstly provides functional phenylethanol dehydrogenase mutants derived from the phenylethanol dehydrogenase EbN1 from *Azoarcus* sp. with an amino acid sequence according to SEQ ID NO: 2.

In particular, the invention relates to functional phenylethanol dehydrogenase mutants derived from the phenylethanol dehydrogenase EbN1 from *Azoarcus* sp. with an amino acid sequence according to SEQ ID NO: 2, where the mutants have at least one mutation in at least one sequence region selected from
(1) sequence region 142 to 153 (also referred to as loop 2) and
(2) sequence region 190 to 211 (also referred to as helix alpha FG1).

In particular, the invention relates to functional phenylethanol dehydrogenase mutants which additionally have at least one further mutation in a further sequence region selected from
(3) sequence region 93 to 96 (also referred to as loop 1)
(4) sequence region 241 to 249 (C terminus)
(5) sequence region 138 to 141 (hydrophilic region of binding pocket, also referred to as loop 2) and
(6) Cys61 and/or Cys 83.

Furthermore, the invention relates to functional phenylethanol dehydrogenase mutants derived from the phenylethanol dehydrogenase EbN1 from *Azoarcus* sp. with an amino acid sequence according to SEQ ID NO: 2, where the mutant is selected from the mutants listed in table 1.

In particular, mention is to be made of mutants where at least one of the following radicals is mutated:
T192, L197, M200, F201, L204, M246, L139, T140, T142, L146, I148, Y151, C61, C83, L186, the respective amino acid being replaced by any desired other natural amino acid.

In particular, mutants according to the invention are selected from mutants comprising at least one of the following mutations:
a) single mutations:
$Y151X_A$, where $X_A$=A, R, N, E, Q, G, H, I, L, M, T or V;
$T192X_B$, where $X_B$=A, E, G, I, P, S, W, V or L;
b) multiple mutations:
$Y151X_A T192X_B$, where $X_A$ and $X_B$ have the meanings given above.

The invention provides in particular mutants which are characterized by at least one of the following modified part sequences:
(part sequence 1) 142-TTYWX$_1$KX$_2$EAX$_3$T-153 (modified loop 2) and
(part sequence 2) 190-ATX$_4$EASAX$_5$SAX$_6$X$_7$DVX$_8$PNMLQAI-211 (modified helix alpha FG1)
in which $X_1$ to $X_8$, independently of one another, are any desired amino acid radicals, where at least one of the radicals $X_1$ to $X_3$ and $X_4$ to $X_8$ is not a natural amino acid radical of the native enzyme according to SEQ ID NO:2, where in particular $X_1$ is L or is substituted by I, V, A, M, F or H.
$X_2$ is I or is substituted by L, V, A, M, F or H.
$X_3$ is Y or is substituted by A, R, N, E, Q, G, H, I, L, M, T or V;
or in which
$X_4$ is T or is substituted by A, E, G, I, P, S, W, V or L
$X_5$ is L or is substituted by I, V, A, M, F or H.
$X_6$ is M or is substituted by Y, W, E, V, S, R, Q, K, I, H, G, F, E or D
$X_7$ is F or is substituted by G, K, T, Y, M, W or R
$X_8$ is L or is substituted by I, V, A, M, F or H.

The invention also relates in particular to those mutants which still have at least about 50% of the enzymatic activity of the dehydrogenase with SEQ ID NO:2, such as, for example, those with 50 to 100% or more than 100%, such as, for example >100 to 1000%, in each case determined under standard conditions using a reference substance, such as TAC or TACA (compare below, details relating to the determination of the phenylethanol dehydrogenase activity).

In particular, the invention also provides those mutants which have a percentage sequence identity to SEQ ID NO: 2 of at least about 70%, such as, for example, 70 to 99.9%, 75 to 99.9%, 80 to 99.9%, 85 to 99.9%, 90 to 99.9% or 95 to 99.9%.

In particular, the invention also provides those mutants in which, in addition to at least one mutation in the above-defined regions (1) to (6), up to 25% of the amino acid radicals outside of these regions have been modified compared with SEQ ID NO: 2 through addition, deletion, insertion, substitution, inversion or a combination thereof.

In particular, the invention provides those mutants which catalyze the stereospecific equilibrium reaction between 3-chloro-1-(thienyl-2-yl)-propan-1-one (1) and (1S)-3-chloro-1-(thienyl-2-yl)-propan-1-ol (2)

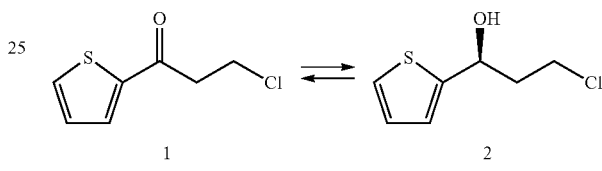

in the presence of the cofactor NAD$^+$ or NADH.

The invention further provides nucleic acid sequences coding for a mutant defined herein.

The invention further provides expression cassettes comprising at least one nucleic acid sequence defined herein, functionally linked to at least one regulatory nucleic acid sequence.

The invention further provides vectors comprising at least one expression cassette defined herein.

The invention further provides recombinant microorganisms comprising at least one nucleic acid defined herein, one expression cassette defined herein or one vector defined herein.

The invention further provides processes for producing a phenylethanol dehydrogenase mutant defined herein, which comprises cultivating a recombinant microorganism defined herein, expressing the nucleic acid sequence coding for the mutant and optionally isolating the expression product.

The invention further provides a process for the microbial/enzymatic synthesis of substituted, optically active alcohols of the formula (II)

(II)

in which

Cyc is a mono- or polynuclear, saturated or unsaturated, carbocyclic or heterocyclic, optionally mono- or polysubstituted ring, in each case in stereoisomerically pure form or as a mixture of stereoisomers, comprising the biocatalytic (microbial/enzymatic) reduction of a ketone of the formula (I)

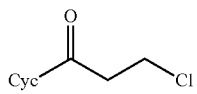
(I)

in the presence of a phenylethanol dehydrogenase mutant defined herein, optionally with the addition of reduction equivalents, such as in particular NADH.

Also provided are in particular those processes where the reaction takes place under conditions of reduction equivalent regeneration, using a lower alcohol, such as, in particular, a $C_1$ to $C_6$-monoalcohol, as sacrificial alcohol.

Using the preparation process according to the invention, in particular those compounds of the formula (I) are reacted where Cyc is a heterocyclic radical, in particular a thienyl radical.

Also provided are in particular those processes giving an essentially enantiomerically pure alcohol of the formula (II), in particular the (S)-enantiomer.

Also provided are in particular those processes where the mutant is used in isolated form and thereby optionally immobilized on a solid support; or expressed in microbial cells which are optionally immobilized on a solid support. Suitable solid supports, such as, for example, polymeric support materials, such as beads or membranes, are known to the person skilled in the art in the field of biotransformation and enzyme reactor technology.

Also provided are in particular processes for the preparation of duloxetine, comprising a) the microbial/enzymatic reduction of 3-chloro-1-(thienyl-2-yl)-propan-1-one (1) to (1S)-3-chloro-1-(thienyl-2-yl)-propan-1-ol (2)

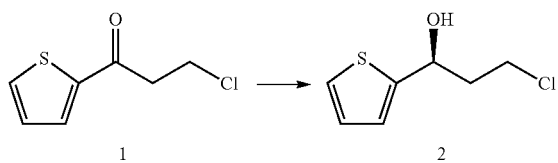 [SMILES: O=C(CCCl)c1cccs1 ; O[C@@H](CCCl)c1cccs1]

using a biocatalytic process as defined herein;

b) the chemical conversion of the alcohol (2) by methylamination to give duloxetine alcohol (3)

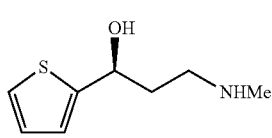
3 and finally c) the chemical conversion of the duloxetine alcohol (3) by inserting a naphthyl group to give duloxetine (4).

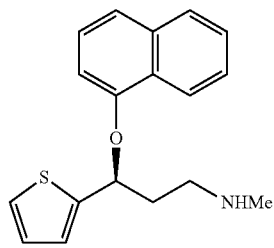
4

Furthermore, the invention provides a process for the microbial/enzymatic synthesis of substituted ketones of the formula (I)

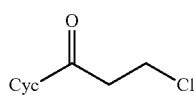
(I)

in which
Cyc is a mono- or polynuclear, saturated or unsaturated, carbocyclic or heterocyclic, aromatic or non-aromatic, optionally mono- or polysubstituted ring,
comprising the microbial/enzymatic oxidation of an alcohol of the formula (II)

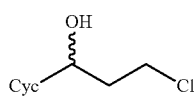
(II)

in each case in stereoisomerically pure form or as a mixture of stereoisomers, in the presence of a phenylethanol dehydrogenase mutant defined herein, optionally with the addition of oxidation equivalents, such as in particular $NAD^+$.

In particular, the reaction takes place under conditions of oxidation equivalent regeneration, using a $C_1$ to $C_6$-monoalkanone as sacrificial ketone.

The enzyme mutant used can be used here in isolated form, such as, for example, optionally immobilized on a solid support, or expressed in microbial cells which are optionally immobilized on a solid support.

Finally, the invention provides the use of an enzyme mutant defined herein in the preparation of duloxetine alcohol and/or duloxetine.

3. Further Embodiments of the Invention 3.1 Proteins

The present invention is not limited to the specifically disclosed proteins and enzymes with phenylethanol dehydrogenase activity, but also extends to functional equivalents thereof.

"Functional equivalents" or analogs of the specifically disclosed enzymes are, within the context of the present invention, polypeptides different therefrom which also have the desired biological activity, such as, for example, phenylethanol dehydrogenase activity.

Thus, for example, "functional equivalents" are understood as meaning enzymes which, in the test used for "phenylethanol dehydrogenase activity" within the context of the invention, have an activity of an enzyme comprising an amino acid sequence defined herein that is lower or higher by at least 1%, in particular by at least about 5 to 10%, such as, for example, at least 10% or at least 20%, such as, for example, at least 50% or 75% or 90%. Moreover, functional equivalents are preferably stable between pH 4 to 11 and advantageously have a pH optimum in a range from pH 5 to 10, such as, in particular, 6.5 to 9.5 or 7 to 8 or about 7.5, and a temperature optimum in the range from 15° C. to 80° C. or 20° C. to 70° C., such as, for example, about 30 to 60° C. or about 35 to 45° C., such as about 40° C.

Within the context of the invention, the "phenylethanol dehydrogenase activity" can be demonstrated with the help of various known tests. Without being limited thereto, mention may be made of a test using a reference substance, such as, for example, TAC or TACA, under standard conditions, as defined in the experimental section (cf. description of tests 1), 2) or 3)), or a biotransformation (complete reaction TAC→TACA with cofactor regeneration by means of isopropanol or 2-butanol) in a 4l reactor.

According to the invention, "functional equivalents" are also understood in particular as meaning "mutants" which, in at least one sequence position of the aforementioned amino acid sequences, have a different amino acid than that specifically mentioned but nevertheless have one of the aforementioned biological activities. "Functional equivalents" thus include the mutants obtainable by one or more amino acid additions, substitutions, deletions and/or inversions, it being possible for said modifications to occur at any sequence position provided they lead to a mutant having the profile of properties according to the invention. Functional equivalence is in particular also present if the reactivity patterns between mutant and unmodified polypeptide are in qualitative agreement, i.e. for example identical substrates are converted at a different rate. Examples of suitable amino acid substitutions are summarized in the table below:

| Original radical | Examples of substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the described polypeptides and "functional derivatives" and "salts" of the polypeptides.

Here, "precursors" are natural or synthetic precursors of the polypeptides with or without the desired biological activity.

The expression "salts" is understood as meaning both salts of carboxyl groups and also acid addition salts of amino groups in the protein molecules according to the invention. Salts of carboxyl groups can be prepared in a manner known per se and comprise inorganic salts, such as, for example, sodium salts, calcium salts, ammonium salts, iron salts and zinc salts, and also salts with organic bases, such as, for example, amines, such as triethanolamine, arginine, lysine, piperidine and the like. Acid addition salts, such as, for example, salts with mineral acids, such as hydrochloric acid or sulfuric acid, and salts with organic acids, such as acetic acid and oxalic acid, are likewise provided by the invention.

"Functional derivatives" of polypeptides according to the invention can likewise be prepared on functional amino acid side groups or on their N- or C-terminal end with the help of known techniques. Derivatives of this type comprise, for example, aliphatic esters of carboxylic acid groups, amides of carboxylic acid groups, obtainable by reaction with ammonia or with a primary or secondary amine; N-acyl derivates of free amino groups, prepared by reaction with acyl groups; or O-acyl derivatives of free hydroxy groups, prepared by reaction with acyl groups.

"Functional equivalents" naturally also comprise polypeptides which are accessible from other organisms, and also naturally occurring variants. For example, through sequence comparison it is possible to determine areas of homologous sequence regions and determine equivalent enzymes in accordance with the specific provisions of the invention.

"Functional equivalents" likewise comprise fragments, preferably individual domains or sequence motifs, of the polypeptides according to the invention, which, for example, have the desired biological function.

Moreover, "functional equivalents" are fusion proteins which have one of the aforementioned polypeptide sequences or functional equivalents derived therefrom and at least one other, functionally different, heterologous sequence in functional N- or C-terminal linkage (i.e. without mutual substantial functional impairment of the fusion protein parts). Non-limiting examples of heterologous sequences of this type are, for example, signal peptides, histidine anchors or enzymes.

"Functional equivalents" also included according to the invention are homologs to the specifically disclosed proteins. These have at least 60%, preferably at least 75%, in particular at least 85%, such as, for example, 90, 91, 92, 93, 94, 95, 96, 97, 98 or 99%, homology (or identity) to one of the specifically disclosed amino acid sequences, calculated according to the algorithm by Pearson and Lipman, Proc. Natl. Acad, Sci. (USA) 85(8), 1988, 2444-2448. A percentage homology or identity of a homologous polypeptide according to the invention means in particular percentage identity of the amino acid radicals, based on the total length of one of the amino acid sequences specifically described herein.

The percentage identity values can also be ascertained by reference to BLAST alignments, algorithm blastp (protein-protein BLAST), or by using the Clustal settings given below.

In the case of a possible protein glycosylation, "functional equivalents" according to the invention comprise proteins of the type referred to above in deglycosylated or glycosylated form and also modified forms obtainable by modifying the glycosylation pattern.

Homologs of the proteins or polypeptides according to the invention can be produced by mutagenesis, e.g. by point mutation, lengthening or shortening of the protein.

Homologs of the proteins according to the invention can be identified by screening combinatorial libraries of mutants, such as, for example, truncated mutants. For example, a variegated library of protein variants can be produced by combinatorial mutagenesis at the nucleic acid level, such as, for example, by enzymatic ligation of a mixture of synthetic oligonucleotides. There is a large number of processes which can be used for producing libraries of potential homologs from a degenerated oligonucleotide sequence. The chemical synthesis of a degenerated gene sequence can be carried out in an automatic DNA synthesizer, and the synthetic gene can then be ligated into a suitable expression vector. Use of a degenerated set of genes facilitates the provision of all sequences in one mixture which code the desired set of potential protein sequences. Processes for the synthesis of degenerated oligonucleotides are known to the person skilled in the art (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

Several techniques are known in the prior art for the screening of gene products in combinatorial libraries which have been produced by point mutations or shortening, and for the screening of cDNA libraries for gene products with a selected property. These techniques can be adapted for the rapid screening of the gene libraries which have been produced by combinatorial mutagenesis of homologs according to the invention. The techniques used most often for screening large gene libraries, which form the basis of high-throughput analysis, comprise the cloning of the gene library into replicatable expression vectors, transformation of the suitable cells with the resulting vector library and expression of the combinatorial genes under conditions under which detection of the desired activity facilitates isolation of the vector that encodes the gene whose product has been detected. Recursive ensemble mutagenesis (REM), a technique that increases the frequency of functional mutants in the libraries, can be used in combination with the screening tests for identifying homologs (Arkin and Yourvan (1992) PNAS 89:7811-7815; Delgrave et al. (1993) Protein Engineering 6(3):327-331).

3.2 Nucleic Acids and Constructs
3.2.1 Nucleic Acids

The invention also provides nucleic acid sequences which code for an enzyme with phenylethanol dehydrogenase activity.

The present invention also relates to nucleic acids with a certain degree of identity to the specific sequences described herein.

"Identity" between two nucleic acids is understood as meaning the identity of the nucleotides over the respective total nucleic acid length, in particular the identity that is calculated by comparison with the help of the vector NTI suite 7.1 software from Informax (USA) using the Clustal method (Higgins D G, Sharp P M. Fast and sensitive multiple sequence alignments on a microcomputer. Comput Appl. Biosci. 1989 April; 5(2):151-1) on setting the following parameters:

Multiple Alignment Parameters:

| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| FAST algorithm | on |
| K-tuple size | 1 |

| Gap penalty | 3 |
| Window size | 5 |
| Number of best diagonals | 5 |

Alternatively, the identity can also be determined in accordance with Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, according to internet address: ebi.ac.uk/Tools/clustalw/index.html# and with the following parameters:

| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All of the nucleic acid sequences mentioned herein (single-stranded and double-stranded DNA and RNA sequences, such as, for example, cDNA and mRNA) can be produced in a manner known per se by chemical synthesis from the nucleotide building blocks, such as, for example, by fragment condensation of individual overlapping, complementary nucleic acid building blocks of the double helix. The chemical synthesis of oligonucleotides can take place, for example, in a known manner, according to the Phosphoamidite method (Voet, Voet, 2nd edition, Wiley Press New York, pages 896-897). The addition of synthetic oligonucleotides and filling of gaps with the help of the Klenow fragment of DNA polymerase and ligation reactions and general cloning methods are described in Sambrook et al. (1989), Molecular Cloning: A laboratory manual, Cold Spring Harbor Laboratory Press.

The invention also provides nucleic acid sequences (single-stranded and double-stranded DNA and RNA sequences, such as, for example, cDNA and mRNA), coding for one of the above polypeptides and their functional equivalents, which are accessible, for example, using artificial nucleotide analogs.

The invention provides both isolated nucleic acid molecules which code for polypeptides or proteins according to the invention or biologically active segments thereof, and also nucleic acid fragments, which can be used, for example, for use as hybridization probes or primers for the identification or amplification of coding nucleic acids according to the invention.

Moreover, the nucleic acid molecules according to the invention can comprise untranslated sequences from the 3'- and/or 5'-end of the coding region of the gene.

The invention further comprises the nucleic acid molecules complementary to the specifically described nucleotide sequences, or a segment thereof.

The nucleotide sequences according to the invention permit the generation of probes and primers that can be used for the identification and/or cloning of homologous sequences in other cell types and organisms. Such probes or primers usually comprise a nucleotide sequence region that hybridizes under "stringent" conditions (see below) to at least about 12, preferably at least about 25, such as, for example, about 40, 50 or 75, successive nucleotides of a sense strand of a nucleic acid sequence according to the invention or of a corresponding antisense strand.

An "isolated" nucleic acid molecule is separated from other nucleic acid molecules that are present in the natural source of the nucleic acid and can, moreover, be essentially free from other cellular material or culture medium, when it is produced by recombinant techniques, or free from chemical precursors or other chemicals when it is synthesized chemically.

A nucleic acid molecule according to the invention can be isolated by means of standard techniques in molecular biology and the sequence information provided according to the invention. For example, cDNA can be isolated from a suitable cDNA library by using one of the specifically disclosed complete sequences or a segment thereof as hybridization probe and standard hybridization techniques (as described, for example, in Sambrook, J., Fritsch, E. F. and Maniatis, T. Molecular Cloning: A Laboratory Manual, 2nd edition, Cold Spring Harbor Laboratory, Cold Spring Harbor Laboratory Press, Cold Spring Harbor, N.Y., 1989). Moreover, a nucleic acid molecule comprising one of the disclosed sequences or a segment thereof can be isolated by polymerase chain reaction, using the oligonucleotide primers that have been created on the basis of this sequence. The nucleic acid amplified in this way can be cloned into a suitable vector and can be characterized by DNA sequence analysis. The oligonucleotides according to the invention can also be prepared by standard synthesis methods, e.g. using an automatic DNA synthesizer.

Nucleic acid sequences according to the invention, or derivatives thereof, homologs or parts of these sequences, can be isolated, for example, using customary hybridization methods or the PCR technique from other bacteria, e.g. via genomic or cDNA libraries. These DNA sequences hybridize under standard conditions with the sequences according to the invention.

"Hybridization" is understood as meaning the ability of a poly- or oligonucleotide to bind to a virtually complementary sequence under standard conditions while nonspecific bonds between noncomplementary partners do not occur under these conditions. For this, the sequences may be 90-100% complementary. The property of complementary sequences to be able to specifically bind to one another makes them useful, for example, in the Northern Blot or Southern Blot technique or for primer binding in PCR or RT-PCR.

For the hybridization, short oligonucleotides of the preserved regions are advantageously used. However, it is also possible to use longer fragments of the nucleic acids according to the invention or the complete sequences for the hybridization. These standard conditions vary depending on the nucleic acid used (oligonucleotide, longer fragment or complete sequence) or depending on which type of nucleic acid DNA or RNA is used for the hybridization. Thus, for example, the melting temperatures for DNA:DNA hybrids are ca. 10° C. lower than those of DNA:RNA hybrids of the same length.

Standard conditions are to be understood, for example depending on the nucleic acid, as meaning temperatures between 42 and 58° C. in an aqueous buffer solution with a concentration between 0.1 and 5×SSC (1×SSC=0.15 M NaCl, 15 mM sodium citrate, pH 7.2) or additionally in the presence of 50% formamide, such as, for example, 42° C. in 5×SSC, 50% formamide. Advantageously, the hybridization conditions for DNA:DNA hybrids are 0.1×SSC and temperatures between about 20° C. and 45° C., preferably between about 30° C. and 45° C. For DNA:RNA hybrids, the hybridization conditions are advantageously 0.1×SSC and temperatures between 30° C. and 55° C., preferably between about 45° C. and 55° C. These stated temperatures for the hybridization are examples of calculated melting temperature values for a nucleic acid with a length of ca. 100 nucleotides and a G+C content of 50% in the absence of formamide. The experimental conditions for the DNA hybridization are described in the relevant textbooks on genetics, such as, for example, Sambrook et al., "Molecular Cloning", Cold Spring Harbor Laboratory, 1989, and can be calculated by formulae known to the person skilled in the art, for example as a function of the length of the nucleic acids, the type of hybrids or the G+C content. A person skilled in the art can find further information on hybridization in the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

The "hybridization" can take place in particular under stringent conditions. Such hybridization conditions are described, for example, in Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions are understood in particular as meaning: incubation at 42° C. overnight in a solution consisting of 50% formamide, 5×SSC (750 mM NaCl, 75 mM trisodium citrate), 50 mM sodium phosphate (pH 7.6), 5×Denhardt solution, 10% dextran sulfate and 20 g/ml of denatured, sheared salmon sperm DNA, followed by a washing step of the filter with 0.1×SSC at 65° C.

The invention also provides derivatives of the specifically disclosed or derivable nucleic acid sequences.

Thus, further nucleic acid sequences according to the invention can be derived e.g. from SEQ ID NO:1 or 3 and can differ therefrom by addition, substitution, insertion or deletion of single or multiple nucleotides, but still code for polypeptides with the desired profile of properties.

Also included according to the invention are those nucleic acid sequences which comprise so-called silent mutations or have been altered corresponding to the codon usage of a special origin or host organism, compared to a specifically mentioned sequence, as are naturally occurring variants, such as, for example, splicing variants or allele variants.

Likewise provided are sequences obtainable by conservative nucleotide substitutions (i.e. the amino acid in question is replaced by an amino acid of the same charge, size, polarity and/or solubility).

The invention also provides the molecules derived by sequence polymorphisms from the specifically disclosed nucleic acids. These genetic polymorphisms can exist between individuals within a population owing to natural variation. These natural variations usually bring about a variance of from 1 to 5% in the nucleotide sequence of a gene.

Derivatives of the nucleic acid sequence according to the invention with the sequence SEQ ID NO: 1 or 3 are to be understood as meaning, for example, allele variants which have at least 60% homology at the derived amino acid level, preferably at least 80% homology, very particularly preferably at least 90% homology over the entire sequence region (with regard to homology at the amino acid level, reference should be made to the above statements in respect of the polypeptides). Over part regions of the sequences, the homologies can advantageously be higher.

Furthermore, derivatives are also to be understood as meaning homologs of the nucleic acid sequences according to the invention, in particular of SEQ ID NO: 1 and 3, for example fungal or bacterial homologs, shortened sequences, single-stranded DNA or RNA of the coding and noncoding DNA sequence.

Moreover, derivatives are to be understood as meaning, for example, fusions with promoters. The promoters, which are connected upstream of the stated nucleotide sequences, can be altered by at least one nucleotide exchange, at least one insertion, inversion and/or deletion, without the functionality and/or effectiveness of the promoters being impaired. Furthermore, the effectiveness of the promoters can be increased by altering their sequence or they can be replaced completely by more effective promoters even from organisms of different species.

3.2.2 Generation of Functional Mutants

Moreover, methods for producing functional mutants of enzymes according to the invention are known to the person skilled in the art.

Depending on the technique used, the person skilled in the art can insert completely random or else more targeted mutations into genes or else noncoding nucleic acid regions (which are important, for example, for regulation of the expression) and then create gene libraries. The molecular biological methods required for this are known to the person skilled in the art and described, for example, in Sambrook and Russell, Molecular Cloning. 3rd edition, Cold Spring Harbor Laboratory Press 2001.

Methods for altering genes and thus for altering the protein coded by these have been known to the person skilled in the art for a long time, such as, for example,

- site-specific mutagenesis, in which one or more nucleotides of a gene are exchanged in a targeted manner (Trower M K (ed.) 1996; In vitro mutagenesis protocols. Humana Press, New Jersey),
- saturation mutagenesis, in which at any desired position in a gene a codon for any desired amino acid can be exchanged or added (Kegler-Ebo D M, Docktor C M, DiMaio D (1994) Nucleic Acids Res 22:1593; Barettino D, Feigenbutz M, Valcarel R, Stunnenberg H G (1994) Nucleic Acids Res 22:541; Barik S (1995) Mol Biotechnol 3:1),
- error-prone polymerase chain reaction (error-prone PCR), in which nucleotide sequences are mutated by defective DNA polymerases (Eckert K A, Kunkel T A (1990) Nucleic Acids Res 18:3739);
- the SeSaM method (Sequence Saturation Method), in which preferred exchanges are prevented by the polymerase. Schenk et al., Biospektrum, Vol. 3, 2006, 277-279
- inserting genes into mutator strains, in which, for example on account of defective DNA repair mechanisms, an increased mutation rate of nucleotide sequences arises (Greener A, Callahan M, Jerpseth B (1996) An efficient random mutagenesis technique using an *E. coli* mutator strain. In: Trower M K (ed.) In vitro mutagenesis protocols. Humana Press, New Jersey), or
- DNA shuffling, in which a pool of closely related genes is formed and digested and the fragments are used as templates for a polymerase chain reaction, in which, through repeated strand separation and reannealing, ultimately mosaic genes of full length are produced (Stemmer WPC (1994) Nature 370:389; Stemmer WPC (1994) Proc Natl Acad Sci USA 91:10747).

Using so-called directed evolution (described, inter alia, in Reetz M T and Jaeger K-E (1999), Topics Curr Chem 200:31; Zhao H, Moore J C, Volkov A A, Arnold F H (1999), Methods for optimizing industrial enzymes by directed evolution, in: Demain A L, Davies J E (ed.) Manual of industrial microbiology and biotechnology. American Society for Microbiology), the person skilled in the art can produce functional mutants also in a targeted manner and also on an industrial scale. Here, in a first step, firstly gene libraries of the particular proteins are generated, for which, for example, it is possible to use the methods given above. The gene libraries are expressed in a suitable manner, for example by bacteria or by phage display systems.

The genes in question of host organisms which express functional mutants with properties which largely correspond to the desired properties can be subjected to a further mutation round. The steps of mutation and of selection or of screening can be repeated iteratively until the functional mutants present have the desired properties to an adequate extent. As a result of this iterative procedure, a limited number of mutations, such as e.g. 1 to 5 mutations, can be undertaken stepwise and their influence on the enzyme property in question can be evaluated and selected. The selected mutant can then be subjected in a similar way to a further mutation step. As a result, the number of individual mutants to be investigated can be significantly reduced.

Nonlimiting examples of mutants according to the invention which have been made accessible by error-prone mutagenesis of an enzyme according to SEQ ID NO:2 are summarized in table 1 below.

TABLE 1

Mutants produced by error-prone mutagenesis

| Clone | Mutation(s) | | | |
|---|---|---|---|---|
| 1 | I19V | I148T | | |
| 5 | L52P | F103I | V216A | G222S |
| 7 | P217L | | | |
| 8 | I19F | | | |
| 9 | E44G | A47S | | |
| 10 | R82H | I92S | | |
| 11 | V87I | M128V | L139P | |
| 11-1 | D171G | | | |
| 12 | K108E | | | |
| 13 | S170P | T191I | L240I | |
| 14 | P97S | L139Q | | |
| 15 | T79M | T109P | L139P | G163D |
| 17 | N113D | | | |
| 19 | N17H | I96T | L101P | |
| 20 | E30G | T58A | | |
| 21 | F80V | F164L | | |
| 22 | N113H | | | |
| 22-1 | P94S | | | |
| 23 | D202V | F234I | | |
| 24 | R4G | D84G | S229P | |
| 27 | I77V | S156R | A228T | |
| 28 | F110S | V216A | D243G | |
| 29 | W145R | L146I | | |
| 30 | D62N | I96V | A196V | |
| 32 | G245D | | | |
| 33 | T189A | | | |
| 35 | N17S | A28V | L86P | |
| 37 | V125A | D202Y | | |
| 40 | E44G | | | |
| 42 | D115G | | | |
| 45 | T79A | | | |
| 46 | Y93F | H249L | | |
| 47 | K174T | | | |
| 48 | R188L | | | |
| 50 | D7V | | | |
| 50-1 | S156G | | | |
| 51 | F164Y | | | |
| 52 | E46K | D231G | | |
| 52-1 | M200K | | | |
| 53 | A181V | | | |

TABLE 1-continued

Mutants produced by error-prone mutagenesis

| Clone | Mutation(s) | | | |
|---|---|---|---|---|
| 53-2 | L95M | | | |
| 54 | K107R | M246T | | |
| 55 | P184T | | | |
| 56 | L186H | | | |
| 58 | H249Y | | | |
| 59 | A48S | | | |
| 61 | N89S | K129T | | |
| 62 | I92N | | | |
| 62-2 | S116L | | | |
| 63 | Y144F | M207K | | |
| 64 | N17S | K158R | | |
| 65 | A71T | M200V | | |
| 67 | S195T | | | |
| 68 | L39M | | | |
| 70 | N89S | K129T | | |
| 71 | L146R | | | |
| 72 | D7G | F118L | | |
| 73 | F27Y | I96S | L227M | |
| 75 | A71T | A241T | D243E | |
| 76 | R188H | | | |
| 77 | A48V | Y144F | M207K | |
| 79 | T79A | R188L | | |
| 80 | L9H | N17D | D68G | N113I | H153Q |
| 80-1 | T79P | | | |
| 81 | S233G | | | |
| 82 | L9H | V11L | T102S | |
| 82-2 | T13A | | | |
| 83 | D62A | | | |
| 84 | A71T | | | |
| 85 | D115Y | | | |
| 86 | R188H | | | |
| 87 | A194V | | | |
| 88 | L214I | L240F | | |
| 90 | E44G | I162L | | |
| 91 | A71T | K74E | | |
| 91-2 | R50W | D62E | I112L | |
| 93 | D99G | | | |
| 94 | W133G | S170P | T191I | L240I |
| 95 | R213S | T221A | | |
| 96 | T2S | R55H | G73R | |
| 97 | D84G | F234L | | |
| 98 | V114A | | | |
| 99 | T152A | | | |
| 100 | V247G | | | |
| 101 | N17H | D202V | F234I | |
| 102 | I96T | L101P | | |
| 103 | F226S | | | |
| 104 | Q3P | S141T | T165I | S229P |
| 105 | V11G | N131S | N180S | |
| 106 | I77V | S156R | | |
| 107 | A228T | | | |
| 108 | K107E | F110S | V216A | D243G |
| 110 | K129R | N131D | K174R | S195T | G237D |
| 112 | I211T | | | |
| 114 | N17S | A28V | L86P | |
| 115 | I36V | | | |
| 117 | G176R | | | |
| 118 | F201I | | | |
| 119 | D243E | | | |
| 120 | T2A | I19S | R55C | I92N |
| 122 | A159T | N161T | I182S | |
| 123 | Q65R | L146P | I182T | T192I |
| 124 | I112N | | | |
| 126 | E44G | N113D | | |
| 128 | F103L | | | |
| 129 | I155V | S195T | | |
| 130 | D202G | | | |
| 131 | V247M | R248I | | |
| 132 | G67C | | | |
| 133 | D175G | | | |
| 134 | D243N | | | |
| 135 | G244S | | | |
| 137 | M200V | F201L | | |

The results according to the invention also give important information with regard to structure and sequence of the enzymes in question which are required for generating further enzymes having desired modified properties in a targeted manner. In particular, so-called "hot spots" can be defined, i.e. sequence segments which are potentially suitable for modifying an enzyme property by inserting targeted mutations.

Nonlimiting examples of such hot spot regions of the enzymes according to the invention are, based on SEQ ID NO:2, summarized below:
(1) 142 to 153 (loop 2) and
(2) 190 to 211 (helix alpha FG1)
(3) 93 to 96 (loop 1)
(4) 241 to 249 (C terminus)
(5) 138 to 141 (hydrophilic region of binding pocket) and
(6) Cys61 and/or Cys 83

It is likewise possible to derive information with regard to the amino acid sequence positions in whose region mutations can be carried out which should probably have little influence on the enzyme activity, and can be referred to as potential "silent mutations". Such mutation positions are summarized for SEQ ID NO:2 in table 2 below:

TABLE 2

| Pos | | Pos | | Pos | | Pos | |
|---|---|---|---|---|---|---|---|
| 1 | Met | 65 | Gln | 103 | Phe | 196 | Ala |
| 2 | Thr | 68 | Asp | 104 | Glu | 198 | Ser |
| 3 | Gln | 70 | Glu | 107 | Lys | 199 | Ala |
| 6 | Lys | 71 | Ala | 108 | Lys | 202 | Asp |
| 7 | Asp | 74 | Lys | 111 | Glu | 203 | Val |
| 47 | Ala | 75 | Gln | 174 | Lys | 206 | Asn |
| 48 | Ala | 77 | Ile | 175 | Asp | 207 | Met |
| 50 | Arg | 78 | Ser | 188 | Arg | 208 | Leu |
| 51 | Asn | 95 | Leu | 192 | Thr | 216 | Val |
| 55 | Arg | 99 | Asp | 193 | Glu | 230 | Asp |
| 60 | Lys | 100 | Glu | 194 | Ala | | |

3.2.3 Constructs

Moreover, the invention provides expression constructs comprising, under the genetic control of regulatory nucleic acid sequences, a nucleic acid sequence coding for a polypeptide according to the invention; and vectors comprising at least one of these expression constructs.

According to the invention, an "expression unit" is to be understood as meaning a nucleic acid with expression activity which comprises a promoter as defined herein and, after functional linkage to a nucleic acid to be expressed or to a gene, regulates the expression, thus the transcription and the translation of this nucleic acid or of this gene. Consequently, in this connection, the expression "regulatory nucleic acid sequence" is also used. In addition to the promoter, further, regulatory elements, such as, for example, enhancers, may be present.

According to the invention, an "expression cassette" or "expression construct" is understood as meaning an expression unit which is functionally linked to the nucleic acid to be expressed or to the gene to be expressed. In contrast to an expression unit, an expression cassette thus comprises not only nucleic acid sequences which regulate transcription and translation, but also the nucleic acid sequences which are to be expressed as a consequence of the transcription and translation as protein.

Within the context of the invention, the terms "expression" or "overexpression" describe the production of or increase in the intercellular activity of one or more enzymes in a microorganism which are coded by the corresponding DNA. For this, for example, a gene can be inserted into an organism, a present gene can be replaced by another gene, the copy number of the gene or genes can be increased, a strong promoter can be used or a gene can be used which codes for a corresponding enzyme with a high activity, and these measures can optionally be combined.

Preferably, such constructs according to the invention comprise a promoter 5'-upstream of the particular coding sequence and a terminator sequence 3'-downstream, and also optionally further customary regulatory elements, which are in each case operatively linked to the coding sequence.

According to the invention, "promoter", a "nucleic acid with promoter activity" or a "promoter sequence" is understood as meaning a nucleic acid which, in functional linkage to a nucleic acid to be transcribed, regulates the transcription of this nucleic acid.

In this context, a "functional" or "operative" linkage is understood as meaning, for example, the sequential arrangement of one of the nucleic acids with promoter activity and a nucleic acid sequence to be transcribed and optionally further regulatory elements, such as, for example, nucleic acid sequences, which ensure the transcription of nucleic acids, and also, for example, a terminator in such a way that each of the regulatory elements is able to fulfill its function during the transcription of the nucleic acid sequence. For this, a direct linkage in the chemical sense is not absolutely necessary. Genetic control sequences, such as, for example, enhancer sequences, can exert their function on the target sequence also from further removed positions or even from other DNA molecules. Preference is given to arrangements in which the nucleic acid sequence to be transcribed is positioned behind (i.e. on the 3' end) of the promoter sequence so that the two sequences are joined together covalently. Here, the distance between the promoter sequence and the nucleic acid sequence to be expressed transgenically can be less than 200 base pairs, or less than 100 base pairs or less than 50 base pairs.

Besides promoters and terminator, examples of further regulatory elements are targeting sequences, enhancers, polyadenylation signals, selectable markers, amplification signals, replication origins and the like. Suitable regulatory sequences are described, for example, in Goeddel, Gene Expression Technology: Methods in Enzymology 185, Academic Press, San Diego, Calif. (1990).

Nucleic acid constructs according to the invention comprise in particular sequence SEQ ID NO: 1 or 3 or derivatives and homologs thereof, and also the nucleic acid sequences derivable therefrom which have been operatively or functionally linked to one or more regulatory signals advantageously for controlling, e.g. increasing, gene expression.

In addition to these regulatory sequences, the natural regulation of these sequences may still be present upstream of the actual structural genes and optionally may have been genetically altered in such a way that the natural regulation has been switched off and expression of the genes has been increased. However, the nucleic acid construct may also be simpler in design, i.e. no additional regulatory signals have been inserted upstream of the coding sequence and the natural promoter, together with its regulation, has not been removed. Instead of this, the natural regulatory sequence is mutated in such a way that there is no longer any regulation and expression of the gene is increased.

A preferred nucleic acid construct also advantageously comprises one or more of the previously mentioned "enhancer" sequences, functionally linked to the promoter, which enable increased expression of the nucleic acid sequence. Additional advantageous sequences, such as further regulatory elements or terminators, may also be inserted at the 3' end of the DNA sequences. The nucleic acids according to the invention may be present in one or more copies in the construct. The construct may also comprise further markers, such as antibiotic resistances or auxotrophy-complementing genes, optionally for selection on the construct.

Examples of suitable regulatory sequences are present in promoters such as cos, tac, trp, tet, trp-tet, lpp, lac, lpp-lac, lacI$^q$-, T7, T5, T3, gal, trc, ara, rhaP (rhaP$_{BAD}$)SP6, lambda-P$_R$ or in the lambda-P$_L$ promoter, which are advantageously used in Gram-negative bacteria. Further advantageous regulatory sequences are present, for example, in the Gram-positive promoters amy and SPO2, in the yeast or fungal promoters ADC1, MFalpha, AC, P-60, CYC1, GAPDH, TEF, rp28, ADH. It is also possible to use artificial promoters for regulation.

For expression in a host organism, the nucleic acid construct is advantageously inserted into a vector, such as, for example, a plasmid or a phage, which permits optimum expression of the genes in the host. As well as plasmids and phages, vectors are also to be understood as meaning any other vectors known to the person skilled in the art, for example viruses, such as SV40, CMV, baculovirus and adenovirus, transposons, IS elements, phasmids, cosmids, and linear or circular DNA. These vectors can be replicated autonomously in the host organism or can be replicated chromosomally. These vectors constitute a further embodiment of the invention.

Suitable plasmids are, for example, in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCl, in *streptomyces* pIJ101, pIJ364, pIJ702 or pIJ361, in *bacillus* pUB110, pC194 or pBD214, in *corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac$^+$, pBIN19, pAK2004 or pDH51. The specified plasmids constitute a small selection of the possible plasmids. Further plasmids are well known to the person skilled in the art and can be found, for example, in the book Cloning Vectors (Eds. Pouwels P. H. et al. Elsevier, Amsterdam-New York-Oxford, 1985, ISBN 0 444 904018).

In a further embodiment of the vector, the vector comprising the nucleic acid construct according to the invention or the nucleic acid according to the invention can also advantageously be introduced into the microorganisms in the form of a linear DNA and be integrated into the genome of the host organism by way of heterologous or homologous recombination. This linear DNA can consist of a linearalized vector such as a plasmid or only of the nucleic acid construct or of the nucleic acid according to the invention.

For optimum expression of heterologous genes in organisms, it is advantageous to alter the nucleic acid sequences in accordance with the specific "codon usage" used in the organism. The "codon usage" can be readily determined with the aid of computer analyses of other known genes from the organism in question.

An expression cassette according to the invention is prepared by fusing a suitable promoter to a suitable coding nucleotide sequence and to a terminator signal or polyadenylation signal. For this, common recombination and cloning techniques are used, as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and also in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which enables optimum expression of the genes in the host. Vectors are well known to the person skilled in the art and can be found, for example, in "Cloning Vectors" (Pouwels P. H. et al., Ed., Elsevier, Amsterdam-New York-Oxford, 1985).

3.3 Microorganisms

Depending on the context, the term "microorganism" can be understood as meaning the wildtype microorganism or a genetically modified, recombinant microorganism or both.

With the help of the vectors according to the invention, it is possible to prepare recombinant microorganisms which, for example, have been transformed with at least one vector according to the invention and can be used for producing the polypeptides according to the invention. Advantageously, the above-described recombinant constructs according to the invention are introduced into a suitable host system and expressed. Here, customary cloning and transfection methods known to the person skilled in the art, such as, for example, coprecipitation, protoplast fusion, electroporation, retroviral transfection and the like, are preferably used in order to cause said nucleic acids to be expressed in the particular expression system. Suitable systems are described, for example, in Current Protocols in Molecular Biology, F. Ausubel et al., Ed., Wiley Interscience, New York 1997, or Sambrook et al. Molecular Cloning: A Laboratory Manual. 2nd edition., Cold Spring Harbor Laboratory, Cold Spring Harbor Laboratory Press, Cold Spring Harbor, N.Y., 1989.

Suitable recombinant host organisms for the nucleic acid according to the invention or the nucleic acid construct are in principle all procaryontic or eucaryontic organisms. Advantageously, the host organisms used are microorganisms such as bacteria, fungi or yeasts. Advantageously, Gram-positive or Gram-negative bacteria, preferably bacteria from the families Enterobacteriaceae, Pseudomonadaceae, Rhizobiaceae, Streptomycetaceae or Nocardiaceae, particularly preferably bacteria of the genera *Escherichia, Pseudomonas, Streptomyces, Nocardia, Burkholderia, Salmonella, Agrobacterium, Clostridium* or *Rhodococcus*, are used. Very particular preference is given to the genus and species *Escherichia coli*. Moreover, further advantageous bacteria can be found in the group of the alpha-proteobacteria, beta-proteobacteria or gamma-proteobacteria.

In this connection, the host organism or the host organisms according to the invention preferably comprise at least one of the nucleic acid sequences, nucleic acid constructs or vectors which code for an enzyme with phenylethanol dehydrogenase activity according to the above definition that are described in this invention.

The organisms used in the method according to the invention are grown or cultured in a manner known to the person skilled in the art, depending on the host organism. As a rule, microorganisms are grown in a liquid medium, which comprises a carbon source mostly in the form of sugars, a nitrogen source mostly in the form of organic nitrogen sources such as yeast extract or salts such as ammonium sulfate, trace elements such as iron, manganese and magnesium salts and optionally vitamins, at temperatures between 0° C. and 100° C., preferably between 10° C. and 60° C. with oxygen gasing. Here, the pH of the nutrient liquid can be maintained at a fixed value, i.e. regulated or not regulated during the culture. Culture can be batchwise, semi-batchwise or continuous. Nutrients can be initially introduced at the start of the fermentation or can be fed in semicontinuously or continuously.

3.4 Recombinant Preparation of Enzymes According to the Invention

The invention further provides processes for the recombinant preparation of polypeptides according to the invention or of functional, biologically active fragments thereof, which comprises cultivating a polypeptide-producing microorganism, optionally inducing the expression of the polypeptides and isolating these from the culture. The polypeptides can also be produced on an industrial scale in this way, if desired.

The microorganisms prepared according to the invention can be cultivated continuously or discontinuously in the batch process (batch cultivation) or in the fed batch (feed process) or repeated fed batch process (repetitive feed process). A summary on known cultivation methods can be found in the textbook by Chmiel (Bioprozeβtechnik 1. Einführung in die Bioverfahrenstechnik [Bioprocessing technology 1. Introduction to bioprocessing technology] (Gustav Fischer Verlag, Stuttgart, 1991)) or in the textbook by Storhas (Bioreaktoren and periphere Einrichtungen [Bioreactors and peripheral devices] (Vieweg Verlag, Braunschweig/Wiesbaden, 1994)).

The culture medium to be used has to suitably satisfy the demands of the particular strains. Descriptions of culture media of different microorganisms can be found in the handbook "Manual of Methods for General Bacteriology" from the American Society for Bacteriology (Washington D.C., USA, 1981).

These media that can be used according to the invention usually comprise one or more carbon sources, nitrogen sources, inorganic salts, vitamins and/or trace elements.

Preferred carbon sources are sugars, such as mono-, di- or polysaccharides. Very good carbon sources are, for example, glucose, fructose, mannose, galactose, ribose, sorbose, ribulose, lactose, maltose, sucrose, raffinose, starch or cellulose. It is also possible to add sugars to the media via complex compounds, such as molasses, or other by-products of sugar refinement. It may also be advantageous to add mixtures of different carbon sources. Other possible carbon sources are oils and fats, such as, for example, soybean oil, sunflower oil, peanut oil and coconut fat, fatty acids such as, for example, palmitic acid, stearic acid or linolic acid, alcohols, such as, for example, glycerol, methanol or ethanol, and organic acids, such as, for example, acetic acid or lactic acid.

Nitrogen sources are usually organic or inorganic nitrogen compounds or materials which comprise these compounds. Examples of nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as corn steep liquor, soybean flour, soybean protein, yeast extract, meat extract and others. The nitrogen sources can be used individually or as a mixture.

Inorganic salt compounds which may be present in the media comprise the chloride salts, phosphorus salts or sulfate salts of calcium, magnesium, sodium, cobalt, molybdenum, potassium, manganese, zinc, copper and iron.

Sulfur sources which can be used are inorganic sulfur-containing compounds, such as, for example, sulfates, sulfites, dithionites, tetrathionates, thiosulfates, sulfides, but also organic sulfur compounds, such as mercaptans and thiols.

Phosphorus sources that can be used are phosphoric acid, potassium dihydrogenphosphate or dipotassium hydrogenphosphate or the corresponding sodium-containing salts.

Chelating agents can be added to the media in order to keep the metal ions in solution. Particularly suitable chelating agents comprise dihydroxyphenols, such as catechol or protocatechuate, or organic acids, such as citric acid.

The fermentation media used according to the invention usually also comprise other growth factors, such as vitamins or growth promoters, which include, for example, biotin, riboflavin, thiamine, folic acid, nicotinic acid, panthothenate and pyridoxine. Growth factors and salts often originate from complex media components, such as yeast extract, molasses, corn steep liquor and the like. Moreover, suitable precursors may be added to the culture medium. The precise composition of the media compounds depends heavily on the particular experiment and is decided individually for each specific case. Information on media optimization is available from the textbook "Applied Microbiol. Physiology, A Practical Approach" (ed. P. M. Rhodes, P. F. Stanbury, IRL Press (1997) p. 53-73, ISBN 0 19 963577 3). Growth media can also be acquired from commercial suppliers, such as Standard 1 (Merck) or BHI (Brain heart infusion, DIEGO) and the like.

All media components are sterilized either by heating (20 min at 1.5 bar and 121° C.) or by sterile filtration. The components can either be sterilized together or, if necessary, separately. All media components may be present at the start of culture or may optionally be added continuously or batchwise.

The temperature of the culture is normally between 15° C. and 45° C., preferably 25° C. to 40° C. and can be kept constant or changed during the experiment. The pH of the medium should be in the range from 5 to 8.5, preferably around 7.0. The pH for the culture can be controlled during culture by adding basic compounds such as sodium hydroxide, potassium hydroxide, ammonia or ammoniac water, or acidic compounds, such as phosphoric acid or sulfuric acid. To control foaming, antifoaming agents, such as, for example, fatty acid polyglycol esters, can be used. To maintain the stability of plasmids, suitable selective substances, such as e.g. antibiotics, can be added to the medium. In order to maintain aerobic conditions, oxygen or oxygen-containing gas mixtures, such as, for example, ambient air, are introduced into the culture. The temperature of the culture is normally 20° C. to 45° C. The culture is continued until a maximum of the desired product has formed. This target is normally reached over the course of from 10 hours to 160 hours.

The fermentation liquor is then processed further. Depending on requirements, the biomass can be removed, in its entirety or in part, from the fermentation liquor by separation methods, such as, for example, centrifugation, filtration, decantation or a combination of these methods, or be left entirely in said liquor.

If the polypeptides are not secreted into the culture medium, the cells can also be disrupted and the product obtained from the lysate by known protein isolation methods. The cells can optionally be disrupted by high-frequency ultrasound, by high pressure, such as, for example, in a French pressure cell, by osmolysis, by the action of detergents, lytic enzymes or organic solvents, by homogenizers or by a combination of several of the methods listed.

Purification of the polypeptides can be achieved using known chromatographic methods, such as molecular sieve chromatography (gel filtration), such as Q-Sepharose chromatography, ion-exchange chromatography and hydrophobic chromatography, and also with other customary methods such as ultrafiltration, crystallization, salting-out, dialysis and native gel electrophoresis. Suitable methods are described, for example, in Cooper, T. G., Biochemische Arbeitsmethoden [Biochemical procedures], Verlag Walter de Gruyter, Berlin, N.Y. or in Scopes, R., Protein Purification, Springer Verlag, New York, Heidelberg, Berlin.

To isolate the recombinant protein, it may be advantageous to use vector systems or oligonucleotides which lengthen the cDNA by certain nucleotide sequences and thus code for modified polypeptides or fusion proteins, which serve, for example, for easier purification. Suitable modifications of this kind are, for example, so-called "tags" that function as anchors, such as, for example, the modification known as hexahistidine anchor, or epitopes that can be recognized as antigens by antibodies (described, for example, in Harlow, E. and Lane, D., 1988, Antibodies: A Laboratory Manual. Cold Spring Harbor (N.Y.) Press). These anchors can serve to secure the proteins to a solid support, such as, for example, a polymer matrix, which can, for example, be used as the packing in a chromatography column, or can be used on a microtiter plate or on some other support.

At the same time, these anchors can also be used for the recognition of the proteins. For recognition of the proteins, it is moreover possible to use customary markers, such as fluorescent dyes, enzyme markers, which after reaction with a substrate form a detectable reaction product, or radioactive markers, alone or in combination with the anchors for derivatization of the proteins.

For the expression of mutants according to the invention, reference may be made to the description of the expression of the wildtype enzyme EbN1 and the expression systems that can be used therefor in WO2005/108590 and WO2006/094945, to which reference is expressly made.

3.5 Enzyme Immobilization

The enzymes according to the invention can be used in the methods described herein in free form or immobilized form. An immobilized enzyme is understood as meaning an enzyme which has been fixed to an inert support. Suitable support materials and the enzymes immobilized thereon are known from EP-A-1149849, EP-A-1 069 183 and DE-A 100193773 and also from the literature sources cited therein. In this regard, reference is made to the disclosure of these specifications in their entirety. Suitable support materials include, for example, clays, clay minerals, such as kaolinite, diatomerous earth, perlite, silicon dioxide, aluminum oxide, sodium carbonate, calcium carbonate, cellulose power, anion exchange materials, synthetic polymers, such as polystyrene, acrylic resins, phenolformaldehyde resins, polyurethanes and polyolefins, such as polyethylene and polypropylene. The support materials are used for producing the supported enzymes usually in a finely divided, particulate form, preference being given to porous forms. The particle size of the support material is usually not more than 5 mm, in particular not more than 2 mm (sieve line). Analogously, when using the dehydrogenase as whole-cell catalyst, a free or immobilized form can be used. Support materials are, for example, Ca alginate, and carrageenan. Enzymes, like cells, can also be crosslinked directly with glutaraldehyde (crosslinking to CLEAs). Corresponding and further immobilization methods are described, for example, in J. Lalonde and A. Margolin "Immobilization of Enzymes" in K. Drauz and H. Waldmann, Enzyme Catalysis in Organic Synthesis 2002, vol. III, 991-1032, Wiley-VCH, Weinheim. Further information on biotransformations and bioreactors for carrying out methods according to the invention can also be found, for example, in Rehm et al (Ed) Biotechology, 2nd edition, vol. 3, chapter 17, VCH, Weinheim.

The invention will now be described in more detail by reference to the following nonlimiting examples.

EXPERIMENTAL SECTION

Example 1

Saturation Mutagenesis 1.1 Molecular Modeling

The mutants were selected by reference to the crystal structure of the enzyme phenylethanol dehydrogenase EbN1 (FIG. 2).

The substrate specificity of the enzyme is determined by two loop regions and one helix (loop 1 and 2 and helix αFG1 in FIG. 2). The helix αFG1 is flexible and closes the active center after binding the substrate. Tyr 93 on loop 1 closes the substrate binding pocket to the front and is thereby responsible for the stereoselectivity. Tyr151 belongs to loop 2 and points into the binding pocket. Thr192 is part of the flexible helix αFG1 and points in the direction of the substrate binding site. These two positions were selected since they influence the substrate binding but do not disturb the amino acids in the catalytic center and the cofactor NAD, i.e. the catalytic mechanism.

1.2 Saturation Mutagenesis

Firstly, saturation mutageneses were carried out separately at positions Y151X and T192X (i.e. exchange of position Y151 and T192 for all other 19 amino acids, also called permutation), then a double mutant (Y151A-T192X) was generated.

This was carried out by means of site-directed mutagenesis in in each case three polymerase chain reactions (see cloning strategy, FIG. 3). Here, the following oligonucleotides were used for the amplification of the DNA:

```
1) Mke123 Upper:
   5'-GTTCATCTTTCCCTGGTTG-3'      (SEQ ID NO: 5)

2) Mke124 Lower:
   5'-GCTACGGCGTTTCACTTC-3'       (SEQ ID NO: 6)

3) Mke798 Y151X Lower:
   5'-GTAATGGGTNNNCGCCTCGA-3'     (SEQ ID NO: 7)

4) Mke793 Y151X Upper:
   5'-TCGAGGCGNNNACCCATTAC-3'     (SEQ ID NO: 8)

5) Mke796 T192X Upper:
   5'-CGGCAACANNNGAAGCGTC-3'      (SEQ ID NO: 9)

6) Mke797 T192 X Lower:
   5'-GACGCTTCNNNTGTTGCCGT-3'     (SEQ ID NO: 10)

7) Mke951 Y151AT192X:
   5'-GGCAACANNNGAAGCGTC-3'       (SEQ ID NO: 11)

8) Mke952 Y151AT192X:
   5'-GACGCTTCNNNTGTTGCC-3'       (SEQ ID NO: 12)
```

The PCR for the amplification of the ebn1H gene segment was carried out as follows: 100 µl of reaction mixture comprised: 1 µl of template (ca. 50 ng of vector pDHE-ebn1H), in each case 1 µl of oligonucleotide (20 ng), 2 µl of dNTPMix (à 10 mM end concentration from Roche), 1 µl of Pfu-Ultra DNA polymerase (1 U/µl from Stratagene), 10 µl of 10×Pfu-Ultra buffer (Stratagene) and 80 µl of sterile water.

The following temperature program was set on the thermocycler (Biometra): 95° C.—5 min; 30 cycles: 95° C.—45 sec, 50° C.—45 sec, 72° C.—45 sec; 72° C.—10 min; 10° C.

1a) PCR oligonucleotides 1 and 3 (6 for T192X)

1b) PCR oligonucleotides 2 and 4 (5 for T192X)

2) PCR oligonucleotides 1 and 2 with product from PCR 1a and b as template (overlap extension)

The amplified ebn1 gene obtained therefrom was purified on a 1.2% agarose gel using a GFX kit (GE Healthcare).

The amplified DNA was cleaved using the restriction enzymes NdeI and HindIII (Fermentas), ligated into the multiple cloning site (MCS) of the vector pDHE (likewise cleaved with NdeI-HindIII) and transformed in XL10 ultra-competent cells (Stratagene). Through a mini-preparation of these cells, the plasmid DNA of the mutants was obtained. Vector pDHE is described as pDHE19.2 vector in DE 19848129 or WO2005/108590.

1.3 Culture of the Cells

The vector pDHE-ebn1H-Y151X or pDHE-ebn1H-T192X (and later pDHE-ebn1H-Y151A-T192X) was firstly transformed into the strain LU12037 (E. coli derivate TG10 pAgro4 pHSG575 (TG10: a RhaA⁻ derivative from E. coli TG1 (Stratagene); pAgro4: Takeshita, S; M; M; Masahashi, W; T (1987) Gene 61, 63-74; pHSG575: T. Tomoyasu et al (2001), Mol. Microbiol. 40 (2)), which coexpresses the chaperone GroEL/S and the lacIq repressor, and plated out on Q-tray plates. The grown colonies were picked using a picking robot (Qpix) and inoculated in a CG preculture (Circular Growth, Gibco) with antibiotics (100 µM ampicillin, 20 µM chloramphenicol and 100 µM spectinomycin) in microtiter plates (MTP). After a growth time of 5 h at 37° C. and 200 rpm, the cells were transferred by hand into the LB main culture with antibiotics (see above) and the corresponding inducers (Rhamnose 0.5 g/l and IPTG 0.1 mM). After growth for 16-18 h, the cells are used in the test.

To disrupt the cells, these were firstly centrifuged, the supernatant was pulled off and the MTP was provided with an adhesive film. The MTP was completely immersed into liquid nitrogen for ca. 3 seconds and then placed again on the laboratory bench to thaw. The most uniform results were achieved in the case of 3-fold rapid freezing with interim thawing at room temperature.

1.4 Enzyme Inhibition

It has been found that the TAC reaction product TACA or a secondary component which is formed during the reaction inhibits the reaction. The substrate was not completely converted. Although the reaction here was an equilibrium reaction, cells and/or substrate were added afresh, for example after 4 hours, so no further reaction took place. Furthermore, the resulting 2-butanone was removed by distillation in order to shift the equilibrium as far as possible to the product side. Despite these measures, complete conversion was not attained.

It was thus an aim to find a mutant which does not necessarily tolerate more active, but primarily larger amounts of product or secondary component in order to achieve the most complete conversion possible and thus a high space-time yield.

Figure 4:
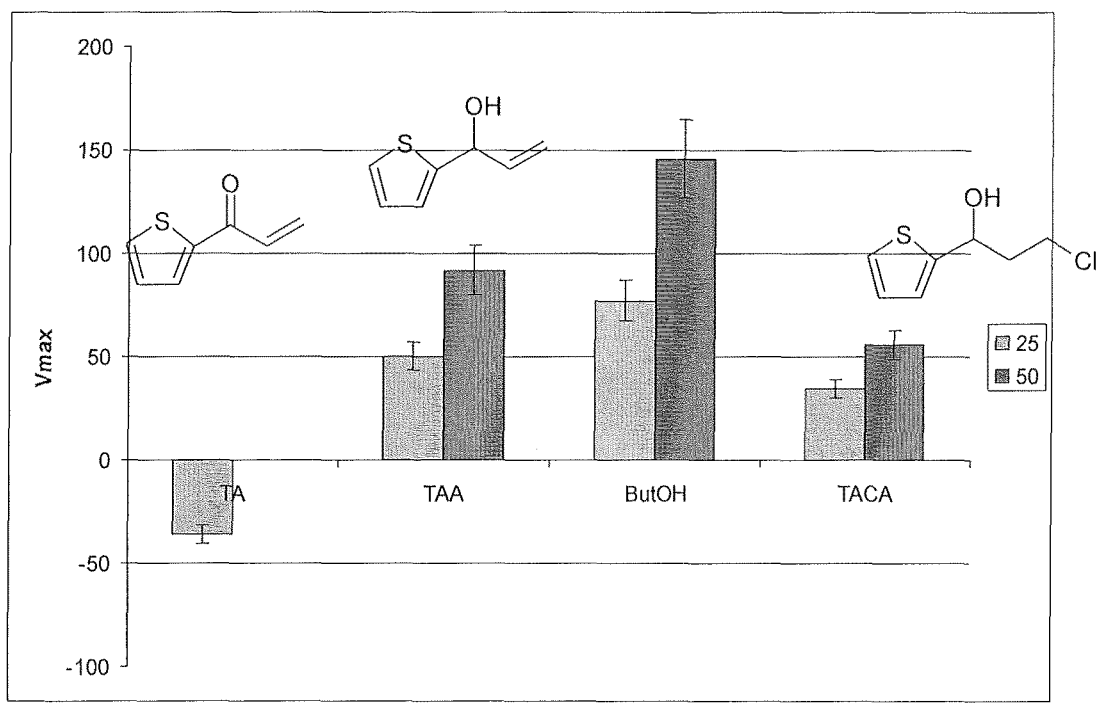
FIG. 4 shows the result of experiments for inhibiting the phenylethanol dehydrogenase EbN1 in the presence of in each case 10 mM TA, TAA or TACA, and also the result of a control batch without inhibiting substance. The experiments were carried out with whole cells; in each case 25 or 50 µl of cell suspension were tested.

In the test which follows, both TACA and also TA or TAA were tested as inhibitors. For this, in a 0.2 ml mixture (MTP) 50 µl of cells (LU11558; an Escherichia coli TG10+ strain with a Rhamnose-inducible pDHE1650 derivative as overexpression plasmid. The chaperone GroEL/S and the lacIq repressor are coexpressed; the wildtype enzyme EbN1 is overexpressed) from a culture in the 100 ml shaking flask, 1.75 mM NAD and 100 mM 2-butanol were added to 80 mM TrisHCl buffer pH 8.0. In each case 10 mM of TA, TAA or TACA were added thereto. Then, in the photometer at 340 nm, the formation of NADH was measured. FIG. 4 illustrates the inhibition of the phenylethanol dehydrogenase EbN1 by giving the particular $V_{max}$ values (resulting amount of NADH per time). The control (without inhibitor) is characterized by ButOH.

As can be seen in FIG. 4, TACA shows the strongest inhibition. Since TA absorbs very strongly in this wavelength range, the formation of NADH cannot be detected here.

For this reason, TACA was added as inhibitor in the other assays. In addition, TACA was also added as inhibitor to the regeneration test with 2-butanol and NAD that had been carried out previously. In order to determine the suitable TACA concentration, various concentrations of cells and TACA were tested. Initially, a concentration series from 0 to 30 mM, then one between 0 and 10 mM, was prepared. On the basis of the results achieved (not shown), a TACA concentration of 10 mM with in each case 25 µl of cells was used in the further test.

1.5 Course of the 2-Butanol Test with and without the Addition of TACA (Regeneration of the Cofactor)

Here, two microtiter plates (96-well) were picked full of clones per amino acid position. The microtiter plates were completely sequenced and the values assigned to the individual mutations.

Figure 5A:
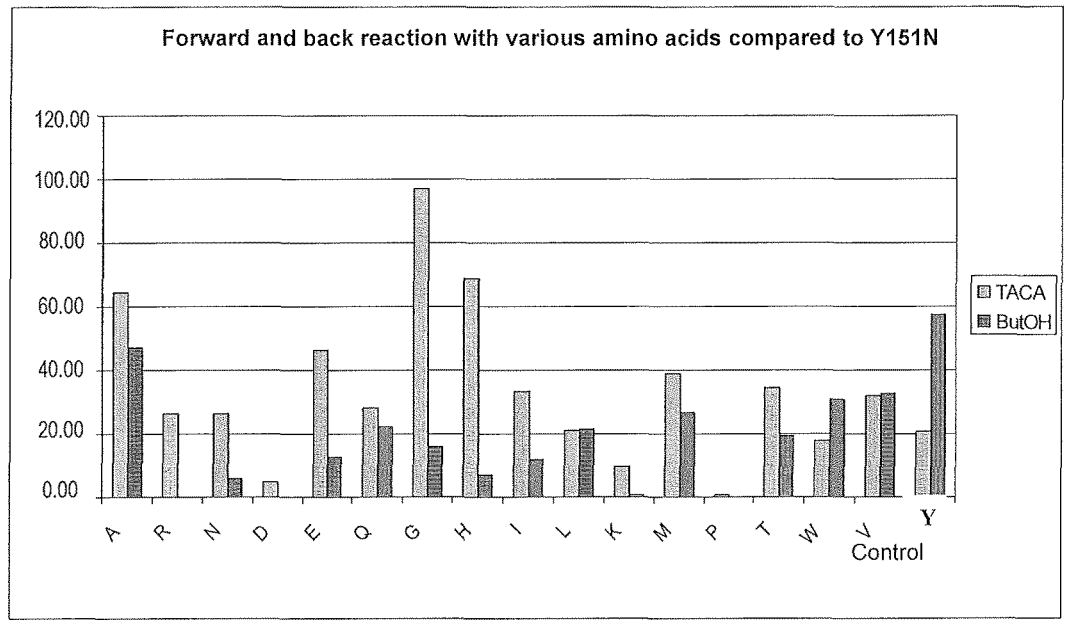
FIG. 5A illustrates the regeneration ability of the cofactor with 2-butanol in the presence and absence of TACA by various mutants of the type Y151X.
Figure 5B:
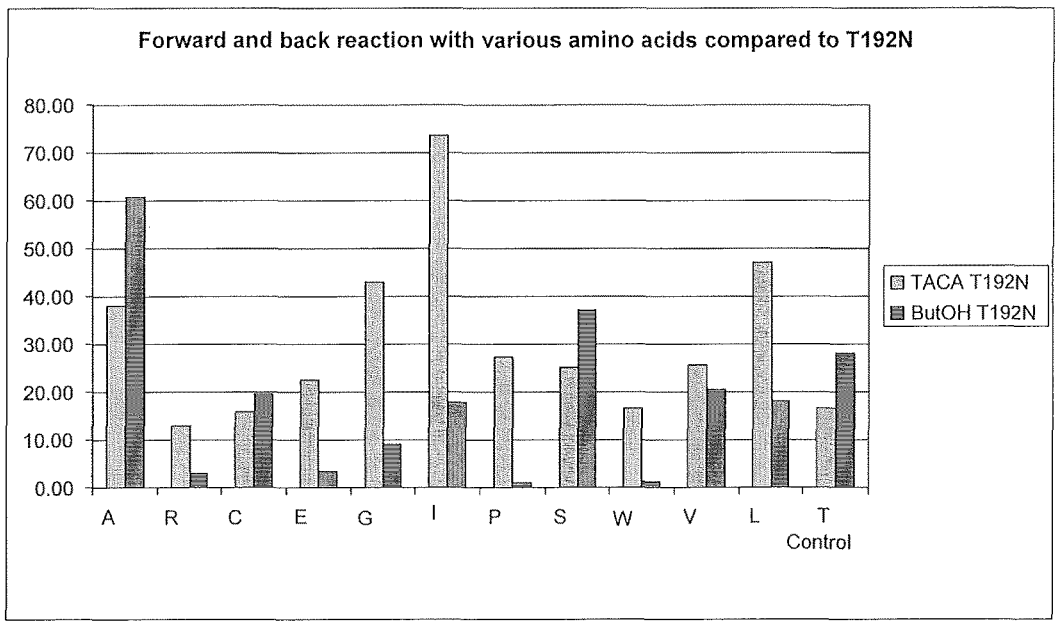
FIG. 5B illustrates the regeneration ability of the cofactor with 2-butanol in the presence and absence of TACA by various mutants of the type T192X.

The cells were cultured as described above, then disrupted and finally resuspended in 100 µl of water. 25 µl of this cell suspension were placed into a new microtiter plate and made up to a volume of 100 µl with water. The substrate solution (end concentrations: 100 mM 2-ButOH, 1.75 mM NAD, 80 mM TrisHCl pH 8.0, (10 mM TACA)) was then added and the formation of NADH was measured at 340 nm in the photometer. The results from the test are shown in FIGS. 5A and 5B. The $V_{max}$ values are shown.

FIGS. 5A and B shows that most of the mutants can no longer regenerate the cofactor or can only regenerate it very slowly (butanol test, dark bars). By adding TACA to the butanol test (pale bars), however, these mutants can regenerate the cofactor, and indeed better than the control (wildtype). Presumably here, instead of 2-butanol to 2-butanone, TACA is oxidized to TAC. These mutants tolerate larger amounts of TACA compared to the wildtype.

The missing mutants (for position T192 N, D, Q, H, K, M, F, Y and for position Y151 C, F, S) were detected, although these were not active or were worse than the control. The following mutants were selected from the experiments: Y151A, E, G, H and T192A, G, L, I, in order to test them on a larger scale.

1.6 Verification of the Positive Mutants

The positive clones emerging from this test were then investigated on a large scale (culture in 100 ml shaking flask). Here, three different assays were carried out:

Test 1) reduction of TAC to TACA with the addition of NADH

Test 2) complete reaction: reduction of TAC to TACA with cofactor regeneration by means of isopropanol

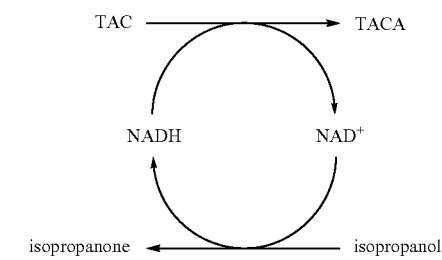

Test 3) oxidation of TACA to TAC

The test conditions for the individual tests are:

Test 1) reduction of TAC to TACA with the addition of NADH

| | |
|---|---|
| 798.6 µl | Demineralized water |
| 50 µl | 1M NaH$_2$PO$_4$ pH 5 |
| 50 µl | NADH (100 mM stock solution in water) |
| 1.4 µl | TAC |
| 100 µl | 10x crude extract concentrate of the culture from the shaking flask |
| 1000 µl | End volume |

Test 2) complete reaction

| | |
|---|---|
| 730 µl | Demineralized water |
| 50 µl | 1M NaH$_2$PO$_4$ pH 5 |
| 20 µl | NAD 10 mM in water |
| 100 µl | 100 mM TAC (14 µl in 1 ml isopropanol) |
| 100 µl | 10x crude extract concentrate of the culture from the shaking flask |
| 1000 µl | End volume |

Test 3) oxidation of TACA to TAC

| | |
|---|---|
| 798.6 µl | Demineralized water |
| 50 µl | 1M NaH$_2$PO$_4$ pH 5 |
| 50 µl | NAD (10 mM stock solution) |
| 1.4 µl | TACA |
| 100 µl | 10x crude extract concentrate of the culture from the shaking flask |
| 1000 µl | End volume |

In the above tests, the test temperature was in each case 30° C., the enzyme concentration was between 0.1-10 mg/ml.

The samples were stopped with concentrated HCl and measured by means of HPLC.

HPLC Conditions:

| Column: | Onyx Monolithic C18, 50 × 4.6 mm, Phenomenex |
|---|---|
| mob.Phase A: | 20 mM KH2PO4 pH 2.5 |
| mob.Phase B: | Acetonitrile |
| Inj.vol.: | 5 μl |
| Valve = | LeftColumn |
| TempCtrl = | On |
| Mode = | Combined |
| LeftTemperature.Nominal = | 45.00 [° C.] |
| LeftTemperatureDelta = | 0.80 [° C.] |
| LeftTemperature.LowerLimit = | −5.00 [° C.] |
| LeftTemperature.UpperLimit = | 80.00 [° C.] |
| Pressure.LowerLimit = | 2.0 [bar] |
| Pressure.UpperLimit = | 200.0 [bar] |
| MaximumFlowRamp = | 100.000 [ml/min$^2$] |
| %A.Equate = | % A |
| %B.Equate = | % B |
| CompressibilityLeftPump = | 50 [1/Mbar] |
| CompressibilityRightPump = | 115 [1/Mbar] |
| StrokeLeftPump = | Automatic |
| StrokeRightPump = | Automatic |
| SolventLeftPump = | A1 |
| SolventRightPump = | B1 |
| 3DFIELD.PeakWidth = | 0.05 [min] |
| 3DFIELD.SlitWidth = | 4 [nm] |
| UV_LampRequired = | Yes |
| Visible_LampRequired = | No |
| UV_VIS_1.Wavelength = | 230 [nm] |
| UV_VIS_1.Bandwidth = | 4 [nm] |
| UV_VIS_1.RefWavelength = | 400 [nm] |
| UV_VIS_1.RefBandwidth = | 80 [nm] |
| UV_VIS_1.Step = | Auto |
| UV_VIS_1.Average = | On |
| UV_VIS_2.Wavelength = | 260 [nm] |
| UV_VIS_2.Bandwidth = | 4 [nm] |
| UV_VIS_2.RefWavelength = | 400 [nm] |
| UV_VIS_2.RefBandwidth = | 80 [nm] |
| UV_VIS_2.Step = | Auto |
| UV_VIS_2.Average = | On |
| 3DFIELD.MinWavelength = | 190 [nm] |
| 3DFIELD.MaxWavelength = | 350 [nm] |
| 3DFIELD.BunchWidth = | 2.00 [nm] |

Retention times:
TACA=1.283 min (230 nm)
TAA=0.910 min (230 nm)
TA=1.168 min (260 nm)
TAC=1.540 min (260 nm)

The experimental results are summarized in the following section:

1.6.1 Mutants T192X

Figure 6A:
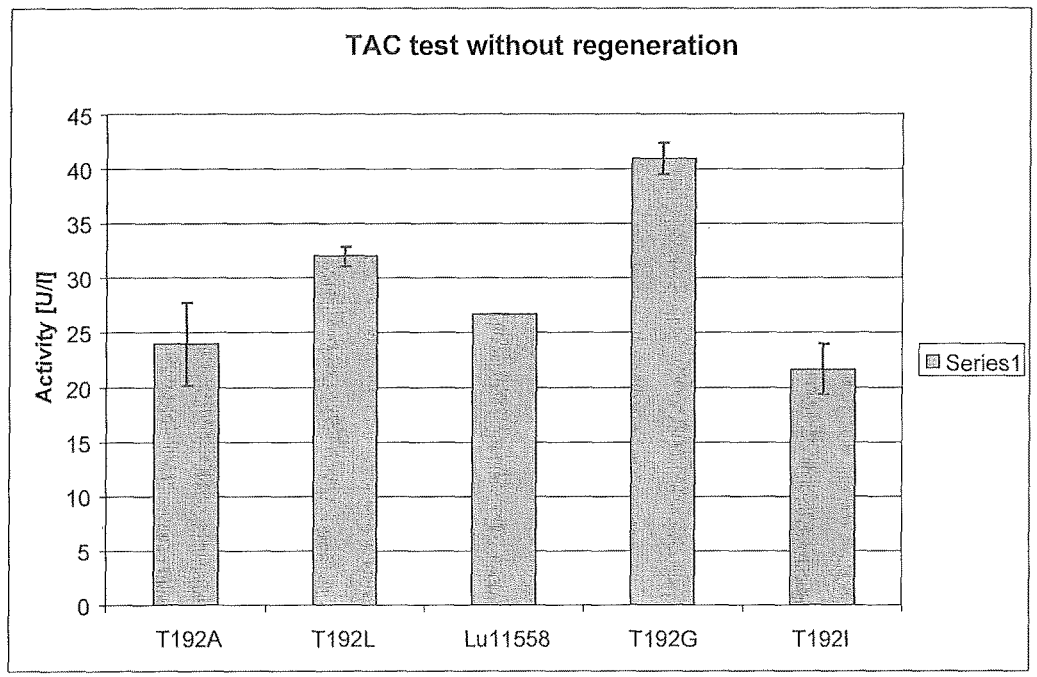
FIG. 6A shows the activity of various mutants of the type T192X in a TAC test without cofactor regeneration compared to the reference (LU11558).
Figure 6B:
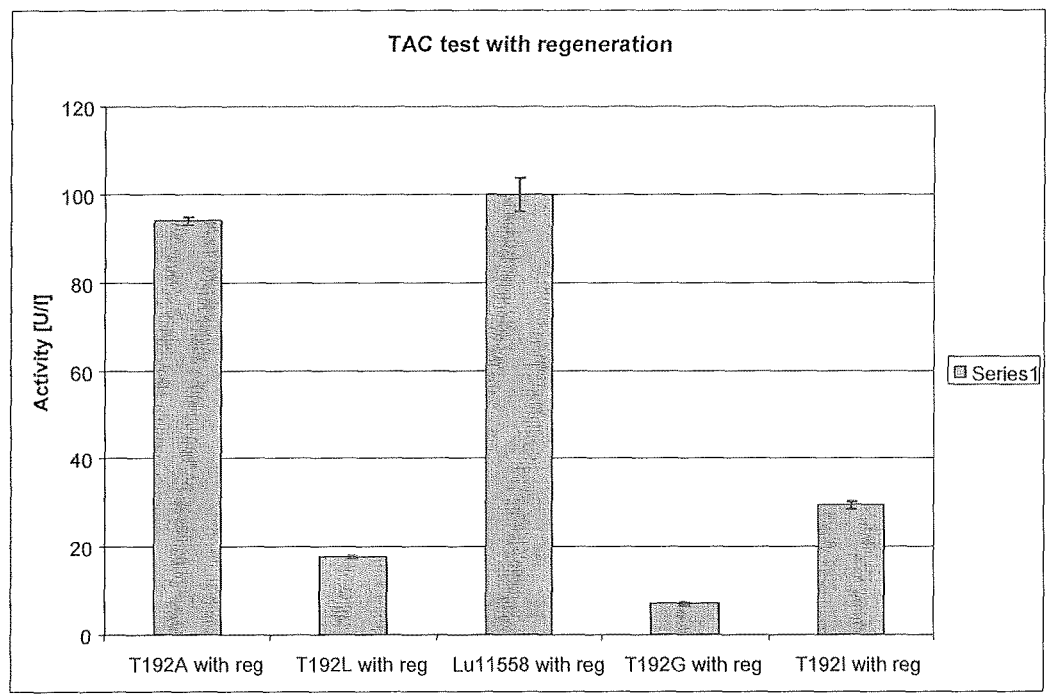
FIG. 6B shows the activity of various mutants of the type T192X in a TAC test with cofactor regeneration compared to the reference (LU11558).

FIG. 6A shows that the mutants T192L and T192G reduce TAC more rapidly than the control LU11558. However, if one considers the complete reaction (FIG. 6B), the wildtype is the most active since the other mutants cannot regenerate the cofactor as well.

Figure 6C:
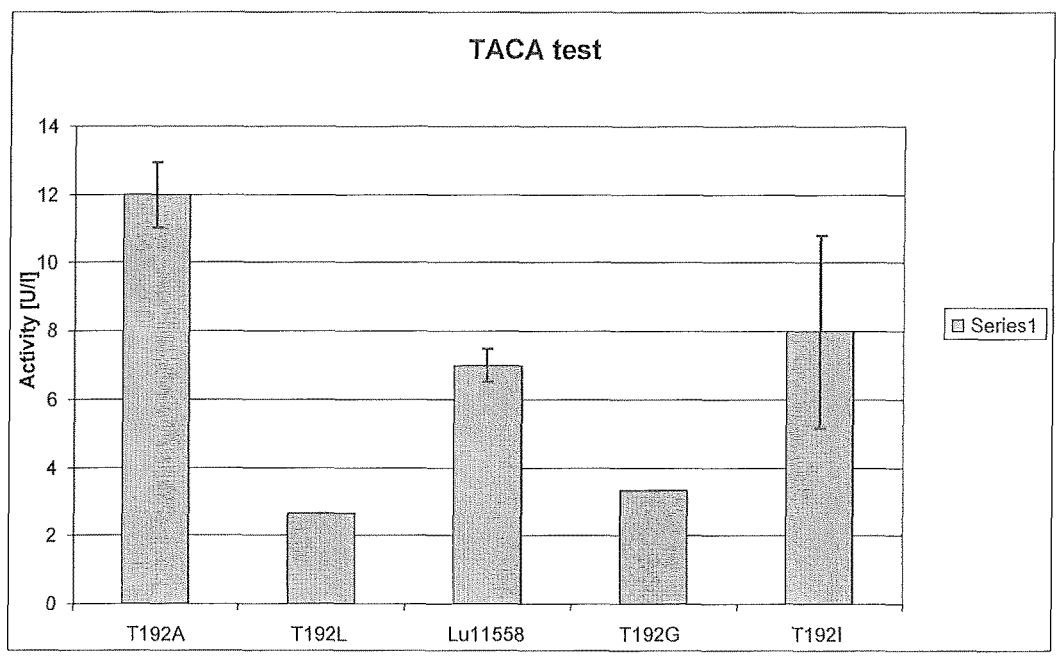
FIG. 6C shows the activity of various mutants of the type T192X in a TACA test compared to the reference (LU11558).

In FIG. 6C, it can be seen that the mutant T192A can better oxidize TACA than the wildtype, with the concentrations of TAC which form being very low and consequently the results fluctuating during the test.

1.6.2 Mutants Y151A

Figure 7A:
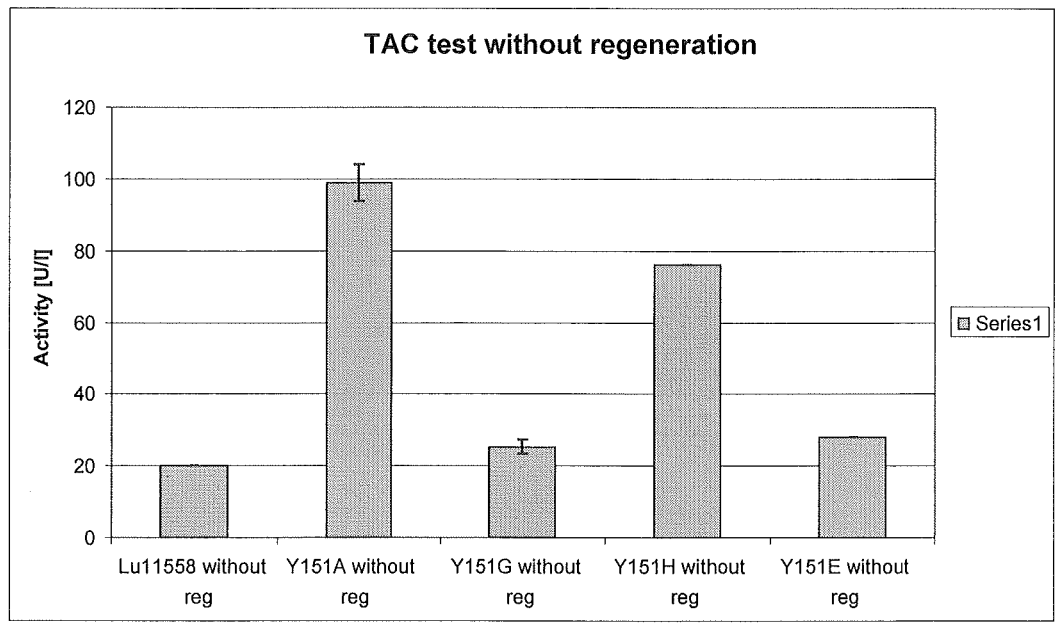
FIG. 7A shows the enzymatic activity of various mutants of the type Y151X in a TAC test without cofactor regeneration compared to the reference (LU11558).
Figure 7B:
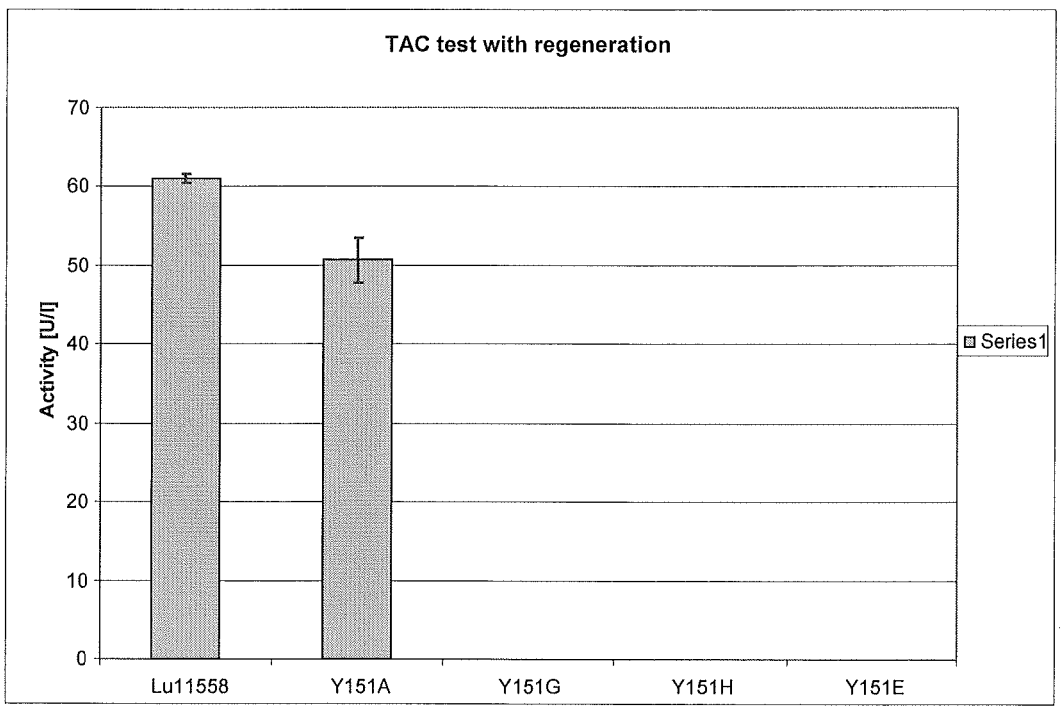
FIG. 7B shows the enzymatic activity of various mutants of the type Y151X in a TAC test with cofactor regeneration compared to the reference (LU11558).
Figure 7C:
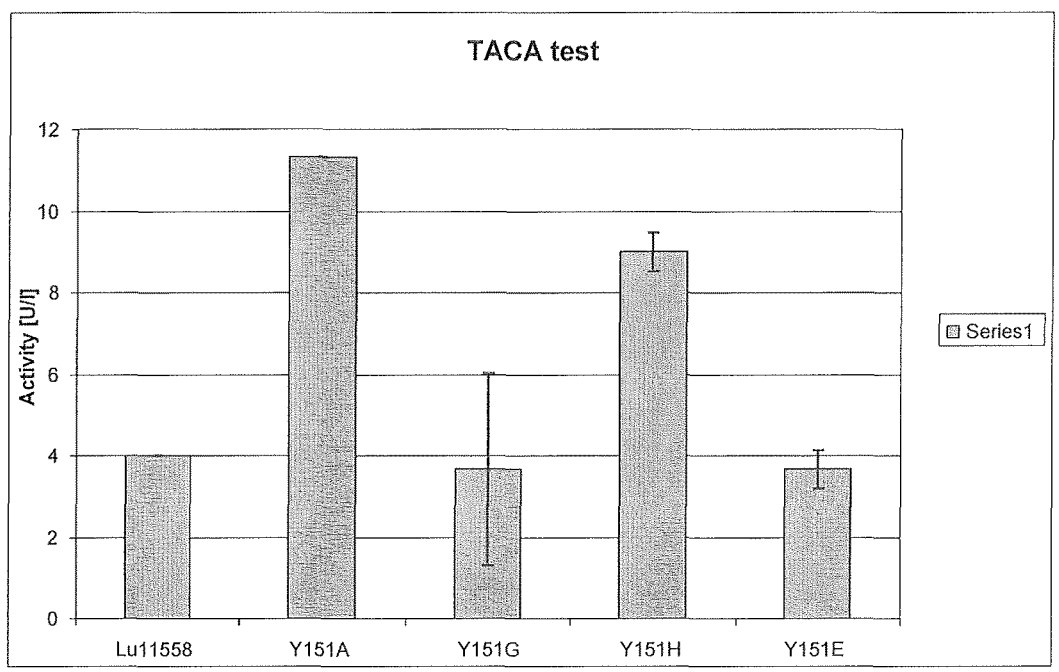
FIG. 7C shows the activity of various mutants of the type Y151X in a TAC test compared to the reference (LU11558).

In FIG. 7A it can be seen that the mutants Y151A and Y151H reduce the cofactor TAC approximately 4-5 times more rapidly than the wildtype (LU11558). However, if one considers the complete reaction, the reduction of TAC to TACA with regeneration of the cofactor by means of a sacrificial alcohol (here 2-propanol), then only the mutant Y151A is still active (FIG. 7B). The overall activity is somewhat lower than in the case of the control. As a result of enlarging the binding pocket, the "small" isopropanol possibly does not oxidize as well as 2-butanol, which is used in reactors. The mutants Y151A and Y151H can better oxide TACA than the wildtype (FIG. 7C).

The mutant Y151A was fermented on a 21 l scale and used in 4 l reactors with 2-butanol both as regeneration agent and also solvent in order to compare it with the wildtype.

1.6.3 Second Generation: Mutants Y151A-T192X

Since the mutant Y151A is better than the wildtype, building on this mutant, a second saturation mutagenesis was carried out at position T192X.

Figure 8A:
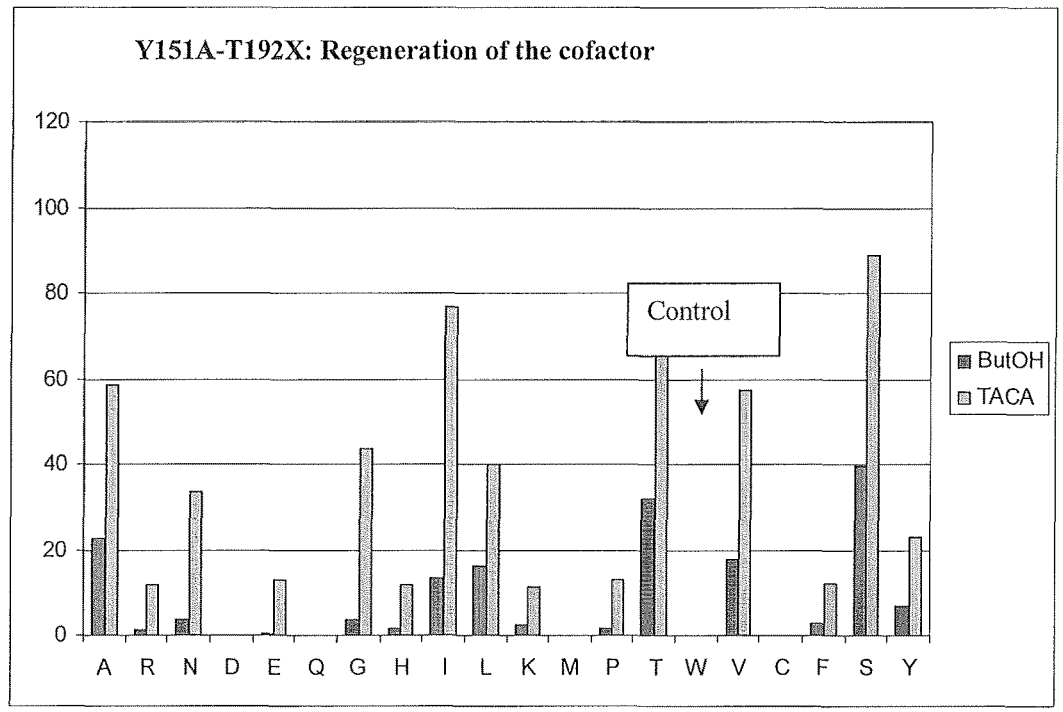
FIG. 8A illustrates the regeneration of the cofactor with 2-butanol in the presence and absence of TAC by mutants of the type Y151A-T192X.

The result of the regeneration test with 2-butanol (where the regeneration of the sacrificial alcohol with and without the addition of TACA is determined, i.e. the formation of NADH is measured in the photometer) is shown in FIG. 8A.

Figure 8B:
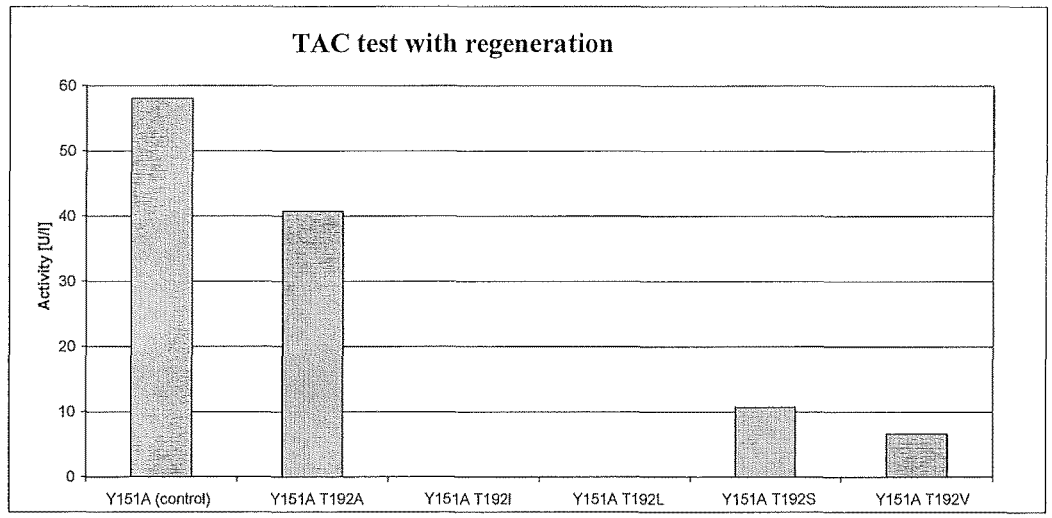
FIG. 8B illustrates the activity of mutants of the type Y151A-T192X in a TAC test with cofactor regeneration compared to the control (Y151A).

The mutants T192I and S come out better than the control (Y151A-T192T). These were therefore investigated on a larger scale (culture in 100 ml shaking flask). Furthermore, the mutants T192A, L and V were also investigated on a larger scale since these exhibit approximately the same activity as the control. However, if one considers the complete reaction of these five mutants, then the control is the most active (see FIG. 8B, where the formation of TACA with i-PropOH as sacrificial alcohol is measured by HPLC), and so the single mutant Y151A was used in the further experiments.

1.7 4 l Reactors

The more active mutant Y151A arising from this screening was fermented several times on the 21 l scale. A series of standard reactor batches was run in order to compare them on a larger scale with the control LU11558.

1.7.1 Batch:

In a heatable 4 l reactor fitted with stirrer and condenser, 2 l of 2-butanol were initially introduced in a 20 mM KH$_2$PO$_4$ buffer pH 5.0. 0.2 mM NAD (0.5 g) and 400 mM TAC (275 g) or 600 mM (420 g) were added. By adding the biocatalyst (450 ml, 7.0 g/l BTM) in the form of whole cells (untreated fermenter product), the reaction was started. Upon adding the cells in fermentation medium, the pH increased to 6. The two-phase reaction mixture was stirred at 40° C. and reduced pressure (110 mbar). Here, a mixture of 2-BuOH, 2-butanone and water was distilled off in one stage. At the same time, the equivalent amount of a solution consisting of 69% 2-butanol and 31% H$_2$O (corresponds to the composition of the distillate apart from 2-butanone) was added as feed. The pH was checked by means of a pH titrator and kept constant between pH~5.5-6.0. Every hour, a sample was taken, stopped with conc. HCl and analyzed by means of HPLC (LJ31366). After 8 h, the reaction mixture was let out.

1.7.2 Comparison of Wildtype (LU11558) with the Mutant Y151A (LU14759)

Several 4 l reactors of the mutant were run, firstly with 400 mM (~70 g/l) of TAC, then with 600 mM (105 g/l), in order to see whether the mutant tolerates larger amounts of product/secondary component.

Figure 9A:
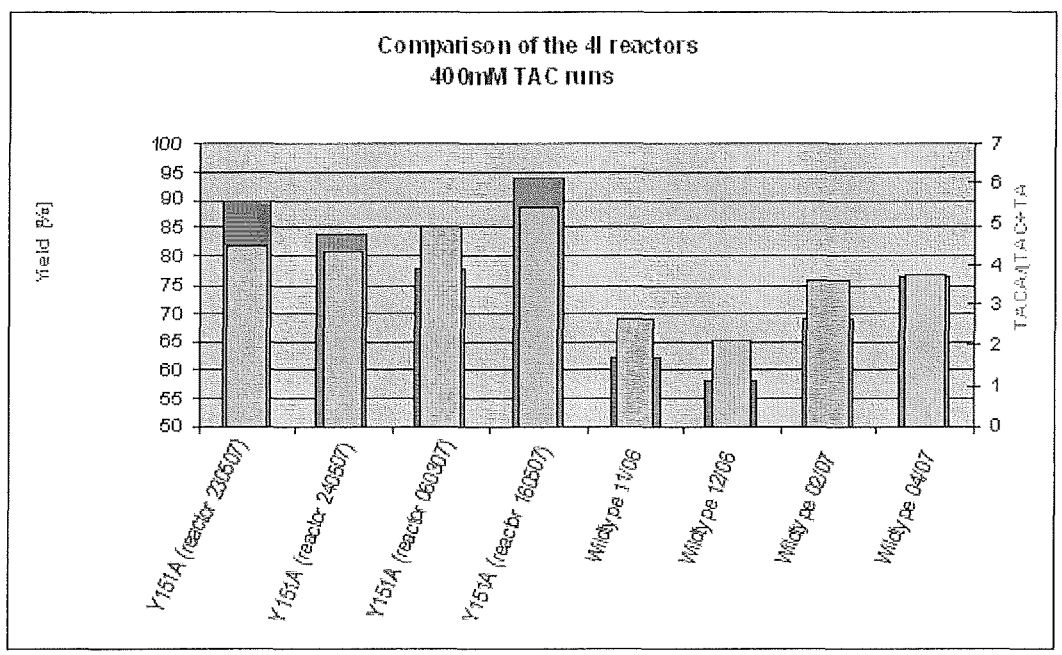
FIG. 9 illustrates the yields of TACA achieved with the help of the mutants Y151A in various reaction mixtures, in each case compared to the reference and as a function of different TAC concentrations (400 mM in FIGS. 9A and 600 mM in FIG. 9B).

FIG. 9A shows that the mutant is on average 15-20% better than the wildtype. As can be seen, the values fluctuate from experiment to experiment (this also depends on the individual fermentations), although the difference is significant. The average yield in the case of the wildtype is 67%±8% and in the case of the mutant is 86%±7%, these in each case being different fermentations. The ratio of TACA/(TAC+TA) (pale bars) is also significantly better in the case of the mutant (4.8) than in the case of the control (3.0), which becomes positively evident later in the methylamination.

Figure 9B:
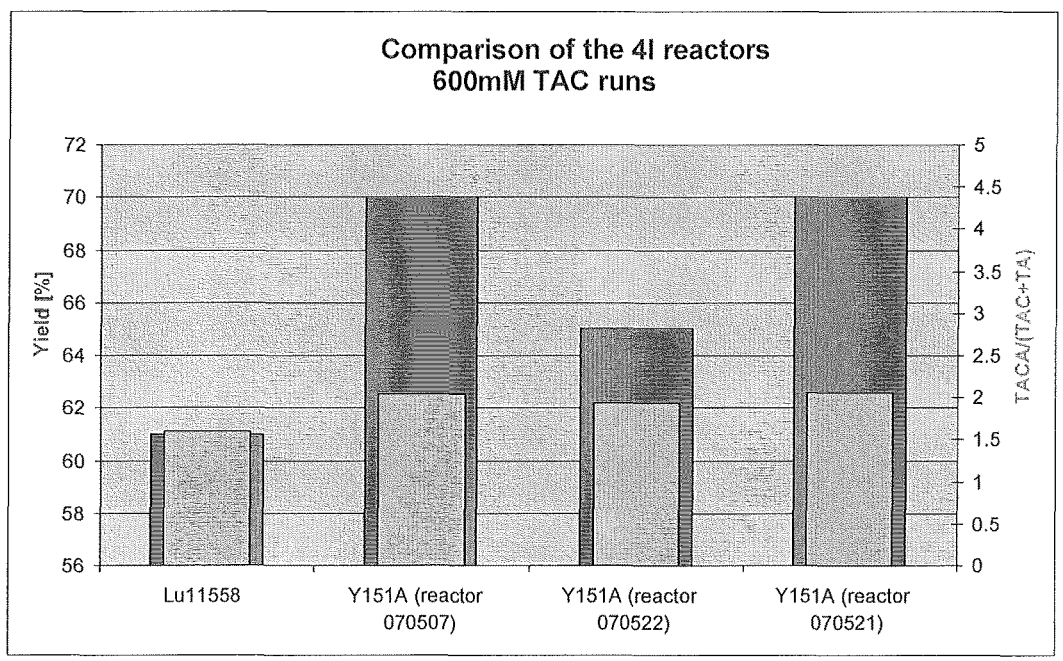

If one considers the runs with 600 mM TAC (FIG. 9B), then here too, the mutant produces better results than the control. However, the TACA/(TAC+TA) ratio is significantly worse than in the case of the 400 mM runs.

1.8 Result

Through rational design it has been possible to find a mutant Y151A (LU14759) which is 15%-20% more active than the wildtype (LU11558) and tolerates larger amounts of TACA and/or TA during the preparation of the intermediate of duloxetine alcohol.

This result has been confirmed in a series of 4 l standard reactors, which reflect the production process on a small scale.

Figure 10:
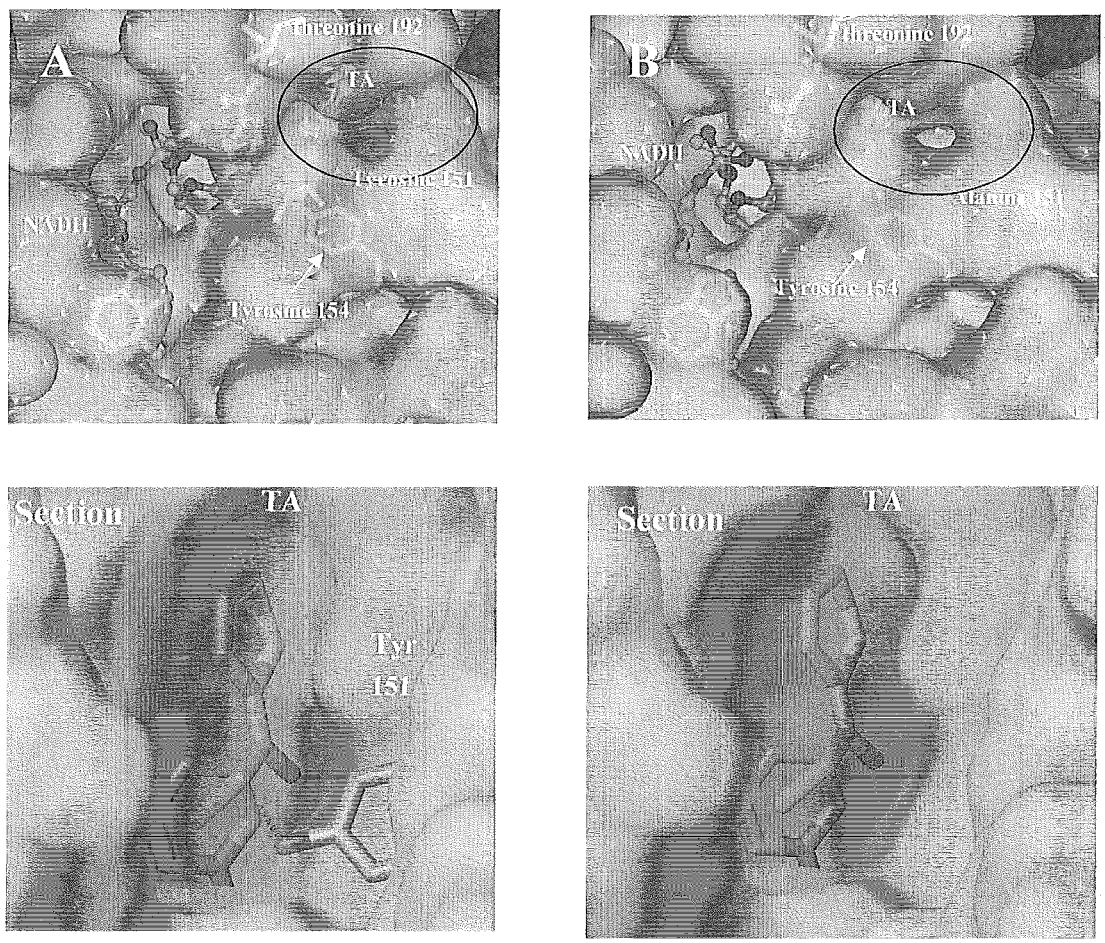
FIG. 10 illustrates, in a computer animated model, the substrate binding (TA) in wild-type enzyme EbN1 (synthesis A) or in mutant Y151A (synthesis B). The lower picture in each case depicts a magnified section from the substrate binding pocket.

Since the crystal structure of the enzyme has been resolved with the inhibitor TA it was possible to establish a reliable model of the enzyme-substrate complex. It is evident from the model that the OH group of the tyrosine 151 is in close contact with the β-carbon atom of the propanone side chain of the substrate (in this case TA) and thus forms a weak CH—O hydrogen bridge (FIG. 10A). As a result of the mutation of tyrosine 151 to alanine, this interaction is increased and the binding is weakened (FIG. 10B). All other interactions remain, meaning that the excellent selectivity of the enzyme is not altered despite the increase in the size of the binding pocket. Furthermore, the ee value of the product is >99.5%.

Example 2

Random Mutagenesis 2.1 Test Development for the Robot Installation

In order to deal with the large sample number which is produced by a random mutagenesis, it was necessary, instead of the hitherto HPLC analysis in the laboratory (in which the product is detected directly), to develop a photometric method for the robot production line.

For this, the reduction in the reduced cofactor NADH can be measured at 340 nm since the coefficient of extinction at this wavelength is $\epsilon_{NAD} \ll \epsilon_{NADH}$. The optimum NADH concentration was 0.02 mM. The substrate TAC could be used between 1 and 2 mM. The buffer used was 50 mM $NaH_2PO_4$ pH 5.0 since the reduction of TAC to TACA proceeds preferentially under slightly acidic conditions. The cells which express the mutants were cultured directly in a microtiter plate (MTP). For this, the clones were picked from the agar plate using a picking robot (Qpix) and inoculated into an LB preculture with antibiotics (100 μM ampicillin, 20 μM choramphenicol and 100 μM spectinomycin). After a growth time of 24 h at 37° C. and 200 rpm, the cells were transferred by hand into the LB main culture with antibiotics and inducers (Rhamnose 0.5 g/l and IPTG 0.1 mM). After growth for 16-18 h, the cells were used in the test.

Preliminary experiments have shown that the cells from the culture must be disrupted prior to the assay since the activity is otherwise too low. For disruption of the cells, various methods were tested, such as, for example, storage of the cells overnight at 4° C., the addition of 1-butanol and 1,4-butanediol and rapid freezing with liquid nitrogen. Only storage at 4° C. and rapid freezing with liquid nitrogen were successful, treatment with nitrogen being preferred on account of the time saving. For this purpose, the grown cells were firstly centrifuged, the supernatant was pulled off and the MTP was closed with an adhesive film. The MTP was immersed completely in liquid nitrogen for ca. 3 seconds and then set down again to thaw. The most uniform results were achieved in the case of 4-fold rapid freezing with interim thawing at room temperature.

2.2 Course of the Robot Test

The cells were cultured as described above and then disrupted. The MTP were provided with covers and placed in the incubator at 15° C. into the robot installation. In the Multidrop, 100 μl/well of water were added in order to then resuspend the cells in the Packard. Then, in the Multidrop, the substrate solution (end concentrations: 2 mM TAC, 0.2 mM NADH, 50 mM $NaH_2PO_4$ pH 5.0) was added and the NADH decrease was determined at 340 nm in the photometer.

The positive clones arising from this test were then investigated more thoroughly on a larger scale. For this, three different assays were carried out.

Test A complete reaction: reduction of TAC to TACA and NADH regeneration with isopropanol (50 mM $NaH_2PO_4$ pH 5.0, 0.2 mM NAD, 10 mM TAC, 10% isopropanol), measurement HPLC LJ31366

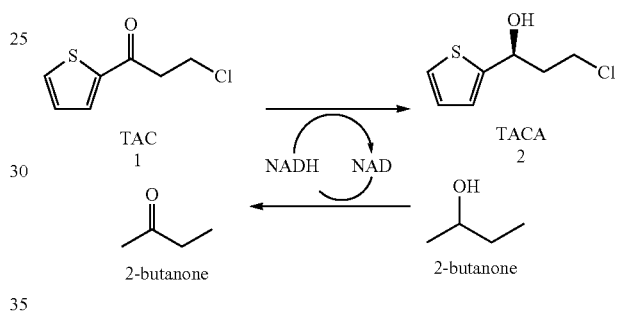

Test B regeneration of NAD to NADH with 2-butanol as regenerating agent (80 mM TrisHCl pH 8.0, 100 mM 2-butanol, 1.75 mM NAD) in the photometer

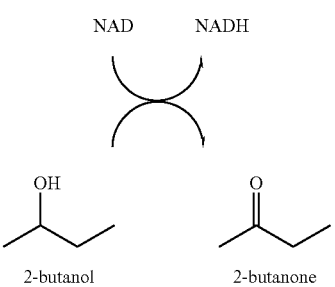

Test C Reduction of TAC to TACA with the addition of NADH (50 mM $NaH_2PO_4$ pH 5.0, 0.2 mM NADH, 1.4 μl TAC pure (10 mM)) in the photometer

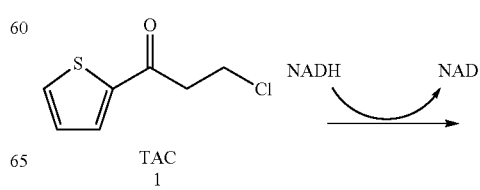

-continued

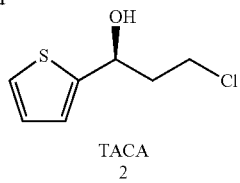

TACA
2

A comparison of the results from the three assays revealed that the regeneration of NAD (i.e. test B) reflect the results of the complete reaction significantly better than the reduction of TAC to TACA initially used in the robot test.

Preliminary experiments likewise indicated that the regeneration of the cofactor with 2-butanol (thus the formation of NADH) takes place only in the case of cells which express the biocatalyst. Consequently, the robot test was switched to the detection of the NADH regeneration with 2-butanol. In parallel to this, however, the reduction of TAC to TACA, thus the decrease in NADH, was still measured.

2.3 Course of the Modified Robot Test

The cells were cultured and then disrupted. The MTP were provided with covers and placed in the incubator at 15° C. in the robot installation. In the Multidrop, 100 µl/well of water were added in order to then resuspend the cells. From these, two daughter plates with 20 µl/well (for assay: regeneration of the cofactor) or 70 µl/well (for assay: reduction of TAC) of cell suspension were produced. The substrate solutions (end concentrations: reduction: 2 mM TAC, 0.2 mM NADH, 50 mM NaH$_2$PO$_4$ pH 5.0; regeneration: 100 mM 2-butanol, 1.75 mM NAD, 80 mM TrisHCl pH 8.0) were added and the formation of NADH was determined at 340 nm in the photometer.

2.4 Evaluation of the Robot Test Results

In the robot screening, the formation/decrease (reduction/oxidation) of NADH was determined photometrically. For this, in each case 10 measurement values were ascertained over 10 min. By calculating the increase from these values, the starting activity of the dehydrogenase was determined.

2.5 Inhibition of the Enzyme Reaction

Preliminary experiments had shown that the product TACA or a secondary component which is formed during the reaction inhibit the reaction. The substrate was not completely converted.

It was thus an aim to find a mutant which tolerates not only more active, but also larger amounts of product or secondary component in order to achieve as complete a conversion as possible and thus a high space-time yield.

For this reason, TACA was added in the assay. For this, a further 10 mM TACA is added to the regeneration test carried out hitherto with 2-butanol and NAD.

On account of the limited biomass, it was not possible to carry out all three tests in parallel in the robot screening. Consequently, the reduction reaction of TAC to TACA was omitted. The regeneration reaction of NADH with 2-butanol remained unchanged. The TAC solution was replaced by a substrate solution for the TACA inhibition (100 mM 2-butanol, 1.75 mM NAD, 10 mM TACA, 80 mM TrisHCl pH 8.0). The course of the robot test remained unchanged.

The evaluation was adapted accordingly to the measurement of the TACA inhibition.

2.6 Preparation of the Mutant Library: Random Mutagenesis on EbN1 Gene

In order to produce mutations in the sequence coding for the dehydrogenase, an error-prone PCR reaction (error-prone polymerase chain reaction) was carried out with the addition of MnCl$_2$. With MnCl$_2$ the specificity of the Taq-DNA polymerase used was reduced, as a result of which, as the MnCl$_2$ concentration increases, more incorrect nucleotides are incorporated and accordingly more mutations are generated.

For the PCR, the following oligonucleotides with cloning cleavage sites (NdeI-Hind III) were selected which cover the shortest possible region of the DNA so that mutations could also arise in the starting and end regions:

```
Mke123
5'-GTTCATCTTTCCCTGGTTG-3'      (SEQ ID NO: 13)

Mke124
5'-GCTACGGCGTTTCACTTC-3'       (SEQ ID NO: 14)
```

Batch:

In 50 µl PCR batch: 50 ng plasmid DNA (pDHE-ebn1H) with dehydrogenase gene, in each case 120 ng oligonucleotide, GCRich-reaction buffer 1× (Roche), ⅕ vol GCRich resolution (Roche), in each case 0.2 mM dATP, dTTP, dCTP, dGTP, 1 U Taq DNA polymerase.

This batch was heated at 95° C. for 5 min (initial denaturation of the DNA) and then cooled to 85° C. At this temperature, MnCl$_2$ was added in various concentration (from 0-1 mM in 0.02 mM steps). This was necessary so that the MnCl$_2$ dissolves completely. The actual PCR was then started using the following temperature program: 4 cycles: 95° C. for 45 sec, 54° C. for 45 sec, 72° C. for 45 sec; then 26 cycles: 95° C. for 45 sec, 58° C. for 45 sec, 72° C. for 45 sec; 10° C. pause.

The PCR products were purified on an agarose gel (Gfx kit) and then a restriction cleavage with the enzymes NdeI and HindIII (both from NEB) was carried out. Following ligation into the vector pDHE (likewise NdeI/HindIII cleaved), the transformation was carried out into XL10 ultracompetent cells from Stratagene. The best MnCl$_2$ concentration was then determined by sequencing some of the clones (16 clones per concentration). In this connection, further work was carried out with the MnCl$_2$ concentration which produced between 1-3 base pair exchanges. For this, the ligation batch was firstly transformed into XL10 competent cells, the clones were counted and then all of the clones were eluted from the agar plate with LB medium. The plasmid DNA was isolated (Promega kit) without further incubation of the cells and the DNA isolated in this way was transformed into the production strain TG10, which also coexpresses the chaperone pAgro pHSG, and plated out onto Q-tray plates. This procedure was necessary because the transformation rate of the production strain TG10+ (LU12037) during ligations was very low, and as many mutants as possible were desired.

2.7 Selected Mutants

Table 1 above gives an overview of the clones selected from the robot test. These clones originate from the verification plates which have been completely sequenced. These were cultured on a larger scale and firstly tested in the Eppendorf. Here, however, the activity of most of the mutants was comparable with the wildtype. The more active mutants, for example K114T and M200V F201L, were fermented on a 21 l scale and tested in a 0.5 l reactor.

In a heatable 0.5 l reactor fitted with stirrer and condenser, 250 ml of 2-butanol were initially introduced in a 20 mM KH$_2$PO$_4$ buffer pH 5.0. 0.2 mM NAD (0.1 g) and 400 mM TAC (35 g) were added. By adding the biocatalyst (45 ml, 5.5 g/l BTM) in the form of whole cells (untreated fermenter product), the reaction was started. Upon adding the cells in fermentation medium, the pH increased to 6. The two-phase reaction mixture was stirred at 40° C. under reduced pressure (110 mbar). Here, a mixture of 2-butOH, 2-butanone and water was distilled off in one stage. At the same time, the equivalent amount of a solution consisting of 69% 2-butanol and 31% H₂O (corresponds to the composition of the distillate with the exception of 2-butanone) was added as feed. The pH was checked using a pH titrator and kept constant between pH~5.5-6.0. Every hour, a sample was taken, stopped with conc. HCL and analyzed by means of HPLC (LJ31366). After 8 h, the reaction mixture was let out.

Error analysis of the individual steps shows that the greatest error is in the growth of the individual clones in the microtiter plate. This is not surprising since the growth conditions (temperature, oxygen introduction, etc.) in the microtiter plate cannot be controlled as exactly as in a fermenter. Even different fermentations of the same strain fluctuate by ca. 10%-15%. The overall error for this robot screening is about 35%. I.e. in this screening only mutants which exhibit an increase of more than 35% are meaningful.

Example 3

Site-Directed Mutagenesis and Further Saturation Mutageneses

Single mutations ("site-directed mutagenesis") or saturation mutageneses which have been tested were carried out on further targeted selected positions.

3.1 Selection of the Positions for a Mutation

The substrate binding pocket of the enzyme is formed by loop 1, 2 and the helix αFG1 (cf. FIG. 2). Most mutations were selected from this region since these amino acids can be expected to have a direct effect on the substrate binding and/or activity of the enzyme.

The helix is very flexible without substrate (in the crystal no electron density is visible) and only becomes fixed upon substrate binding. The active center with the substrate binding pocket can be divided into a hydrophobic and hydrophilic region. The hydrophobic part is formed predominantly by the amphiphilic helix αFG1 which, after substrate binding, sits like a lid on the substrate binding pocket. The amino acids 192 to 204 are within this region. The side chains of the amino acids Thr192, Leu197, Met200 and Leu204 point into the binding pocket whereas amino acid Phe201 serves to stabilize the loop. Threonine 192 with its OH group forms the boundary between the hydrophobic and hydrophilic region of the active center. Leu186 sits at the start of the flexible helix and serves as a hinge for the opened and closed state of the active center. Methionine 246 sits at the end of the substrate binding pocket. The other side of the substrate binding pocket forms the loop βEαF with the amino acids 146 to 151. Here too, the side chains of the selected amino acids Leu146, Ile148 and Tyr151 point into the binding pocket. The terminal OH group of the Tyrosine 151 is part of the hydrogen bridge network of the hydrophilic part of the active center whereas the remainder of the side chain belongs to the hydrophobic part. The predominantly hydrophilic underside of the active center forms a strand of the amino acids 138-142, here the amino acids Leu139, Thr140 and Thr142 have been mutated. The two Cysteines 62 and 83 were selected for a mutation since cysteines generally are oxidation-sensitive and can thereby have an adverse effect on the structure.

Figure 11:
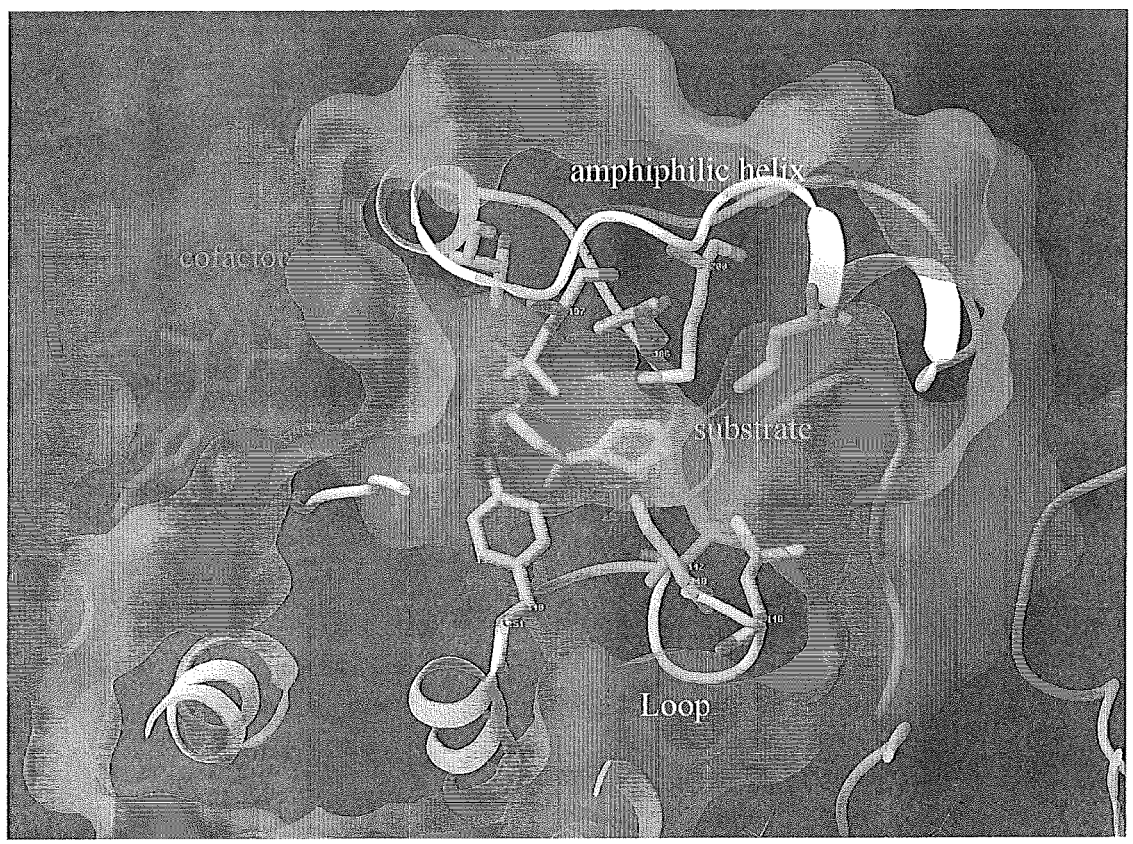
FIG. 11 shows a computer simulated depiction of a section from the active center of EbN1; here, the arrangement of the amphiphilic helix, of loop 2, of the substrate and of the cofactor (NADH) are emphasized.

FIG. 11 shows a section from the active center. The cofactor is marked in violet, the substrate (here TA) in green, the mutated amino acids are emphasized. In the upper region, the amphiphilic helix αFG1 can be seen and, in the lower region, the loop βEαF (loop 2).

3.2 Preparation of the Targeted Mutants

Figure 12:
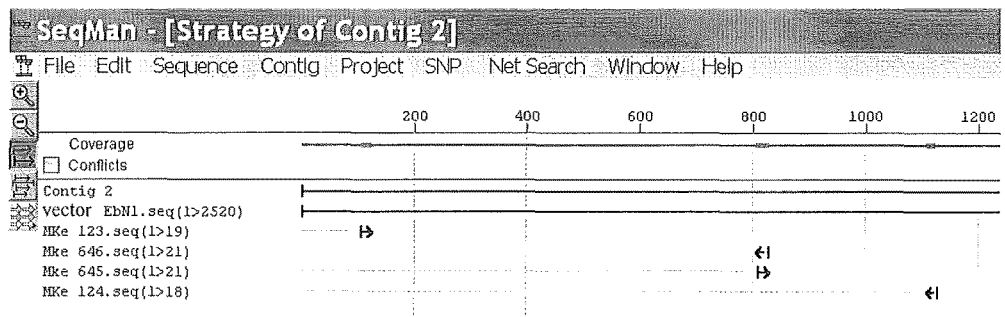
FIG. 12 illustrates the cloning strategy for a site-directed mutagenesis.

Firstly, for the respective position of the DNA mutation, two complementary oligonucleotides (see table 3) were selected which corresponded to the desired DNA sequence. Additionally, two further oligonucleotides (Mke123 and Mke124, SEQ ID NO:5 and 6), which flank the whole gene, were also selected. The cloning strategy for the site-directed mutagenesis is shown in FIG. 12.

Two PCR reactions were then carried out, each with an oligonucleotide flanking the gene and one which carries the desired mutation. These give two PCR products which, instead of the mutation, have a short complementary region. Using these two PCR products as templates, a second PCR was carried out, again using the gene-flanking oligonucleotides used previously. This reaction gives the complete gene with the desired mutation.

The PCR product was cleaved with the restriction enzymes NdeI and HindIII and then ligated into pDHE vector. Following successful transformation into the competent cells XL10 Gold (Stratagene) and subsequent plasmid isolation, the plasmids were sequenced in order to confirm the successful mutation. To determine the activity, the plasmids were transformed into TG10+ competent cells which comprise the chaperone plasmids pAgro and pHSG (LU12037).

TABLE 3

Oligonucleotide sequences for the preparation of the individual mutants
Single mutations

| Mutation | Oligo name | Sequence 5'→3' | Sequence No. |
|---|---|---|---|
| L139A | Mke 579 | CATCATCAACGCGACTTCGA | SEQ ID NO: 13 |
| | Mke 580 | TCGAAGTCGCGTTGATGATG | SEQ ID NO: 14 |
| L146M | Mke 606 | CGACATATTGGATGAAGATCGAGG | SEQ ID NO: 15 |
| | Mke 607 | CCTCGATCTTCATCCAATATGTCG | SEQ ID NO: 16 |
| I148V | Mke 577 | CATATTGGCTAAAGGTGGAGGCG | SEQ ID NO: 17 |
| | Mke 578 | CGCCTCCACCTTTAGCCAATATG | SEQ ID NO: 18 |
| Y151A | Mke 949 | TCGAGGCGGCGACCCATTAC | SEQ ID NO: 19 |
| | Mke 950 | GTAATGGGTCGCCGCCTCGA | SEQ ID NO: 20 |
| C62A | Mke 569 | CGTGAAGGCGGATGTCTCG | SEQ ID NO: 21 |
| | Mke 570 | CGAGACATCCGCCTTCACG | SEQ ID NO: 22 |
| C62S | Mke 571 | CGTGAAGAGCGATGTCTCG | SEQ ID NO: 23 |
| | Mke 572 | CGAGACATCGCTCTTCACG | SEQ ID NO: 24 |
| C83A | Mke 573 | CCACGTTTGGTCGCGCGGACATCC | SEQ ID NO: 25 |
| | Mke 574 | GGATGTCCGCGCGACCAAACGTGG | SEQ ID NO: 26 |
| C83S | Mke 575 | GTTTGGTCGCAGCGACATC | SEQ ID NO: 27 |
| | Mke 576 | GATGTCGCTGCGACCAAAC | SEQ ID NO: 28 |
| T140A | Mke 587 | CATCAACCTGGCGTCGACGAC | SEQ ID NO: 29 |
| | Mke 588 | GTCGTCGACGCCAGGTTGATGAT | SEQ ID NO: 30 |
| T140S | Mke 589 | CAACCTGAGCTCGACGACATATT | SEQ ID NO: 31 |
| | Mke 590 | AATATGTCGTCGAGCTCAGGTTG | SEQ ID NO: 32 |
| T140G | Mke 618 | CATCATCAACCTGGGCTCGACGAC | SEQ ID NO: 33 |

TABLE 3-continued

Oligonucleotide sequences for the preparation of the individual mutants
Single mutations

| Mutation | Oligo name | Sequence 5'→3' | Sequence No. |
|---|---|---|---|
| | Mke 619 | GTCGTCGAGCCCAGGTTGATGATG | SEQ ID NO: 34 |
| T142L | Mke 620 | CAACCTGACTTCGCTGACATATTG | SEQ ID NO: 35 |
| | Mke 621 | CAATATGTCAGCGAAGTCAGGTTG | SEQ ID NO: 36 |
| T142S | Mke 622 | CAACCTGACTTCGAGCACATATTG | SEQ ID NO: 37 |
| | Mke 623 | CAATATGTGCTCGAAGTCAGGTTG | SEQ ID NO: 38 |
| T142A | Mke 626 | CAACCTGACTTCGGCGACATATTG | SEQ ID NO: 39 |
| | Mke 627 | CAATATGTCGCCGAAGTCAGGTTG | SEQ ID NO: 40 |
| T142G | Mke 628 | CAACCTGACTTCGGGCACATATTG | SEQ ID NO: 41 |
| | Mke 629 | CAATATGTGCCCGAAGTCAGGTTG | SEQ ID NO: 42 |
| L186G | Mke 649 | CGCCGAGCCGCGTCCGCACG | SEQ ID NO: 43 |
| | Mke 650 | CGTGCGGACGCGGCTCGGCG | SEQ ID NO: 44 |
| L186A | Mke 651 | CGCCGAGCGCAGTCCGCACG | SEQ ID NO: 45 |
| | Mke 652 | CGTGCGGACTGCGCTCGGCG | SEQ ID NO: 46 |
| L197A | Mke 583 | GCGTCCGCGATGTTCGACGTG | SEQ ID NO: 47 |
| | Mke 584 | CGAACATCGCGGACGCTGCAG | SEQ ID NO: 48 |
| L197I | Mke 645 | ATTTCCGCGATGTTCGACGTG | SEQ ID NO: 49 |
| | Mke 646 | CGAACATCGCGGAAATTGCAG | SEQ ID NO: 50 |
| L204A | Mke 608 | GTTCGACGTGGCGCCAAACATGC | SEQ ID NO: 51 |
| | Mke 609 | GCATGTTTGGCGCCACGTCGAAC | SEQ ID NO: 52 |
| L204V | Mke 610 | GTTCGACGTGGTGCCAAACATGC | SEQ ID NO: 53 |
| | Mke 611 | GCATGTTTGGCACCACGTCGAAC | SEQ ID NO: 54 |
| M246A | Mke 612 | ATGGCGGTGCGGTGAGACACTAA | SEQ ID NO: 55 |
| | Mke 613 | TTAGTGTCTCACCGCACCGCCAT | SEQ ID NO: 56 |
| M246L | Mke 614 | ATGGCGGTATTGTGAGACACTAA | SEQ ID NO: 57 |
| | Mke 615 | TTAGTGTCTCACAATACCGCCAT | SEQ ID NO: 58 |
| M246V | Mke 616 | ATGGCGGTGTGGTGAGACACTAA | SEQ ID NO: 59 |
| | Mke 617 | TTAGTGTCTCACCACACCGCCAT | SEQ ID NO: 60 |

Saturation Mutageneses:

| Mutation | Oligoname | Sequence 5'→3' | | Sequence No. |
|---|---|---|---|---|
| T192X | Mke 796 | ACGGCAACANNNGAAGCGTC | | SEQ ID NO: 9 |
| | Mke 797 | GACGCTTCNNNTGTTGCCGT | | SEQ ID NO: 10 |
| L197X | Mke 845 | GCGTCTGCANNNTCCGCGATGTTC | | SEQ ID NO: 61 |
| | Mke 846 | CGAACATCGCGGANNNTGCAGACG | | SEQ ID NO: 62 |
| M200X | Mke 915 | CGTCGAAGCACGCGGACAATG | ebn1H M200Y 5' | SEQ ID NO: 63 |
| | Mke 916 | CGTCGAAATACGCGGACAATG | ebn1H M200Y 3' | SEQ ID NO: 64 |
| | Mke 917 | GTCCGCGTGGTTCGACGTGCT | ebn1H M200W 5' | SEQ ID NO: 65 |
| | Mke 918 | CGTCGAACCACGCGGACAATG | ebn1H M200W 3' | SEQ ID NO: 66 |
| | Mke 919 | GTCCGCGGTGTTCGACGTGCT | ebn1H M200V 5' | SEQ ID NO: 67 |
| | Mke 920 | CGTCGAACACCGCGGACAATG | ebn1H M200V 3' | SEQ ID NO: 68 |
| | Mke 921 | GTCCGCGACCTTCGACGTGCT | ebn1H M200T 5' | SEQ ID NO: 69 |
| | Mke 922 | CGTCGAAGGTCGCGGACAATG | ebn1H M200T 3' | SEQ ID NO: 70 |
| | Mke 923 | GTCCGCGAGCTTCGACGTGCT | ebn1H M200S 5' | SEQ ID NO: 71 |
| | Mke 924 | CGTCGAAGCTCGCGGACAATG | ebn1H M200S 3' | SEQ ID NO: 72 |
| | Mke 925 | GTCCGCGCGCTTCGACGTGCT | ebn1H M200R 5' | SEQ ID NO: 73 |
| | Mke 926 | CGTCGAAGCGCGCGGACAATG | ebn1H M200R 3' | SEQ ID NO: 74 |
| | Mke 927 | GTCCGCGCAGTTCGACGTGCT | ebn1H M200Q 5' | SEQ ID NO: 75 |

-continued

| Mutation | Oligoname | Sequence 5'→3' | | Sequence No. |
|---|---|---|---|---|
| | Mke 928 | CGTCGAACTGCGCGGACAATG | ebn1H M200Q 3' | SEQ ID NO: 76 |
| | Mke 929 | GTCCGCGCCGTTCGACGTGCT | ebn1H M200P 5' | SEQ ID NO: 77 |
| | Mke 930 | CGTCGAACGGCGCGGACAATG | ebn1H M200P 3' | SEQ ID NO: 78 |
| | Mke 931 | GTCCGCGCTGTTCGACGTGCT | ebn1H M200L 5' | SEQ ID NO: 79 |
| | Mke 932 | CGTCGAACAGCGCGGACAATG | ebn1H M200L 3' | SEQ ID NO: 80 |
| | Mke 933 | GTCCGCGAAATTCGACGTGCT | ebn1H M200K 5' | SEQ ID NO: 81 |
| | Mke 934 | CGTCGAATTTCGCGGACAATG | ebn1H M200K 3' | SEQ ID NO: 82 |
| | Mke 935 | GTCCGCGATCTTCGACGTGCT | ebn1H M200I 5' | SEQ ID NO: 83 |
| | Mke 936 | CGTCGAAGATCGCGGACAATG | ebn1H M200I 3' | SEQ ID NO: 84 |
| | Mke 937 | GTCCGCGCATTTCGACGTGCT | ebn1H M200H 5' | SEQ ID NO: 85 |
| | Mke 938 | CGTCGAAATGCGCGGACAATG | ebn1H M200H 3' | SEQ ID NO: 86 |
| | Mke 939 | GTCCGCGGGCTTCGACGTGCT | ebn1H M200G 5' | SEQ ID NO: 87 |
| | Mke 940 | CGTCGAAGCCCGCGGACAATG | ebn1H M200G 3' | SEQ ID NO: 88 |
| | Mke 941 | GTCCGCGTTCTTCGACGTGCT | ebn1H M200F 5' | SEQ ID NO: 89 |
| | Mke 942 | CGTCGAAGAACGCGGACAATG | ebn1H M200F 3' | SEQ ID NO: 90 |
| | Mke 943 | GTCCGCGGAATTCGACGTGCT | ebn1H M200E 5' | SEQ ID NO: 91 |
| | Mke 944 | CGTCGAATTCCGCGGACAATG | ebn1H M200E 3' | SEQ ID NO: 92 |
| | Mke 945 | GTCCGCGGATTTCGACGTGCT | ebn1H M200D 5' | SEQ ID NO: 93 |
| | Mke 946 | CGTCGAAATCCGCGGACAATG | ebn1H M200D 3' | SEQ ID NO: 94 |
| | Mke 947 | GTCCGCGTGCTTCGACGTGCT | ebn1H M200C 5' | SEQ ID NO: 95 |
| | Mke 948 | GTCCGCGTATTTCGACGTGCT | ebn1H M200Y 5' | SEQ ID NO: 96 |
| | Mke 647 | GTCCGCGAACTTCGACGTGCT | ebn1 M200N 5' | SEQ ID NO: 97 |
| | Mke 648 | CGTCGAAGTTCGCGGACAATG | ebn1 M200N 3' | SEQ ID NO: 98 |
| | Mke 585 | GTCCGCGGCGTTCGACGTGCT | ebn1 M200A 5' | SEQ ID NO: 99 |
| | Mke 586 | CGTCGAACGCCGCGGACAATG | ebn1 M200A 3' | SEQ ID NO: 100 |
| F201X | Mke 653 | GTCCGCGATGTATGACGTGCTGC | ebn1 F201Y | SEQ ID NO: 101 |
| | Mke 654 | GCAGCACGTCATACATCGCGGAC | ebn1 F201Y | SEQ ID NO: 102 |
| | Mke 655 | GTCCGCGATGTGGGACGTGCTGC | ebn1 F201W | SEQ ID NO: 103 |
| | Mke 656 | GCAGCACGTCCCACATCGCGGAC | ebn1 F201W | SEQ ID NO: 104 |
| | Mke 657 | GTCCGCGATGACTGACGTGCTGC | ebn1 F201T | SEQ ID NO: 105 |
| | Mke 658 | GCAGCACGTCAGTCATCGCGGAC | ebn1 F201T | SEQ ID NO: 106 |
| | Mke 659 | GTCCGCGATGTCGGACGTGCTGC | ebn1 F201S | SEQ ID NO: 107 |
| | Mke 660 | GCAGCACGTCCGACATCGCGGAC | ebn1 F201S | SEQ ID NO: 108 |
| | Mke 661 | GTCCGCGATGCGTGACGTGCTGC | ebn1 F201R | SEQ ID NO: 109 |
| | Mke 662 | GCAGCACGTCACGCATCGCGGAC | ebn1 F201R | SEQ ID NO: 110 |
| | Mke 663 | GTCCGCGATGCAGGACGTGCTGC | ebn1 F201Q | SEQ ID NO: 111 |
| | Mke 664 | GCAGCACGTCCTGCATCGCGGAC | ebn1 F201Q | SEQ ID NO: 112 |
| | Mke 665 | GTCCGCGATGCCGGACGTGCTGC | ebn1 F201P | SEQ ID NO: 113 |
| | Mke 666 | GCAGCACGTCCGGCATCGCGGAC | ebn1 F201P | SEQ ID NO: 114 |

| Mutation | Oligoname | Sequence 5'→3' | | Sequence No. |
|---|---|---|---|---|
| | Mke 667 | GTCCGCGATGAACGACGTGCTGC | ebn1 F201N | SEQ ID NO: 115 |
| | Mke 668 | GCAGCACGTCGTTCATCGCGGAC | ebn1 F201N | SEQ ID NO: 116 |
| | Mke 669 | GTCCGCGATGATGGACGTGCTGC | ebn1 F201M | SEQ ID NO: 117 |
| | Mke 670 | GCAGCACGTCCATCATCGCGGAC | ebn1 F201M | SEQ ID NO: 118 |
| | Mke 671 | GTCCGCGATGCTAGACGTGCTGC | ebn1 F201L | SEQ ID NO: 119 |
| | Mke 672 | GCAGCACGTCTAGCATCGCGGAC | ebn1 F201L | SEQ ID NO: 120 |
| | Mke 673 | GTCCGCGATGAAGGACGTGCTGC | ebn1 F201K | SEQ ID NO: 121 |
| | Mke 674 | GCAGCACGTCCTTCATCGCGGAC | ebn1 F201K | SEQ ID NO: 122 |
| | Mke 675 | GTCCGCGATGATCGACGTGCTGC | ebn1 F201I | SEQ ID NO: 123 |
| | Mke 676 | GCAGCACGTCGATCATCGCGGAC | ebn1 F201I | SEQ ID NO: 124 |
| | Mke 677 | GTCCGCGATGCATGACGTGCTGC | ebn1 F201H | SEQ ID NO: 125 |
| | Mke 678 | GCAGCACGTCATGCATCGCGGAC | ebn1 F201H | SEQ ID NO: 126 |
| | Mke 679 | GTCCGCGATGGCGGACGTGCTGC | ebn1 F201A | SEQ ID NO: 127 |
| | Mke 680 | GCAGCACGTCCGCCATCGCGGAC | ebn1 F201A | SEQ ID NO: 128 |
| | Mke 681 | GTCCGCGATGGAAGACGTGCTGC | ebn1 F201E | SEQ ID NO: 129 |
| | Mke 682 | GCAGCACGTCTTCCATCGCGGAC | ebn1 F201E | SEQ ID NO: 130 |
| | Mke 683 | GTCCGCGATGGACGACGTGCTGC | ebn1 F201D | SEQ ID NO: 131 |
| | Mke 684 | GCAGCACGTCGTCCATCGCGGAC | ebn1 F201D | SEQ ID NO: 132 |
| | Mke 685 | GTCCGCGATGTGCGACGTGCTGC | ebn1 F201C | SEQ ID NO: 133 |
| | Mke 686 | GCAGCACGTCGCACATCGCGGAC | ebn1 F201C | SEQ ID NO: 134 |
| | Mke 687 | GTCCGCGATGGGCGACGTGCTGC | ebn1 F201G | SEQ ID NO: 135 |
| | Mke 688 | GCAGCACGTCGCCCATCGCGGAC | ebn1 F201G | SEQ ID NO: 136 |
| | Mke 604 | GTCCGCGATGGTGGACGTGCTGC | ebn1 F201V | SEQ ID NO: 137 |
| | Mke 605 | GCAGCACGTCCACCATCGCGGAC | ebn1 F201V | SEQ ID NO: 138 |
| Y151A+ | Mke 951 | GGCAACANNNGAAGCGTC | Y151A T192X | SEQ ID NO: 11 |
| T192X | Mke 952 | GACGCTTCNNNTGTTGCC | Y151A T192X | SEQ ID NO: 12 |

3.3 Activity Tests on the Targeted Mutants

Figure 13A:
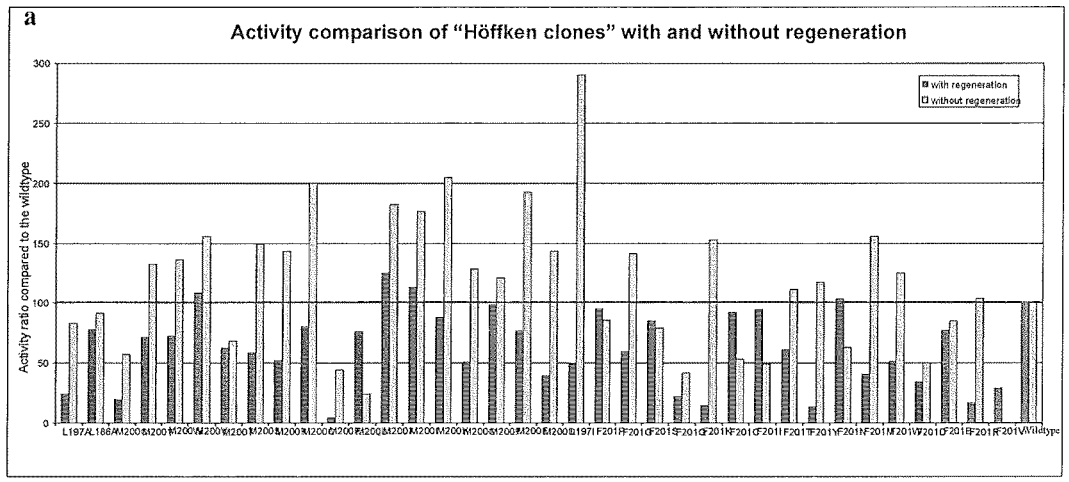
FIG. 13A and FIG. 13B illustrate the results of activity tests with various point mutations according to the invention.
Figure 13B:
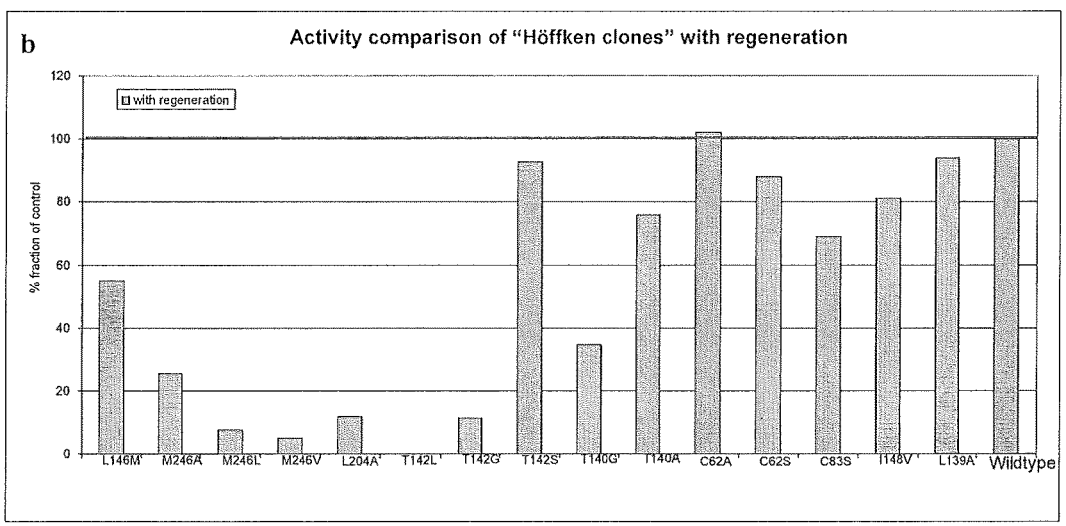

FIG. 13A shows the results from the activity tests in which both the reduction of TAC to TACA with the addition of NADH, and also the overall reaction with regeneration (dark bars) were tested as described in point 2.2. In FIG. 13B, only the total reaction with regeneration has been tested.

In particular, the mutant L197I exhibits an activity which is three times as high as that of the wildtype.

Reference is made expressly to the disclosure of the literature sources cited herein.

The invention claimed is:

1. An isolated functional phenylethanol dehydrogenase mutant of the *Azoarcus* sp. phenylethanol dehydrogenase EbN1 amino acid sequence of SEQ ID NO: 2, wherein the mutant has at least one mutation in at least one sequence region selected from
   (1) positions 142 to 153 (loop 2) of SEQ ID NO: 2; and
   (2) positions 190 to 211 of SEQ ID NO: 2 (helix alpha FG1);
wherein said mutant has at least 90% sequence identity to the amino acid sequence of SEQ ID NO: 2.

2. The mutant of claim 1, which additionally has at least one further mutation in a further sequence region selected from
   (3) positions 93 to 96 of SEQ ID NO: 2 (loop 1);
   (4) positions 241 to 249 of SEQ ID NO: 2 (C terminus);
   (5) positions 138 to 141 of SEQ ID NO: 2 (hydrophilic region of binding pocket);
   (6) position Cys61 of SEQ ID NO: 2; and
   (7) position Cys 83 of SEQ ID NO: 2.

3. The mutant of claim 2, wherein at least one of the following positions of SEQ ID NO: 2 is mutated:
   T192, L197, M200, F201, L204, M246, L139, T140, T142, L146, I148, Y151, C61, C83, L186, and wherein the respective amino acid is replaced by any other natural amino acid.

4. The mutant of claim 1, wherein the mutant comprises at least one of the following mutations:
   a) a single mutation at Y151$X_A$ or T192$X_B$; or
   b) multiple mutations at Y151$X_A$ and T192$X_B$,
where $X_A$=A, R, N, E, Q, G, H, I, L, M, T or V, and $X_B$=A, E, G, I, P, S, W, V or L.

5. The mutant of claim 1, which comprises at least one of the following modified sequences:
   (1) 142-TTYWX$_1$KX$_2$EAX$_3$T-152 (modified loop 2) of SEQ ID NO: 139; or
   (2) 190-ATX$_4$EASAX$_5$SAX$_6$X$_7$DVX$_8$PNMLQAI-211 (modified helix alpha FG1) of SEQ ID NO: 140, wherein $X_1$ to $X_8$, independently of one another, are any amino acid,
and wherein at least one of $X_1$ to $X_3$ and at least one of $X_4$ to $X_8$ is not a natural amino acid of the native enzyme amino acid sequence of SEQ ID NO: 2.

6. The mutant of claim 5, in which
   $X_1$ is L or is substituted by I, V, A, M, F or H;
   $X_2$ is I or is substituted by L, V, A, M, F or H;
   $X_3$ is Y or is substituted by A, R, N, E, Q, G, H, I, L, M, T or V;
   or in which
   $X_4$ is T or is substituted by A, E, G, I, P, S, W, V or L;
   $X_5$ is L or is substituted by I, V, A, M, F or H;
   $X_6$ is M or is substituted by Y, W, E, V, S, R, Q, K, I, H, G, F, E or D;
   $X_7$ is F or is substituted by G, K, T, Y, M, W or R;
   $X_8$ is L or is substituted by I, V, A, M, F or H.

7. The mutant of claim 1, which has at least 50% of the enzymatic activity of the dehydrogenase of SEQ ID NO: 2.

8. The mutant of claim 1, which has at least 95% sequence identity to the amino acid sequence of SEQ ID NO: 2.

9. The mutant of claim 1, which catalyzes the stereospecific equilibrium reaction between 3-chloro-1-(thienyl-2-yl)-propan-1-one (1) and (1S)-3-chloro-1-(thienyl-2-yl)-propan-1-ol (2)

in the presence of the cofactor NAD$^+$ or NADH.

10. An expression cassette comprising at least one nucleic acid sequence encoding the mutant of claim 1 functionally linked to at least one regulatory nucleic acid sequence.

11. A vector comprising at least one expression cassette of claim 10.

12. A recombinant microorganism comprising (a) at least one nucleic acid encoding the mutant of claim 1;

(b) at least one expression cassette comprising said nucleic acid; or (c) at least one vector comprising said expression cassette.

13. A process for producing the mutant of claim 9, which comprises (a) cultivating a recombinant microorganism comprising at least one nucleic acid encoding the mutant;

(b) expressing the at least one nucleic acid sequence encoding the mutant; and optionally (c) isolating the expression product.

14. A process for the biocatalytic synthesis of substituted, optically active alcohols of the formula (II)

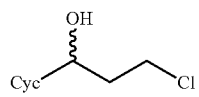
(II)

in which

Cyc is a mono- or polynuclear, saturated or unsaturated, carbocyclic or heterocyclic, optionally mono- or polysubstituted ring, in each case in stereoisomerically pure form or as a mixture of stereoisomers, comprising microbially or enzymatically reducing the ketone of the formula (I)

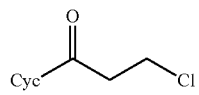
(I)

in the presence of the phenylethanol dehydrogenase mutant of claim 1, optionally with the addition of a reduction equivalent.

15. The process of claim 14, wherein the reaction takes place under conditions of reduction equivalent regeneration, using a $C_1$ to $C_6$-monoalcohol as sacrificial alcohol.

16. The process of claim 14, wherein Cyc is a heterocyclic radical.

17. The process of claim 14, wherein the process produces an essentially enantiomerically pure alcohol of the formula (II).

18. The process of claim 14, wherein (a) the mutant is used in isolated form and optionally immobilized on a solid support; or (b) the mutant is expressed in microbial cells which are optionally immobilized on a solid support.

19. A process for the preparation of duloxetine, comprising (a) biocatalytically reducing 3-chloro-1-(thienyl-2-yl)-propan-1-one (1) to (1S)-3-chloro-1-(thienyl-2-yl)-propan-1-ol (2)

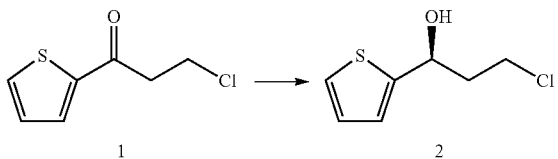 [SMILES: O=C(CCCl)c1cccs1 ; O[C@@H](CCCl)c1cccs1]

using the process of claim 14;

b) chemically converting the alcohol (2) by methylamination to give duloxetine alcohol (3)

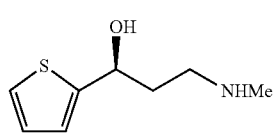

and finally c) chemically converting the duloxetine alcohol (3) by inserting a naphthyl group to duloxetine (4)

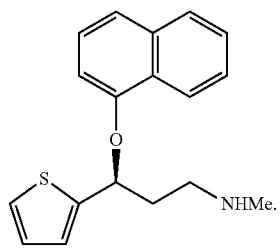

20. A process for the microbial/enzymatic synthesis of substituted ketones of the formula (I)

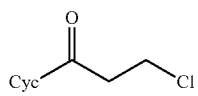
(I)

in which

Cyc is a mono- or polynuclear, saturated or unsaturated, carbocyclic or heterocyclic, optionally mono- or polysubstituted ring, comprising microbially or enzymatically oxidizing the alcohol of the formula (II)

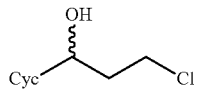
(II)

in each case in stereoisomerically pure form or as a mixture of stereoisomers, in the presence of the phenylethanol dehydrogenase mutant of claim 1, optionally with the addition of oxidation equivalents.

21. The process of claim 20, wherein the reaction takes place under conditions of oxidation equivalent regeneration, using a $C_1$ to $C_6$-monoalkanone as sacrificial ketone.

22. The process of claim 20, wherein
(a) the mutant is used in isolated form and optionally immobilized on a solid support; or
(b) the mutant is expressed in microbial cells which are optionally immobilized on a solid support.

23. A method of preparing duloxetine alcohol or duloxetine comprising
(a) cultivating the recombinant microorganism of claim 12; and
(b) isolating the duloxetine alcohol or duloxetine.

24. The mutant of claim 1, further comprising at least one additional mutation in a position of the amino acid sequence of SEQ ID NO: 2 selected from the group consisting of positions 1, 2, 3, 6, 7, 47, 48, 50, 51, 55, 60, 65, 68, 70, 71, 74, 75, 77, 78, 95, 99, 100, 103, 104, 107, 108, 111, 174, 175, 188, 192, 193, 194, 196, 198, 199, 202, 203, 206, 207, 208, 216, and 230.

25. The mutant of claim 1, wherein the mutant is selected from the group consisting of I119V/I148T, S170P/T191I/L240I, D202V/F234I, W145R/L146I, D62N/I96V/A196V, V125A/D202Y, M200K, Y144F/M207K, A71T/M200V, S195T, L146R, A48V/Y144F/M207K, L9H/N17D/D68G/N113I/H153Q, A194V, W133G/S170P/T191I/L240I, T152A, N17H/D202V/F234I, K129R/N131D/K174R/S195T/G237D, I211T, F201I, Q65R/L146P/I182T/T192I, I155V/S195T, D202G, and M200V/F201L.

* * * * *